United States Patent
Dominguez et al.

(10) Patent No.: US 10,106,535 B2
(45) Date of Patent: *Oct. 23, 2018

(54) HISTONE DEACETYLASE INHIBITORS AND COMPOSITIONS AND METHODS OF USE THEREOF

(71) Applicant: CHDI Foundation, Inc., New York, NY (US)

(72) Inventors: Celia Dominguez, Los Angeles, CA (US); Ignacio Muñoz-Sanjuán, Los Angeles, CA (US); Michel Maillard, Los Angeles, CA (US); Christopher A. Luckhurst, Cambridge (GB); Rebecca E. Jarvis, Saffron Walden (GB); Roland W. Bürli, Hertfordshire (GB); Daniel R. Allen, Saffron Walden (GB); Alan F. Haughan, Cambridge (GB); Perla Breccia, Cambridge (GB); Huw D. Vater, Saffron Walden (GB); Andrew J. Stott, Cambridge (GB); Stephen D. Penrose, Saffron Walden (GB); Michael Wall, Saffron Walden (GB); Elizabeth A. Saville-Stones, Saffron Walden (GB); Grant Wishart, Saffron Walden (GB); Samantha J. Hughes, Saffron Walden (GB)

(73) Assignee: CHDI FOUNDATION, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/482,327

(22) Filed: Apr. 7, 2017

(65) Prior Publication Data

US 2017/0305900 A1 Oct. 26, 2017

Related U.S. Application Data

(63) Continuation of application No. 14/776,320, filed as application No. PCT/US2014/022567 on Mar. 10, 2014, now Pat. No. 9,617,259.

(60) Provisional application No. 61/785,413, filed on Mar. 14, 2013.

(51) Int. Cl.

| | | |
|---|---|---|
| C07D 471/04 | (2006.01) |
| C07C 259/08 | (2006.01) |
| C07D 277/64 | (2006.01) |
| C07D 231/12 | (2006.01) |
| C07D 231/56 | (2006.01) |
| C07D 261/20 | (2006.01) |
| C07D 241/12 | (2006.01) |
| C07D 239/26 | (2006.01) |
| C07D 213/61 | (2006.01) |
| C07D 333/60 | (2006.01) |
| C07D 275/04 | (2006.01) |
| C07D 213/64 | (2006.01) |
| C07D 277/62 | (2006.01) |
| C07D 241/42 | (2006.01) |
| C07D 213/56 | (2006.01) |

(52) U.S. Cl.
CPC .......... *C07D 471/04* (2013.01); *C07C 259/08* (2013.01); *C07D 213/56* (2013.01); *C07D 213/61* (2013.01); *C07D 213/64* (2013.01); *C07D 231/12* (2013.01); *C07D 231/56* (2013.01); *C07D 239/26* (2013.01); *C07D 241/12* (2013.01); *C07D 241/42* (2013.01); *C07D 261/20* (2013.01); *C07D 275/04* (2013.01); *C07D 277/62* (2013.01); *C07D 277/64* (2013.01); *C07D 333/60* (2013.01); *C07C 2601/02* (2017.05); *C07C 2601/10* (2017.05)

(58) Field of Classification Search
None
See application file for complete search history.

(56) References Cited

U.S. PATENT DOCUMENTS

| | | | |
|---|---|---|---|
| 4,003,859 A | 1/1977 | Reymore, Jr. et al. |
| 5,384,331 A | 1/1995 | Kogan et al. |
| 9,617,259 B2* | 4/2017 | Dominguez | C07D 231/12 |
| 2006/0019944 A1 | 1/2006 | Wu et al. |
| 2006/0069157 A1 | 3/2006 | Ferrante |
| 2008/0269294 A1 | 10/2008 | Andrews et al. |

(Continued)

FOREIGN PATENT DOCUMENTS

| | | |
|---|---|---|
| EP | 1446155 | 2/2008 |
| WO | WO 2008/12115 | 10/2008 |

(Continued)

OTHER PUBLICATIONS

Database CAPLUS; Accession No. 1984: 185792, Tihanyi et al., HU 27601, 1980.

(Continued)

*Primary Examiner* — Brian J Davis
(74) *Attorney, Agent, or Firm* — Sheppard Mullin Richter & Hampton LLP

(57) ABSTRACT

Provided are certain histone deacetylase (HDAC) inhibitors of Formula I, compositions thereof, and methods of their use.

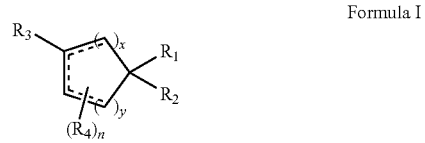

Formula I

18 Claims, No Drawings

(56) References Cited

U.S. PATENT DOCUMENTS

| | | | |
|---|---|---|---|
| 2009/0181943 | A1 | 7/2009 | Tessier et al. |
| 2012/0121502 | A1 | 5/2012 | Van Duzer et al. |
| 2014/0163009 | A1 | 6/2014 | Luckhurst et al. |
| 2015/0203468 | A1 | 7/2015 | Dominguez et al. |
| 2016/0024019 | A1 | 1/2016 | Dominguez et al. |
| 2016/0031863 | A1 | 2/2016 | Dominguez et al. |
| 2016/0039745 | A1 | 2/2016 | Dominguez et al. |

FOREIGN PATENT DOCUMENTS

| | | |
|---|---|---|
| WO | WO 2008/122115 | 10/2008 |
| WO | WO 2012/103008 | 8/2012 |
| WO | WO 2015/187542 | 12/2015 |

OTHER PUBLICATIONS

Database CAPLUS in STN. Acc. No. 1991:631727, Dang et al., Journal of the Chemical Society, Perkin Transactions 2: Physical Organic Chemistry (1972-1999) (1991), 5, pp. 721-734 (abstract).

Extended European Search Report for EP Appl. No. 14775535.9 dated Aug. 26, 2016 (7 pages).

Extended European Search Report for EP Appl. No. 14775793.4 dated Jul. 6, 2016 (9 pages).

Heinemann, B. Prophage Induction in Lysogenic *Escherichia coli* with Simple Hydroxylamine and Hydrazine Compounds. Applied Microbiology, vol. 21, No. 4, Apr. 1971, pp. 726-731.

International Search Report and Written Opinion dated Aug. 4, 2014 for PCT Application No. PCT/US2014/022550 (8 pages).

International Search Report and Written Opinion dated May 24, 2014 for PCT Application No. PCT/US2014/022597 (8 pages).

International Search Report and Written Opinion for International Application No. PCT/US2014/022567 dated Jul. 21, 2014 (13 pages).

PUBCHEM CID 21702499, Dec. 5, 2007, pp. 1-10 [online], [retrieved on Jun. 16, 2016]. Retrieved from the Internet <URL: https://pubchem.ncbi.nlm.nih.gov/summary/summary.cgi?cid=21702499>; p. 1, formula.

PUBCHEM CID 331910, Mar. 26, 2005, pp. 1-14 [online], [retrieved on Jun. 16, 2016]. Retrieved from the Internet <URL: https://pubchem.ncbi.nlm.nih.gov/summary/summary.cgi?cid=331910>; p. 1, formula.

PUBCHEM CID 57779614. Aug. 19, 2012, pp. 1-4 [online], [retrieved on Jun. 16, 2014]. Retrieved from the Internet <URL: https://pubchem.ncbi.nlm.nih.gov/summary/summary.cgi?cid=57779614&loc=ec_rcs>; p. 1, formula.

PUBCHEM. CID 59191078. Aug. 20, 2012, pp. 1-4 [online], [retrieved on Jun. 16, 2014). Retrieved from the Internet <URL: https://pubchem.ncbi.nlm.nih.gov/summary/summary.cgi?cid=59191078&loc=ec_rcs>; p. 1, formula.

Wu, Z et al. A High-Affinity Fluorenone-Based Beta2-Adrenergic Receptor Antagonist with a Photoactivatable Pharmacophore. Biochemistry, vol. 39, No. 42, 2000, pp. 13044-13052 [online], [retrieved on Jun. 16, 2014). Retrieved from the Internet<URL: http://pubs.acs.org/doi/abs/1O.1021/bi001342k?journalCode=bichaw><DOI: 10.•1021/bi001342k>; abstract.

Patani, et al. Bioisosterism: A Rational Approach in Drug Design. Chem Rev. Dec. 19, 1996;96(8):3147-3176.

\* cited by examiner

HISTONE DEACETYLASE INHIBITORS AND COMPOSITIONS AND METHODS OF USE THEREOF

This application is a continuation of U.S. application Ser. No. 14/776,320, filed Sep. 14, 2015, which claims the benefit of priority under 35 U.S.C. § 371 of PCT International Application No. PCT/US2014/022567, filed Mar. 10, 2014, which in turn claims the benefit of priority to U.S. provisional application 61/785,413, filed Mar. 14, 2013, which is incorporated herein by reference in its entirety.

Provided herein are certain histone deacetylase (HDAC) inhibitors, compositions thereof, and methods of their use.

Histone deacetylases (HDACs) are zinc-containing enzymes which catalyse the removal of acetyl groups from the ε-amino termini of lysine residues clustered near the amino terminus of nucleosomal histones. There are 11 known metal-dependent human histone deacetylases, grouped into four classes based on the structure of their accessory domains. Class I includes HDAC1, HDAC2, HDAC3, and HDAC8 and have homology to yeast RPD3. HDAC4, HDAC5, HDAC7, and HDAC9 belong to Class IIa and have homology to yeast HDAC1. HDAC6 and HDAC10 contain two catalytic sites and are classified as Class IIb, whereas HDAC11 has conserved residues in its catalytic center that are shared by both Class I and Class II deacetylases and is sometimes placed in Class IV.

Provided is a compound of Formula I, or a pharmaceutically acceptable salt thereof,

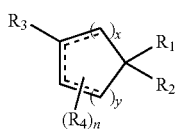

Formula I wherein:
each of the dashed lines indicate a single or double bond, provided that the ring contains one or two double bonds that are non-adjacent;
$R^1$ is chosen from —C(O)NH(OH) and —N(OH)C(O)$R^5$ wherein $R^5$ is chosen from hydrogen, lower alkyl and lower haloalkyl;
$R^2$ is aryl, heteroaryl, and heterocycloalkyl, each of which is optionally substituted with 1 to 3 substituents independently chosen from halo, alkyl, cycloalkyl, haloalkyl, hydroxyl, alkoxy, and nitrile; and
$R^3$ is chosen from hydrogen, alkyl, cycloalkyl, heterocycloalkyl, aryl, heteroaryl, aralkyl, and heteroaralkyl, each of which is optionally substituted with 1 to 3 substituents independently chosen from halo, CONR$_b$R$_c$, alkyl, alkyl substituted with —NR$_b$R$_c$, cycloalkyl, haloalkyl, hydroxyl, alkoxy, alkoxy substituted with —NR$_b$R$_c$, aryl, heteroaryl, and nitrile;
for each occurrence, $R^4$ is independently chosen from halo, lower alkyl, lower haloalkyl, and hydroxyl;
x and y are independently chosen from 1, 2, and 3, provided that the sum of x+y is ≤4,
n is chosen from 0, 1, 2 and 3;
$R^b$ is chosen from H, $C_1$-$C_6$ alkyl, aryl, and heteroaryl; and
$R^c$ is chosen from hydrogen and $C_1$-$C_4$ alkyl; or
$R^b$ and $R^c$, and the nitrogen to which they are attached, form a heterocycloalkyl group; and
where for $R^b$ and $R^c$, each $C_1$-$C_6$ alkyl, cycloalkyl, aryl, heterocycloalkyl, and heteroaryl is unsubstituted or substituted with one or more substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —$C_1$-$C_4$ alkyl-O—$C_1$-$C_4$ alkyl, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

Also provided is a pharmaceutical composition comprising a compound, or a pharmaceutically acceptable salt thereof, described herein and at least one pharmaceutically acceptable excipient.

Also provided is a method of treating a condition or disorder mediated by at least one histone deacetylase in a subject in need of such a treatment which method comprises administering to the subject a therapeutically effective amount of a compound, or a pharmaceutically acceptable salt thereof, described herein.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halo" includes fluoro, chloro, bromo, and iodo, and the term "halogen" includes fluorine, chlorine, bromine, and iodine.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic).

Examples of monocyclic heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from
—$R^a$, —$OR^b$, —O($C_1$-$C_2$ alkyl)O— (e.g., methylenedioxy-), —$SR^b$, guanidine (—NHC(=NH)$NH_2$), guanidine wherein one or more of the guanidine hydrogens are replaced with a $C_1$-$C_4$ alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl;
$R^b$ is chosen from H, $C_1$-$C_6$ alkyl, aryl, and heteroaryl; and
$R^c$ is chosen from hydrogen and $C_1$-$C_4$ alkyl; or
$R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_p-COOH$ where p is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As used herein the terms "group", "radical" or "fragment" are synonymous and are intended to indicate functional groups or fragments of molecules attachable to a bond or other fragments of molecules.

The term "active agent" is used to indicate a compound or a pharmaceutically acceptable salt thereof which has biological activity. In some embodiments, an "active agent" is a compound or pharmaceutically acceptable salt thereof having pharmaceutical utility. For example an active agent may be an anti-neurodegenerative therapeutic.

The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of HDAC activity.

As used herein, the terms "histone deacetylase" and "HDAC" are intended to refer to anyone of a family of enzymes that remove $N^\varepsilon$-acetyl groups from the ε-amino groups of lysine residues of a protein (for example, a histone, or tubulin). Unless otherwise indicated by context, the term "histone" is meant to refer to any histone protein, including H1, H2A, H2B, H3, H4, and H5, from any species. In some embodiments, the histone deacetylase is a human HDAC, including, but not limited to, HDAC-4, HDAC-5, HDAC-6, HDAC-7, HDAC-9, and HDAC-10. In some embodiments, at least one histone deacetylase is selected from HDAC-4, HDAC-5, HDAC-7, and HDAC-9. In some embodiments, the histone deacetylase is a class IIa HDAC. In some embodiments, the histone deacetylase is HDAC-4. In some embodiments, the histone deacetylase is HDAC-5. In some embodiments, the histone deacetylase is derived from a protozoal or fungal source.

The terms "histone deacetylase inhibitor" and "inhibitor of histone deacetylase" are intended to mean a compound, or a pharmaceutically acceptable salt thereof, described herein which is capable of interacting with a histone deacetylase and inhibiting its enzymatic activity.

The term "a condition or disorder mediated by HDAC" or "a condition or disorder mediated by histone deacetylase" as used herein refers to a condition or disorder in which HDAC and/or the action of HDAC is important or necessary, e.g., for the onset, progress, expression, etc. of that condition, or a condition which is known to be treated by HDAC inhibitors (such as, e.g., trichostatin A).

The term "effect" describes a change or an absence of a change in cell phenotype or cell proliferation. "Effect" can also describe a change or an absence of a change in the catalytic activity of HDAC. "Effect" can also describe a change or an absence of a change in an interaction between HDAC and a natural binding partner.

The term "inhibiting histone deacetylase enzymatic activity" is intended to mean reducing the ability of a histone deacetylase to remove an acetyl group from a protein, such as but not limited to a histone or tubulin. The concentration of inhibitor which reduces the activity of a histone deacetylase to 50% of that of the uninhibited enzyme is determined as the $IC_{50}$ value. In some embodiments, such reduction of histone deacetylase activity is at least 50%, such as at least about 75%, for example, at least about 90%. In some embodiments, histone deacetylase activity is reduced by at least 95%, such as by at least 99%. In some embodiments, the compounds and pharmaceutical acceptable salts thereof described herein have an $IC_{50}$ value less than 100 nanomolar. In some embodiments, the compounds and pharmaceutical acceptable salts thereof described herein have an $IC_{50}$ value from 100 nanomolar to 1 micromolar. In some embodiments, the compounds and pharmaceutical acceptable salts thereof described herein have an $IC_{50}$ value from 1 to 25 micromolar.

In some embodiments, such inhibition is specific, i.e., the histone deacetylase inhibitor reduces the ability of a histone deacetylase to remove an acetyl group from a protein at a concentration that is lower than the concentration of the inhibitor that is required to produce another, unrelated biological effect. In some embodiments, the concentration of the inhibitor required for histone deacetylase inhibitory activity is at least 2-fold lower, such as at least 5-fold lower, for example, at least 10-fold lower, such as at least 20-fold lower than the concentration required to produce an unrelated biological effect.

"Treatment" or "treating" means any treatment of a disease state in a patient, including
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal; and in some embodiments the subject is human.

Provided is a compound of Formula I, or a pharmaceutically acceptable salt thereof,

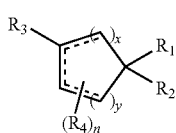

Formula I wherein:
each of the dashed lines indicate a single or double bond, provided that the ring contains one or two double bonds that are non-adjacent;
$R^1$ is chosen from —C(O)NH(OH) and —N(OH)C(O)$R^5$ wherein $R^5$ is chosen from hydrogen, lower alkyl and lower haloalkyl;
$R^2$ is aryl, heteroaryl, and heterocycloalkyl, each of which is optionally substituted with 1 to 3 substituents independently chosen from halo, alkyl, cycloalkyl, haloalkyl, hydroxyl, alkoxy, and nitrile; and
$R^3$ is chosen from hydrogen, alkyl, cycloalkyl, heterocloalkyl, aryl, heteroaryl, aralkyl, and heteroaralkyl, each of which is optionally substituted with 1 to 3 substituents independently chosen from halo, CONR$_b$R$_c$, alkyl, alkyl substituted with —NR$_b$R$_c$, cycloalkyl, haloalkyl, hydroxyl, alkoxy, alkoxy substituted with —NR$_b$R$_c$, aryl, heteroaryl, and nitrile;
for each occurrence, $R^4$ is independently chosen from halo, lower alkyl, lower haloalkyl, and hydroxyl;
x and y are independently chosen from 1, 2, and 3, provided that the sum of x+y is ≤4,
n is chosen from 0, 1, 2 and 3;
$R^b$ is chosen from H, $C_1$-$C_6$ alkyl, aryl, and heteroaryl; and
$R^c$ is chosen from hydrogen and $C_1$-$C_4$ alkyl; or
$R^b$ and $R^c$, and the nitrogen to which they are attached, form a heterocycloalkyl group; and
where for $R^b$ and $R^c$, each $C_1$-$C_6$ alkyl, cycloalkyl, aryl, heterocycloalkyl, and heteroaryl is unsubstituted or substituted with one or more substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —$C_1$-$C_4$ alkyl-O—$C_1$-$C_4$ alkyl, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

In some embodiments, $R^1$ is —C(O)NH(OH).
In some embodiments, $R^1$ is —N(OH)C(O)$R^5$. In some embodiments, $R^5$ is chosen from hydrogen and lower alkyl. In some embodiments, $R^5$ is lower alkyl.
In some embodiments, $R^2$ is phenyl optionally substituted with 1 to 3 substituents independently chosen from halo, alkyl, cycloalkyl, haloalkyl, hydroxyl, alkoxy, and nitrile. In some embodiments, $R^2$ is phenyl optionally substituted with 1 to 3 substituents independently chosen from halo, lower alkyl, and haloalkyl. In some embodiments, $R^2$ is chosen from phenyl, 2-fluorophenyl, 2-methyl, 3-fluoro-2-methylphenyl, 3,4-difluoro-2-methylphenyl, and 2-methylphenyl. In some embodiments, $R^2$ is chosen from phenyl, 2-fluorophenyl, 2-methyl, 3-fluoro-2-methylphenyl and 2-methylphenyl. In some embodiments, $R^2$ is 3-fluoro-2-methylphenyl.

In some embodiments, $R^2$ is heteroaryl optionally substituted with 1 to 3 substituents independently chosen from halo, lower alkyl, and haloalkyl. In some embodiments, $R^2$ is pyridinyl optionally substituted with 1 to 3 substituents independently chosen from halo, lower alkyl, and haloalkyl. In some embodiments, $R^2$ is 2-methylpyridin-3-yl.

In some embodiments, x is 1. In some embodiments, x is 2. In some embodiments, x is 3.

In some embodiments, x is 1 and y is chosen from 1, 2, and 3. In some embodiments, x is 2 and y is chosen from 1 and 2. In some embodiments, x is 3 and y is 1.

In some embodiments, y is 1. In some embodiments, y is 2. In some embodiments, y is 3.

In some embodiments, y is 1 and x is chosen from 1, 2, and 3. In some embodiments, y is 2 and x is chosen from 1 and 2. In some embodiments, y is 3 and x is 1.

In some embodiments, the compound of Formula I is chosen from compounds of Formula II, Formula III, and Formula IV.

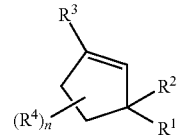

Formula II

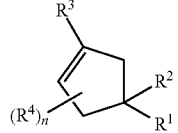

Formula III

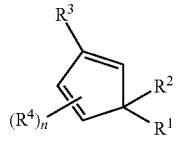

Formula IV

In some embodiments, the compound of Formula I is chosen from compounds of Formula V-X.

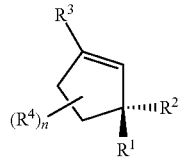

Formula V

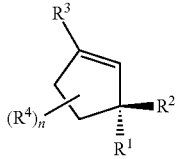

Formula VI

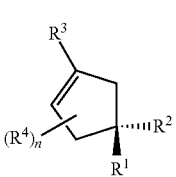

Formula VII

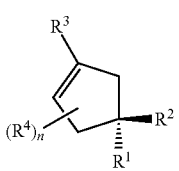

Formula VIII

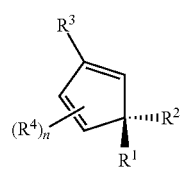

Formula IX

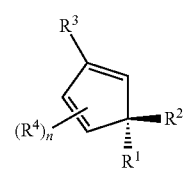

Formula X

In some embodiments, the compound of Formula I is chosen from compounds of Formula XI-XIII.

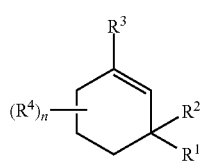

Formula XI

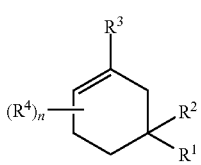

Formula XII

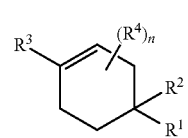

Formula XIII

In some embodiments, $R^3$ is chosen from hydrogen, alkyl, cycloalkyl, heterocycloalkyl, aryl, heteroaryl, aralkyl, and heteroaralkyl, each of which is optionally substituted with 1 to 3 substituents independently chosen from halo, alkyl, cycloalkyl, haloalkyl, hydroxyl, alkoxy, and nitrile.

In some embodiments, $R^3$ is chosen from hydrogen and alkyl optionally substituted with 1 to 3 substituents independently chosen from halo, cycloalkyl, haloalkyl, hydroxyl, alkoxy, and nitrile. In some embodiments, $R^3$ is chosen from hydrogen and alkyl optionally substituted with 1 to 3 substituents independently chosen from halo, hydroxyl, and alkoxy.

In some embodiments, $R^3$ is aryl optionally substituted with 1 to 3 substituents independently chosen from halo, alkyl, cycloalkyl, haloalkyl, hydroxyl, alkoxy, and nitrile. In some embodiments, $R^3$ is chosen from phenyl, 2-methylphenyl, 3,4-dihydro-2H-benzo[b][1,4]oxazin-6-yl, 4,4-difluoro-1,2,3,4-tetrahydroquinolin-7-yl, and 4,4,8-trifluoro-1,2,3,4-tetrahydroquinolin-6-yl.

In some embodiments, $R^3$ is heteroaryl optionally substituted with 1 to 3 substituents independently chosen from halo, alkyl, cycloalkyl, haloalkyl, hydroxyl, alkoxy, and nitrile. In some embodiments, $R^3$ is chosen from 6-methylpyridin-3-yl, 6-trifluoromethylpyridin-3-yl, 5-fluoropyridin-3-yl, 5-(trifluoromethyl)pyrimidin-2-yl, 5-methylpyrimidin-2-yl, pyrimidin-2-yl, 2-(trifluoromethyl)pyrimidin-5-yl, 2-methylpyrimidin-5-yl, pyrimidin-5-yl, 2-(trifluoromethyl)pyrimidin-4-yl, 2-methylpyrimidin-4-yl, pyrimidin-4-yl, 6-(trifluoromethyl)pyridazin-4-yl, 6-methylpyridazin-4-yl, pyridazin-4-yl, 6-cyclopropylpyridazin-4-yl, pyrazin-2-yl, 5-(trifluoromethyl)pyrazin-2-yl, 5-methylpyrazin-2-yl, 3-cyclopropylpyrazin-2-yl, 1H-pyrazol-1-yl, 1-(2,2,2-trifluoroethyl)-1H-pyrazol-4-yl, oxazol-2-yl, 2-cyclopropyloxazol-5-yl, thiazol-2-yl, 2-cyclopropylthiazol-5-yl, 1,3,4-thiadiazol-2-yl, 2-methylbenzo[d]oxazol-5-yl, 1H-pyrrolo[2,3-b]pyridin-6-yl, imidazo[1,2-a]pyridin-7-yl, 1H-indazol-6-yl, and 2-oxo-1,2-dihydropyridin-3-yl.

In some embodiments, $R^3$ is heterocycloalkyl optionally substituted with 1 to 3 substituents independently chosen from halo, alkyl, cycloalkyl, haloalkyl, hydroxyl, alkoxy, aryl, heteroaryl, and nitrile. In some embodiments, $R^3$ is chosen from 1H-pyrrolo[3,4-c]pyridin-2(3H)-yl, 3,4-dihydroisoquinolin-2(1H)-yl, 4-cyclopropylpiperazin-1-yl, 1-(2,2,2-trifluoroethyl)piperidin-4-yl, and 1-cyclopropylpiperidin-4-yl.

In some embodiments, n is 0. In some embodiments, n is 1. In some embodiments, n is 2. In some embodiments, n is 3.

In some embodiments, for each occurrence, $R^4$ is independently chosen from halo and lower alkyl.

Also provided is a compound chosen from
(R)-1-(3-fluoro-2-methylphenyl)-N-hydroxy-3-phenylcyclopent-2-enecarboxamide;
(S)-1-(3-fluoro-2-methylphenyl)-N-hydroxy-3-phenylcyclopent-2-enecarboxamide;
(R)-1-(3-fluoro-2-methylphenyl)-N-hydroxy-3-(o-tolyl)cyclopent-2-enecarboxamide;
(S)-1-(3-fluoro-2-methylphenyl)-N-hydroxy-3-(o-tolyl)cyclopent-2-enecarboxamide;
(R)-1-(3-fluoro-2-methylphenyl)-3-(5-fluoropyridin-3-yl)-N-hydroxycyclopent-2-enecarboxamide;
(S)-1-(3-fluoro-2-methylphenyl)-3-(5-fluoropyridin-3-yl)-N-hydroxycyclopent-2-enecarboxamide;
(R)-1-(3-fluoro-2-methylphenyl)-N-hydroxy-3-(pyrazin-2-yl)cyclopent-2-enecarboxamide;
(S)-1-(3-fluoro-2-methylphenyl)-N-hydroxy-3-(pyrazin-2-yl)cyclopent-2-enecarboxamide;
(R)-1-(3-fluoro-2-methylphenyl)-N-hydroxy-3-(2-methylpyrimidin-5-yl)cyclopent-2-enecarboxamide;
(S)-1-(3-fluoro-2-methylphenyl)-N-hydroxy-3-(2-methylpyrimidin-5-yl)cyclopent-2-enecarboxamide;
(S)-3-(5-chloropyridin-3-yl)-1-(3-fluoro-2-methylphenyl)-N-hydroxycyclopent-2-enecarboxamide;
(S)-1-(3-fluoro-2-methylphenyl)-N-hydroxy-3-(quinoxalin-6-yl)cyclopent-2-enecarboxamide;
(S)-1-(3-fluoro-2-methylphenyl)-N-hydroxy-3-(2-(trifluoromethyl)pyridin-4-yl)cyclopent-2-enecarboxamide;
(S)-1-(3-fluoro-2-methylphenyl)-N-hydroxy-3-(pyrimidin-5-yl)cyclopent-2-enecarboxamide;
(S)-1-(3-fluoro-2-methylphenyl)-3-(5-fluoropyridin-2-yl)-N-hydroxycyclopent-2-enecarboxamide;

(S)-1-(3-fluoro-2-methylphenyl)-N-hydroxy-3-(6-(trifluoromethyl)pyridin-3-yl)cyclopent-2-enecarboxamide;
(S)-1-(3-fluoro-2-methylphenyl)-N-hydroxy-3-(5-(trifluoromethyl)pyridin-3-yl)cyclopent-2-enecarboxamide;
(S)-3-(1-(difluoromethyl)-1H-pyrazol-4-yl)-1-(3-fluoro-2-methylphenyl)-N-hydroxycyclopent-2-enecarboxamide;
(S)-3-(2-cyclopropyl-5-fluoropyridin-3-yl)-1-(3-fluoro-2-methylphenyl)-N-hydroxycyclopent-2-enecarboxamide;
(S)-1-(3-fluoro-2-methylphenyl)-N-hydroxy-3-(2-(trifluoromethyl)quinoxalin-6-yl)cyclopent-2-enecarboxamide;
(S)-1-(3-fluoro-2-methylphenyl)-N-hydroxy-3-(imidazo[1,2-a]pyridin-7-yl)cyclopent-2-enecarboxamide;
(S)-1-(3-fluoro-2-methylphenyl)-N-hydroxy-3-(3-methylbenzo[d]isoxazol-5-yl)cyclopent-2-enecarboxamide;
(S)-1-(3-fluoro-2-methylphenyl)-3-(5-fluoro-6-methoxypyridin-3-yl)-N-hydroxycyclopent-2-enecarboxamide;
(S)-3-(2-cyclopropylpyrimidin-5-yl)-1-(3-fluoro-2-methylphenyl)-N-hydroxycyclopent-2-enecarboxamide;
(S)-1-(3-fluoro-2-methylphenyl)-N-hydroxy-3-(6-methylpyridin-3-yl)cyclopent-2-enecarboxamide;
(S)-3-(5-chloro-6-methylpyridin-3-yl)-1-(3-fluoro-2-methylphenyl)-N-hydroxycyclopent-2-enecarboxamide;
(S)-1-(3-fluoro-2-methylphenyl)-N-hydroxy-3-(1-methyl-1H-pyrazol-5-yl)cyclopent-2-enecarboxamide;
(S)-1-(3-fluoro-2-methylphenyl)-N-hydroxy-3-(1-(2,2,2-trifluoroethyl)-1H-pyrazol-4-yl)cyclopent-2-enecarboxamide;
(S)-3-(benzo[d]isothiazol-7-yl)-1-(3-fluoro-2-methylphenyl)-N-hydroxycyclopent-2-enecarboxamide;
N-hydroxy-1-phenylcyclopent-3-enecarboxamide; and
1-(2-fluorophenyl)-N-hydroxycyclopent-3-enecarboxamide,
or a pharmaceutically acceptable salt thereof.

Also provided is a compound chosen from
(S)-3-(1-(2-(diethylamino)ethyl)-1H-pyrazol-4-yl)-1-(3-fluoro-2-methylphenyl)-N-hydroxycyclopent-2-enecarboxamide;
(S)-3-(1-(3-(diethylamino)propyl)-1H-pyrazol-4-yl)-1-(3-fluoro-2-methylphenyl)-N-hydroxycyclopent-2-enecarboxamide;
(S)-3-(1-(2-(diethylamino)ethyl)-1H-indazol-6-yl)-1-(3-fluoro-2-methylphenyl)-N-hydroxycyclopent-2-enecarboxamide;
(1S)-1-(3-fluoro-2-methylphenyl)-3-(3-fluoro-5-(1-(pyrrolidin-1-yl)propan-2-yl)phenyl)-N-hydroxycyclopent-2-enecarboxamide;
(S)-3-(3-(2-(diethylamino)ethoxy)-5-fluorophenyl)-1-(3-fluoro-2-methylphenyl)-N-hydroxycyclopent-2-enecarboxamide;
(S)-3-(3-((diethylamino)methyl)-5-fluorophenyl)-1-(3-fluoro-2-methylphenyl)-N-hydroxycyclopent-2-enecarboxamide;
(S)-3-(2-(2-(diethylamino)ethoxy)pyridin-4-yl)-1-(3-fluoro-2-methylphenyl)-N-hydroxycyclopent-2-enecarboxamide;
(S)-3-(5-(2-(diethylamino)ethoxy)pyridin-3-yl)-1-(3-fluoro-2-methylphenyl)-N-hydroxycyclopent-2-enecarboxamide; and
(S)-1-(3-fluoro-2-methylphenyl)-3-(5-fluoro-6-(2-(pyrrolidin-1-yl)ethoxy)pyridin-3-yl)-N-hydroxycyclopent-2-enecarboxamide,
or a pharmaceutically acceptable salt thereof.

Also provided is a compound chosen from
(S)-3-cyclopropyl-1-(3-fluoro-2-methylphenyl)-N-hydroxycyclopent-2-enecarboxamide;
(S)-N-hydroxy-1,3-diphenylcyclopent-2-enecarboxamide;
(R)-N-hydroxy-1,3-diphenylcyclopent-2-enecarboxamide;
(S)-3-(5-fluoropyridin-3-yl)-N-hydroxy-1-phenylcyclopent-2-enecarboxamide;
(S)-3-(5-chloro-2-methylpyridin-3-yl)-1-(3-fluoro-2-methylphenyl)-N-hydroxycyclopent-2-enecarboxamide;
(S)-1-(3-fluoro-2-methylphenyl)-N-hydroxy-3-(2-methylpyridin-3-yl)cyclopent-2-enecarboxamide;
(S)-1-(3-fluoro-2-methylphenyl)-N-hydroxy-3-(1-methyl-1H-indazol-6-yl)cyclopent-2-enecarboxamide;
(S)-3-(1-(difluoromethyl)-1H-indazol-6-yl)-1-(3-fluoro-2-methylphenyl)-N-hydroxycyclopent-2-enecarboxamide;
(S)-3-(benzo[d]thiazol-5-yl)-1-(3-fluoro-2-methylphenyl)-N-hydroxycyclopent-2-enecarboxamide;
(S)-3-(benzo[b]thiophen-2-yl)-1-(3-fluoro-2-methylphenyl)-N-hydroxycyclopent-2-enecarboxamide;
(S)-1-(3,4-difluoro-2-methylphenyl)-N-hydroxy-3-(1-methyl-1H-indazol-6-yl)cyclopent-2-enecarboxamide;
4-(5-fluoropyridin-3-yl)-N-hydroxy-1,2,3,6-tetrahydro-[1,1'-biphenyl]-1-carboxamide;
3'-fluoro-4-(5-fluoropyridin-3-yl)-N-hydroxy-2'-methyl-1,2,3,6-tetrahydro-[1,1'-biphenyl]-1-carboxamide; and
(S)-1-(3-fluoro-2-methylphenyl)-N-hydroxy-3-(quinoxalin-6-yl)cyclopent-2-enecarboxamide;
or a pharmaceutically acceptable salt thereof.

Methods for obtaining the compounds, or pharmaceutically acceptable salts thereof, described herein will be apparent to those of ordinary skill in the art, suitable procedures being described, for example, in examples below, and in the references cited herein.

Also provided is a method for inhibiting at least one histone deacetylase. In some embodiments, the at least one histone deacetylase is a class IIa HDAC. In some embodiments, the at least one histone deacetylase is selected from HDAC-4, HDAC-5, HDAC-7, and HDAC-9. In some embodiments, the inhibition is in a cell. In some embodiments, the compound, or pharmaceutically acceptable salt thereof, described herein is selective for inhibiting at least one class II histone deacetylase. In some embodiments, the compound, or pharmaceutically acceptable salt thereof, described herein is a selective inhibitor of HDAC-4 and/or HDAC-5.

Also provided is a method of treating a condition or disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a neurodegenerative pathology. Accordingly, also provided is a method of treating a neurodegenerative pathology mediated by HDAC in a subject in need of such a treatment, comprising administering to the subject a therapeutically effective amount of at least one compound, or pharmaceutically acceptable salt thereof, described herein.

In some embodiments, the neurodegenerative pathology is chosen from Alzheimer's disease, Parkinson's disease, neuronal intranuclear inclusion disease (NIID), Dentatorubral pallidolusyian atrophy (DRPLA), Friedreich's ataxia, Rubenstein-Taubi Syndrome, and polyglutamine diseases such as Huntington's disease; spinocerebellar ataxia 1 (SCA 1), spinocerebellar ataxia 7 (SCA 7), seizures, striatonigral degeneration, progressive supranuclear palsy, torsion dystonia, spasmodic torticollis, dyskinesis, familial tremor, Gilles de la Tourette syndrome, diffuse Lewy body disease, progressive supranuclear palsy, Pick's disease, primary lateral sclerosis, progressive neural muscular atrophy, spinal muscular atrophy, hypertrophic interstitial polyneuropathy, retinitis pigmentosa, hereditary optic atrophy, hereditary spastic paraplegia, Shy-Drager syndrome, Kennedy's disease, protein-aggregation-related neurodegeneration, Machado-Joseph's disease, spongiform encephalopathy, prion-related disease, multiple sclerosis (MS), progressive supranuclear palsy (Steel-Richardson-Olszewski disease), Hallervorden-Spatz disease, progressive familial myoclonic epilepsy, cerebellar degeneration, motor neuron disease, Werdnig-Hoffman disease, Wohlfart-Kugelberg-Welander disease, Charcot-Marie-Tooth disease, Dejerine-Sottas disease, retinitis pigmentosa, Leber's disease, progressive systemic sclerosis, dermatomyositis, and mixed connective tissue disease.

In some embodiments, the neurodegenerative pathology is an acute or chronic degenerative disease of the eye. Acute or chronic degenerative diseases of the eye include glaucoma, dry age-related macular degeneration, retinitis pigmentosa and other forms of heredodegenerative retinal disease, retinal detachment, macular pucker, ischemia affecting the outer retina, cellular damage associated with diabetic retinopathy and retinal ischemia, damage associated with laser therapy, ocular neovascular, diabetic retinopathy, rubeosis iritis, uveitis, Fuch's heterochromatic iridocyclitis, neovascular glaucoma, corneal neovascularization, retinal ischemia, choroidal vascular insufficiency, choroidal thrombosis, carotid artery ischemia, contusive ocular injury, retinopathy of permaturity, retinal vein occlusion, proliferative vitreoretinopathy, corneal angiogenesis, retinal microvasculopathy, and retinal eduema.

In some embodiments, the condition or disorder mediated by HDAC comprises a fibrotic disease such as liver fibrosis, cystic fibrosis, cirrhosis, and fibrotic skin diseases, e.g., hypertrophic scars, keloid, and Dupuytren's contracture. Accordingly, also provided is a method of treating a fibrotic disease mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a psychological disorder, such as depression, bipolar disease and dementia. In some embodiments, the condition or disorder mediated by HDAC comprises depression. Accordingly, also provided is a method of treating a psychological disorder, such as depression, mediated by HDAC in a subject in need of such a treatment, comprising administering to the subject a therapeutically effective amount of at least one compound, or pharmaceutically acceptable salt thereof, described herein. In some embodiments, the depression is chosen from major depressive disorder, and bipolar disorder.

In some embodiments, the condition or disorder mediated by HDAC comprises anxiety. Accordingly, also provided is a method of treating an anxiety mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises schizophrenia. Accordingly, also provided is a method of treating a schizophrenia mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a motor neuron disease, muscle atrophy/muscle wasting disorders, or amyotrophic lateral sclerosis (ALS). Accordingly, also provided is a method of treating a motor neuron disease, muscle atrophy/muscle wasting disorders, or amyotrophic lateral sclerosis (ALS) mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a cardiovascular condition. Accordingly, also provided is a method of treating a cardiovascular condition mediated by HDAC in a subject in need of such a treatment, comprising administering to the subject a therapeutically effective amount of at least one compound, or pharmaceutically acceptable salt thereof, described herein. In some embodiments, the cardiovascular condition is chosen from cardiomyopathy, cardiac hypertrophy, myocardial ischemia, heart failure, cardiac restenosis, and arteriosclerosis.

In some embodiments, the condition or disorder mediated by HDAC comprises cancer. Accordingly, also provided is a method of treating cancer mediated by HDAC in a subject in need of such a treatment, comprising administering to the subject a therapeutically effective amount of at least one compound, or pharmaceutically acceptable salt thereof, described herein. In some embodiments, the cancer is chosen from lymphoma, pancreatic cancer, colorectal cancer, hepatocellular carcinoma, Waldenstrom macroglobulinemia, hormone refractory cancer of the prostate, and leukaemia, breast cancer, lung cancer, ovarian cancer, prostate cancer, head and neck cancer, renal cancer, gastric cancer, brain cancer, B-cell lymphoma, peripheral T-cell lymphoma, and cutaneous T-cell lymphoma. In some further embodiments, the cancer is chosen from the following cancer types. Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma, cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma; and the sensitization of tumors to radiotherapy by administering the compound according to the invention before, during or after irradiation of the tumor for treating cancer.

In some embodiments, the condition or disorder mediated by HDAC comprises a condition or disorder treatable by immune modulation. Accordingly, also provided is a method of treating a condition or disorder treatable by immune modulation mediated by HDAC in a subject in need of such a treatment, comprising administering to the subject a therapeutically effective amount of at least one compound, or pharmaceutically acceptable salt thereof, described herein. In some embodiments, the condition or disorder treatable by immune modulation is chosen from asthma, irritable bowel syndrome, Crohn's disease, ulcerative colitis, bowel motility disorders, hypertension, rheumatoid arthritis, osteoarthritis, juvenile chronic arthritis, graft versus host disease, psoriasis, spondyloarthropathy, inflammatory bowel disease, alcoholic hepatitis, Sjogren's syndrome, ankylosing spondylitis, membranous glomerulopathy, discogenic pain, systemic lupus erythematosus, allergic bowel disease, coeliac disease, bronchitis, cystic fibrosis, rheumatoid spondylitis, osteoarthritis, uveitis, intis, and conjunctivitis, ischemic bowel disease, psoriasis, eczema, dermatitis, septic arthritis, gout, pseudogout, juvenile arthritis, Still's disease, Henoch-Schonlein purpura, psoriatic arthritis, myalgia, reactive arthritis (Reiter's syndrome), hemochromatosis, Wegener's granulomatosis, familial Mediterranean fever (FMF), HBDS (hyperimmunoglobulinemia D and periodic fever syndrome), TRAPS (TNF-alpha receptor associated periodic fever syndrome), chronic obstructive pulmonary disease, neonatal-onset multisystem inflammatory disease (NOMID), cryopyrin-associated periodic syndrome (CAPS), and familial cold autoinflammatory syndrome (FCAS).

In some embodiments, the condition or disorder mediated by HDAC comprises an allergic disease. Accordingly, also provided is a method of treating an allergic disease, mediated by HDAC in a subject in need of such a treatment, comprising administering to the subject a therapeutically effective amount of at least one compound, or pharmaceutically acceptable salt thereof, described herein. Allergic diseases include, but are not limited to, respiratory allergic diseases such as allergic rhinitis, hypersensitivity lung diseases, hypersensitivity pneumonitis, eosinophilic pneumonias, Loeffler's syndrome, chronic eosinophilic pneumonia, delayed-type hypersensitivity, interstitial lung diseases (ILD), idiopathic pulmonary fibrosis, polymyositis, dermatomyositis, systemic anaphylaxis, drug allergies (e.g., to penicillin or cephalosporins), and insect sting allergies.

In some embodiments, the condition or disorder mediated by HDAC comprises an infectious disease such as a fungal infection, bacterial infection, viral infection, and protozoal infection, e.g., malaria, giardiasis, leishmaniasis, Chaga's disease, dysentery, toxoplasmosis, and coccidiosis. In some embodiments, the condition or disorder mediated by HDAC comprises malaria. Accordingly, also provided is a method of treating an infectious disease, such as malaria, mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises autism or Rett syndrome. Accordingly, also provided is a method of treating autism or Rett syndrome mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a hematological disorder such as thalassemia, anemia, and sickle cell anemia. Accordingly, also provided is a method of treating a hematological disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a metabolic disease such as prediabetes or diabetes (type I or II). Accordingly, also provided is a method of treating a metabolic disease, such as prediabetes or diabetes (type I or II), mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder that may also be treated by progenitor/stem cell based therapies such as: disorders related to diabetes (organ failure, cerrosis, and hepatitis); central nervous system (CNS) disorders associated with dysregulation of progenitor cells in the brain (e.g., post-traumatic stress disorder (PTSD); tumors (e.g., retinoblastomas); disorders affecting oligodendrycoyte progenitor cells (e.g., astrocytomas and ependimal cell tumors); multiple sclerosis; demyelinating disorders such as the leukodystrophies; neuropathies associated with white matter loss; and cerebellar disorders such as ataxia; and olfactory progenitor disorders (e.g., anosmic conditions). Accordingly, also provided is a method of treating a disorder that is mediated by HDAC in a subject in need of such a treatment, comprising administering to the subject a therapeutically effective amount of at least one compound, or pharmaceutically acceptable salt thereof, described herein, either before, during, or after a treatment with progenitor/stem cell based therapies.

In some embodiments, the condition or disorder mediated by HDAC comprises a disorder related to the proliferation of epithelial and mesenchymal cells (e.g., tumors, wound healing, and surgeries). Accordingly, also provided is a method of treating a disorder related to the proliferation of epithelial and mesenchymal cells that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder related to the proliferation of bone progenitors (e.g., osteoblasts and osteoclasts), disorders related to hair and epidermal progenitors (e.g., hair loss, cutaneous tumors, skin regeneration, burns, and cosmetic surgery); and disorders related to bone loss during menopause. Accordingly, also provided is a method of treating disorders related to the proliferation of bone progenitors, disorders related to hair and epidermal progenitors, or disorders related to bone loss that are mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC is a viral disorder for which blood cells become sensitized to other treatments after HDAC inhibition, following administering to the subject a therapeutically effective amount of at least one compound, or pharmaceutically acceptable salt thereof, as described herein.

In some embodiments, the condition or disorder mediated by HDAC is an immune disorder that may be co-treated with TNFα or other immune modulators, upon administering to the subject a therapeutically effective amount of at least one compound, or pharmaceutically acceptable salt thereof, as described herein.

In some embodiments, the condition or disorder mediated by HDAC comprises a graft rejection or transplant rejection. Accordingly, also provided is a method of treating a disorder related to a graft rejection or a transplant rejection that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a blood pressure disorder related to nitric oxide (NO) regulation (e.g., hypertension, erectile dysfunction, asthma; and ocular disorders as glaucoma). Accordingly, also provided is a method of treating a blood pressure disorder related to nitric oxide (NO) regulation that is mediated by HDAC in a subject in need of such a treatment, comprising administering to the subject a therapeutically effective amount of at least one compound, or pharmaceutically acceptable salt thereof, described herein. In some embodiments, the condition or disorder is a cardiac hypertrophic disorder. Accordingly, also provided is a method of treating a cardiac hypertrophic disorder that is mediated by HDAC in a subject in need of such a treatment, comprising administering to the subject a therapeutically effective amount of at least one compound, or pharmaceutically acceptable salt thereof, described herein.

Also provided are methods of treatment in which at least one compound, or pharmaceutically acceptable salt thereof, described herein is the only active agent given to the subject and also includes methods of treatment in which at least one compound, or pharmaceutically acceptable salt thereof, described herein is given to the subject in combination with one or more additional active agents.

In general, the compounds, or pharmaceutically acceptable salts thereof, described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, such as once or twice a day.

In some embodiments, the compounds, or pharmaceutically acceptable salts thereof, described herein are administered as a pharmaceutical composition. Accordingly, provided are pharmaceutical compositions comprising at least one compound, or pharmaceutically acceptable salt thereof, described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound, or pharmaceutically acceptable salt thereof, is sufficient to provide a practical quantity of material for administration per unit dose of the compound, or pharmaceutically acceptable salt thereof.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound, or pharmaceutically acceptable salt thereof, described herein.

Effective concentrations of at least one compound, or pharmaceutically acceptable salt thereof, described herein are mixed with a suitable pharmaceutically acceptable vehicle. In instances in which the compound, or pharmaceutically acceptable salt thereof, exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a compound, or pharmaceutically acceptable salt thereof, described herein, the resulting mixture may be a solution, suspension, emulsion or the like. The form of the resulting mixture depends upon a number of factors, including the intended mode of administration and the solubility of the compound, or pharmaceutically acceptable salt thereof, in the chosen vehicle. The effective concentration sufficient for ameliorating the symptoms of the disease treated may be empirically determined.

The compounds, or pharmaceutically acceptable salts thereof, described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one compound, or pharmaceutically acceptable salt thereof, described herein. In some embodiments, oral pharmaceutical compositions contain at least 5% (weight %) of at least one compound, or pharmaceutically acceptable salt thereof, described herein. Some embodiments contain from 25% to 50% or from 5% to 75% of at least one compound, or pharmaceutically acceptable salt thereof, described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound, or pharmaceutically acceptable salt thereof, described herein can be incorporated into oral liquid preparations such as aqueous or oily suspensions, solutions, emulsions, syrups, or elixirs, for example. Moreover, pharmaceutical compositions containing these at least one compound, or pharmaceutically acceptable salt thereof, can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, Avicel RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound, or pharmaceutically acceptable salt thereof, is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compound, or pharmaceutically acceptable salt thereof, described herein may be administered parenterally in a sterile medium. Parenteral administration includes subcutaneous injections, intravenous, intramuscular, intrathecal injection or infusion techniques. The compound, or pharmaceutically acceptable salt thereof, described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compound, or pharmaceutically acceptable salt thereof, described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound, or pharmaceutically acceptable salt thereof, described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compound, or pharmaceutically acceptable salt thereof, described herein may also be formulated for transdermal administration as a transdermal patch.

Topical pharmaceutical compositions comprising at least one compound, or pharmaceutically acceptable salt thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compound, or pharmaceutically acceptable salt thereof, described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the compound, or pharmaceutically acceptable salt thereof, include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound, or pharmaceutically acceptable salt thereof, described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one compound, or pharmaceutically acceptable salt thereof, described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one compound, or pharmaceutically acceptable salt thereof, described herein, and instructions for using the composition to treat a subject (typically a human patient). In some embodiments, the instructions are for using the pharmaceutical composition to treat a subject suffering a condition or disorder mediated by HDAC. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound, or pharmaceutically acceptable salt thereof, can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one compound, or pharmaceutically acceptable salt thereof, described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one compound, or pharmaceutically acceptable salt thereof, described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for Alzheimer's disease, including treating memory and/or cognitive impairment associated with Alzheimer's disease, comprising administering to a subject, simultaneously or sequentially, at least one compound, or pharmaceutically acceptable salt thereof, described herein and one or more additional agents used in the treatment of Alzheimer's disease such as, but not limited to, Reminyl, Cognex, Aricept, Exelon, Akatinol, Neotropin, Eldepryl, Estrogen and Clioquinol. In methods using simultaneous administration, the agents can be present in a combined composition or can be administered separately. Also provided are pharmaceutical compositions comprising at least one compound, or pharmaceutically acceptable salt thereof, described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Clioquinol. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Clioquinol.

Also provided are methods for treating cancer comprising administering to a subject, simultaneously or sequentially, at least one compound, or pharmaceutically acceptable salt thereof, described herein and one or more additional agents used in the treatment of cancer such as, but not limited to, the following categories of anti-tumor agents (i) other cell cycle inhibitory agents that work by the same or different mechanisms from those defined hereinbefore, for example cyclin dependent kinase (CDK) inhibitors, in particular CDK2 inhibitors;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5.alpha.-dihydroreductase (for example finasteride), anti-invasion agents (for example metalloproteinase inhibitors like marimastat and inhibitors of urokinase plasminogen activator receptor function) and inhibitors of growth factor function, (such growth factors include for example vascular endothelial growth factor, epithelial growth factor, platelet derived growth factor and hepatocyte growth factor such inhibitors include growth factor antibodies, growth factor receptor antibodies, tyrosine kinase inhibitors and serine/threonine kinase inhibitors);

(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan);

(iv) antiangiogenic agents that work by different mechanisms from those defined hereinbefore (for example receptor tyrosine kinases like Tie-2, inhibitors of integrin .alpha.v-.beta.3 function, angiostatin, razoxin, thalidomide), and including vascular targeting agents; and (v) differentiation agents (for example retinoic acid and vitamin D).

In methods using simultaneous administration, the agents can be present in a combined composition or can be administered separately. Also provided are pharmaceutical compositions comprising at least one compound, or pharmaceutically acceptable salt thereof, described herein, and one or more anti-tumor agent as described herein. Similarly, also provided are packaged pharmaceutical compositions containing a pharmaceutical composition comprising at least one compound, or pharmaceutically acceptable salt thereof, described herein, and another composition comprising one or more one or more anti-tumor agent as described herein. When used in combination with one or more additional pharmaceutical agent or agents, the described herein may be administered prior to, concurrently with, or following administration of the additional pharmaceutical agent or agents.

In some embodiments, the compounds, or pharmaceutically acceptable salts thereof, described herein, are administered in conjunction with surgery or radiotherapy, optionally in combination with one or more additional agents used in the treatment of cancer.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compound, or pharmaceutically acceptable salt thereof, described herein is typically administered at dosage levels and in a manner customary for HDAC inhibitors. For example, the compound, or pharmaceutically acceptable salt thereof, can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one compound, or pharmaceutically acceptable salt thereof, described herein, for example, 0.1-50 mg of at least one compound, or pharmaceutically acceptable salt thereof, described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one compound, or pharmaceutically acceptable salt thereof, described herein.

A labeled form of a compound, or pharmaceutically acceptable salt thereof, described herein can be used as a diagnostic for identifying and/or obtaining compounds that have the function of modulating an activity of HDAC as described herein. The compound, or pharmaceutically acceptable salt thereof, described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The compounds, or pharmaceutically acceptable salts thereof, compositions, and methods described herein are further illustrated by the following non-limiting examples.

Abbreviations aq.: Aqueous

DCM: Dichloromethane

DCE: Dichloroethane

DIPEA: Diisopropylethylamine

DME: Dimethoxyethane

DMF: Dimethylformamide

DMSO: Dimethylsulfoxide ee: Enantiomeric excess

ES+: Electrospray Positive Ionization

ES−: Electrospray Negative Ionization $Et_2O$: Diethyl ether

EtOAc: Ethyl acetate h: Hour

HPLC: High Performance Liquid Chromatography

LCMS: Liquid Chromatography Mass Spectrometry

LiHMDS: Lithium bis(trimethylsilyl)amide

M: Mass

MeCN: Acetonitrile

MeOH: Methanol

NaHMDS Sodium bis(trimethylsilyl)amide

NMP: N-Methyl pyrrolidinone o-tolyl: 2-Methylphenyl

Pd/C: Palladium on carbon $Pd_2(dba)_3$: Tris(dibenzylideneacetone)dipalladium(O)

$Pd(dppf)Cl_2$: [1,1′-Bis(diphenylphosphino)ferrocene]dichloropalladium(II) complex with DCM $Pd(PPh_3)_4$: Tetrakis(triphenylphosphine)palladium(O)

RT: Retention time r.t.: Room temperature sat.: Saturated

TFFH: Tetramethylfluoroformamidinium hexafluorophosphate

THF: Tetrahydrofuran

TM: Target material

Xantphos: 4,5-Bis(diphenylphosphino)-9,9-dimethylxanthene

Analytical Conditions

| Analytical Condition | Method | Description | | |
|---|---|---|---|---|
| 10 cm_ESI_Formic_MeCN, 10 cm_ESCI_Formic_MeCN | 1 | Solvents: | Acetonitrile (far UV grade) with 0.1% (v/v) formic acid. Water (high purity via PureLab Option unit) with 0.1% formic acid | |
| | | Column: | Phenomenex Luna 5 µm C18 (2), 100 × 4.6 mm (Plus guard cartridge) | |
| | | Flow Rate: | 2 mL/min | |
| | | gradient: | A: Water/formic acid B: MeCN/formic acid | |
| | | Time | A % | B % |
| | | 0.00 | 95 | 5 |
| | | 3.50 | 5 | 95 |
| | | 5.50 | 5 | 95 |
| | | 5.60 | 95 | 5 |
| | | 6.50 | 95 | 5 |
| | | Typical Injections 2-7 µL (concentration~0.2-1.0 mg/mL) | | |
| 15 cm_Formic_Ascentis_HPLC_MeCN | 2 | Solvents: | Acetonitrile (Far UV grade) with 0.1% (v/v) formic acid. Water (High purity via PureLab Ultra unit) with 0.1% formic acid | |
| | | Column: | Supelco, Ascentis ® Express C18 or Hichrom Halo C18, 2.7 µm C18, 150 × 4.6 mm. | |
| | | Flow Rate: | 1 mL/min | |
| | | Gradient: | A: Water/formic B: MeCN/formic | |
| | | Time | A % | B % |
| | | 0.00 | 96 | 4 |
| | | 3.00 | 96 | 4 |
| | | 9.00 | 0 | 100 |
| | | 13.6 | 0 | 100 |
| | | 13.7 | 96 | 4 |
| | | 15 | 96 | 4 |
| | | Typical Injections 2-7 µL (concentration~0.2-1 mg/mL) | | |
| 10 cm_Formic_ACE-AR_HPLC_CH3CN, 10 cm_Formic_ACE 3 C18 AR_HPLC_CH3CN | 3 | Solvents: | Acetonitrile (far UV grade) with 0.1% (v/v) formic acid. Water (high purity via PureLab Ultra unit) with 0.1% formic acid | |
| | | Column: | Hichrom ACE 3 C18-AR mixed mode column 100 × 4.6 mm | |
| | | Flow Rate: | 1 mL/min | |
| | | gradient: | A: Water/formic acid B: MeCN/formic acid | |
| | | Time | A % | B % |
| | | 0.00 | 98 | 2 |
| | | 3.00 | 98 | 2 |
| | | 12.00 | 0 | 100 |
| | | 15.4 | 0 | 100 |
| | | 15.5 | 98 | 2 |
| | | 17 | 98 | 2 |
| | | Typical injections 0.2-10 µL | | |

Compounds were named with the aid of the Cambridge-Soft Chemistry Cartridge (v. 12.0.3.1212) software.

All reactions involving air- or moisture-sensitive reagents were performed under a nitrogen atmosphere using dried solvents and glassware.

Preparation of Intermediates

Preparation of Intermediate 1: (S)-methyl 1-(3-fluoro-2-methylphenyl)-3-oxocyclopentane-carboxylate Method 1

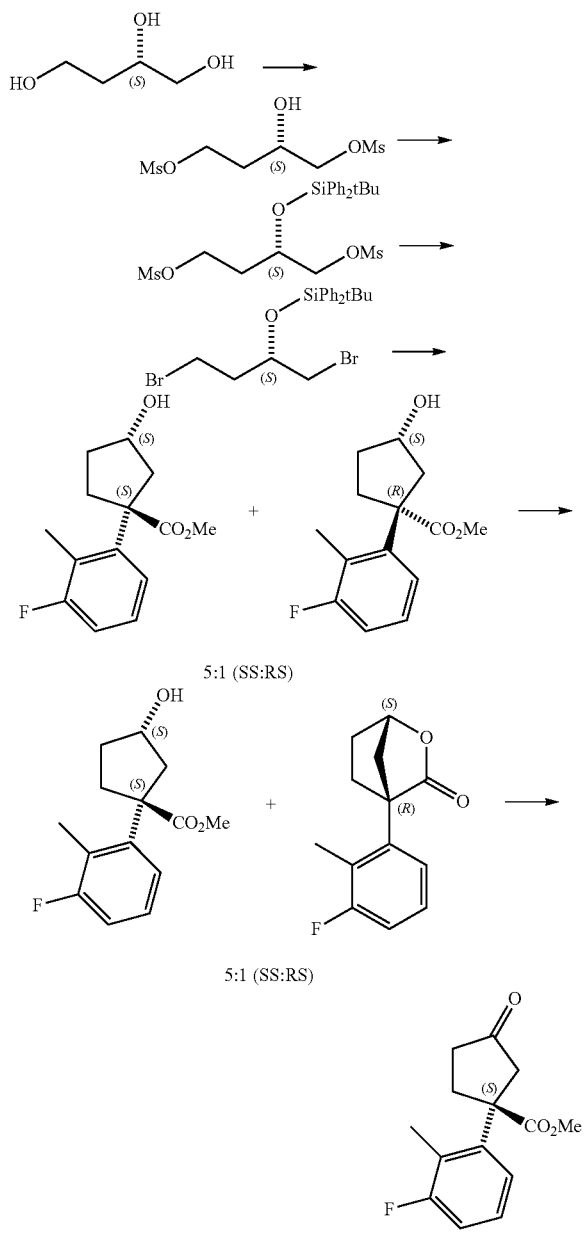

Step 1: (S)-2-hydroxybutane-1,4-diyl dimethanesulfonate (S)-butane-1,2,4-triol (20.0 g, 0.19 mol) was dissolved in anhydrous pyridine (85 mL). The reaction mixture was rapidly stirred whilst being cooled to −10° C. (NaCl/ice bath). Methanesulfonyl chloride (44.3 g, 30 mL, 0.40 mol) was then added drop-wise whilst maintaining internal flask temperature at <4° C. (~3 h). Once addition was complete the reaction mixture was stirred at r.t. for a further 1 h. After this time reaction was cooled to 4° C. and 2 M aq. HCl (200 mL) was added over 20 min. The resulting solution was partitioned with EtOAc (300 mL), washed with further 2 M aq. HCl (200 mL), dried, filtered (phase separation cartridge) and concentrated to give a yellow oil which partially solidified on standing. The residue was dissolved in the minimum hot ethyl acetate and left to stand at −20° C. for 16 h. Precipitated solids were filtered and washed with cold $Et_2O$/iso-hexane (1:9, 50 mL) to give the title compound as colorless crystals (26.8 g, 55%). [Purification can also be achieved via flash silica column chromatography (diethyl ether to EtOAc)—this gives a close running impurity which can be easily separated at the next step.] $R_f$=0.2 (66% EtOAc/iso-hexane); MS (ES+) consistent with target $(M+H)^+$; $^1H$ NMR δ (ppm): (DMSO-$d_6$): 5.33 (1H, s), 4.35-4.23 (2H, m), 4.19-3.99 (2H, m), 3.89-3.81 (1H, m), 3.19 (3H, s), 3.18 (3H, s), 1.94-1.84 (1H, m), 1.77-1.66 (1H, m).

Step 2: (S)-2-((tert-butyldiphenylsilyl)oxy)butane-1,4-diyl Dimethanesulfonate

To a 4° C. solution of (S)-2-hydroxybutane-1,4-diyl dimethanesulfonate (23.2 g, 0.09 mol) in anhydrous DMF (75 mL) was added tert-butylchlorodiphenylsilane (36.5 g, 34.5 mL, 0.11 mol) followed by imidazole (10.0 g, 0.15 mol). The reaction mixture was stirred at 4° C. for 1 h then at r.t. for a further 16 h. The reaction mixture was quenched using ice water (200 mL) with rapid stirring for 30 min. The corresponding solution was partitioned with EtOAc (300 mL), washed with water (2×200 mL), and then sat. NaCl solution (250 mL). The combined organic layers were dried, filtered (phase separation cartridge) and concentrated to give a yellow oil. Purification by flash silica column chromatography (gradient elution iso-hexane to 50% EtOAc in iso-hexane) gave the title compound as a colorless glass (42.0 g, 93%). $R_f$=0.55 (66% EtOAc/iso-hexane); MS (ES+) consistent with target $(M+H)^+$; $^1H$ NMR δ (ppm) (DMSO-$d_6$): 7.67-7.63 (4H, m), 7.52-7.41 (6H, m), 4.31-4.16 (2H, m), 4.13-4.01 (3H, m), 3.08 (3H, s), 3.02 (3H, s), 1.92 (2H, dd, J=12.2, 6.1 Hz), 1.02 (9H, s).

Step 3: (S)-tert-butyl((1,4-dibromobutan-2-yl)oxy) diphenylsilane

To a solution of (S)-2-((tert-butyldiphenylsilyl)oxy)butane-1,4-diyl dimethanesulfonate (42.0 g, 0.08 mol) in anhydrous DMF (320 mL) was added lithium bromide (22.0 g, 0.25 mol). The reaction mixture was stirred at 105° C. for 1.5 h. The reaction mixture was cooled to r.t. and partitioned between EtOAc (500 mL) and water (300 mL). Organic layers were washed with further water (2×300 mL) and sat. aq. NaCl solution (400 mL). The combined organic layers were dried, filtered (phase separation cartridge) and concentrated to give a yellow oil. Purification by flash silica column chromatography (gradient elution iso-hexane to 10% EtOAc in iso-hexane) gave the title compound as a colorless oil which darkens upon standing (30.0 g, 80%). $R_f$=0.80 (60% EtOAc/iso-hexane); MS (ES+) consistent with target $(M+H)^+$; $^1H$ NMR δ (ppm) (DMSO-$d_6$): 7.69-7.63 (4H, m), 7.52-7.41 (6H, m), 4.07-3.99 (1H, m), 3.53-3.40 (4H, m), 2.10 (2H, dd, J=13.0, 6.5 Hz), 1.04 (9H, s).

Step 4: (3S)-methyl 1-(3-fluoro-2-methylphenyl)-3-hydroxycyclopentanecarboxylate To a solution of (S)-tert-butyl((1,4-dibromobutan-2-yl)oxy)diphenylsilane (6.43 g, 0.014 mol) and methyl 2-(3-fluoro-2-methylphenyl)acetate (2.0 g, 0.011 mol) in anhydrous DMF (80 mL) was added 18-crown-6 (0.2 g, catalytic). The reaction mixture was stirred at r.t. for 10 min then sodium hydride (60% dispersion in mineral oil 1.05 g, 0.03 mol) was added portion-wise over 1.5 h. Reaction mixture was stirred at r.t. for a further 16 h. The reaction mixture was cooled to 4° C. and quenched by drop-wise addition of 5% NaH$_2$PO$_4$ solution (15 mL). The solution was then partitioned between EtOAc (250 mL) and water (200 mL). The organic layer was washed with further water (2×150 mL), sat. NaCl solution (200 mL), then dried, filtered (phase separation cartridge) and concentrated to give a yellow oil. The resultant oil was dissolved in anhydrous THF (80 mL) and TBAF (1M in THF, 0.03 mol, 30 mL) was added. Reaction mixture was then stirred at r.t. for 3 h. After this time the reaction mixture was concentrated under reduced pressure and purified by flash silica column chromatography (gradient elution iso-hexane to 33% EtOAc in iso-hexane) to give the title compound as a colorless oil (2.10 g, 78%, 5:1 mixture of isomers). R$_f$=0.1 (20% EtOAc/iso-hexane); MS (ES+) consistent with target (M+H)$^+$.

Step 5: lactonization to (1S,4R)-4-(3-fluoro-2-methylphenyl)-2-oxabicyclo[2.2.1]heptan-3-one To a solution of (1S,3S)-methyl 1-(3-fluoro-2-methylphenyl)-3-hydroxycyclopentanecarboxylate (5:1 (1S, 3S):(1R:3S) mixture of isomers, 2.10 g, 0.0086 mol) in anhydrous acetonitrile (100 mL) was added DBU (1.44 g, 1.42 mL, 0.0095 mol). The reaction mixture was stirred at 80° C. for 20 h. The reaction mixture was cooled to r.t. and partitioned between CH$_2$Cl$_2$ (125 mL) and 1 M HCl (100 mL). Organic layers were extracted, washed with water (100 mL), then dried, filtered (phase separation cartridge) and concentrated to give a yellow oil. The residue was purified by flash silica column chromatography (gradient elution iso-hexane to 40% EtOAc in iso-hexane) to give the title compound (1S,4R)-4-(3-fluoro-2-methylphenyl)-2-oxabicyclo[2.2.1]heptan-3-one as a colorless oil (256 mg); R$_f$=0.3 (33% EtOAc/iso-hexane); MS (ES+) consistent with target (M+H)$^+$; $^1$H NMR δ (ppm) (CDCl$_3$): 7.18-7.10 (1H, m), 7.09-6.98 (2H, m), 5.00 (1H, d, J=2.1 Hz), 2.81 (1H, dd, J=10.4, 2.4 Hz), 2.39-2.32 (1H, m), 2.32 (3H, d, J=2.8 Hz), 2.30-2.21 (1H, m), 2.15-2.07 (2H, m), 1.93 (1H, d, J=10.3 Hz); $^{19}$F NMR: −114.43; and unreacted starting material (1S,3S)-methyl 1-(3-fluoro-2-methylphenyl)-3-hydroxycyclopentanecarboxylate as a colorless oil (1.63 g); R$_f$=0.15 (33% EtOAc/iso-hexane); MS (ES+) consistent with target (M+H)$^+$; $^1$H NMR δ (ppm) (CDCl$_3$): 7.24 (1H, d, J=8.03 Hz), 7.19-7.11 (1H, m), 6.97-6.90 (1H, m), 4.56-4.49 (1H, m), 3.62 (3H, s), 3.07 (1H, dd, J=13.8, 6.6 Hz), 2.47-2.42 (2H, m), 2.11 (3H, d, J=2.8 Hz), 2.10-2.01 (1H, m), 1.92 (1H, ddd, J=13.9, 4.5, 1.1 Hz), 1.79-1.70 (1H, m), 1.38 (1H, d, J=4.2 Hz); $^{19}$F NMR: −114.83.

Step 6: (S)-methyl 1-(3-fluoro-2-methylphenyl)-3-oxocyclopentanecarboxylate (Intermediate 1)

To a solution of (1S,3S)-methyl 1-(3-fluoro-2-methylphenyl)-3-hydroxycyclopentanecarboxylate (1.60 g, 6.5 mmol) in anhydrous dichloromethane (100 mL) was added Dess-Martin Periodinane (3.32 g, 7.8 mmol). The reaction mixture was stirred at r.t. for 4 h. Reaction mixture was quenched with a mixture of 10% Na$_2$S$_2$O$_3$ and sat. NaHCO$_3$ solution (1:1, 100 mL) and then rapidly stirred for 30 min. Organic layers were extracted with further CH$_2$Cl$_2$ (2×50 mL), then dried, filtered (phase separation cartridge) and concentrated to give a pale yellow oil. The residue was purified by flash silica column chromatography (gradient elution iso-hexane to 20% EtOAc in iso-hexane) to give the title compound as a colorless solid (1.42 g, 84%). R$_f$=0.25 (33% EtOAc/iso-hexane); $^1$H NMR δ (ppm) (CDCl$_3$): 7.28-7.19 (1H, m), 7.17-7.02 (2H, m), 3.76 (3H, s), 3.28 (1H, d, J=17.9 Hz), 2.88-2.79 (1H, m), 2.69-2.33 (4H, m), 2.19 (3H, d, J=2.7 Hz); SFC (Analytical) (CHIRALPAK IA 5/95 IPA/CO$_2$, 5.0 ml/min, 120 bar, 40° C.) RT 2.1 min (>99.5% ee); Chiral HPLC (Chiralpak IC 10/90 IPA/MeOH (50/50/0.1% formic acid)/heptane, 1.0 ml/min) RT 9.48 min.

Preparation of Intermediate 2: (R)-methyl 1-(3-fluoro-2-methylphenyl)-3-oxocyclopentane-carboxylate Method 2

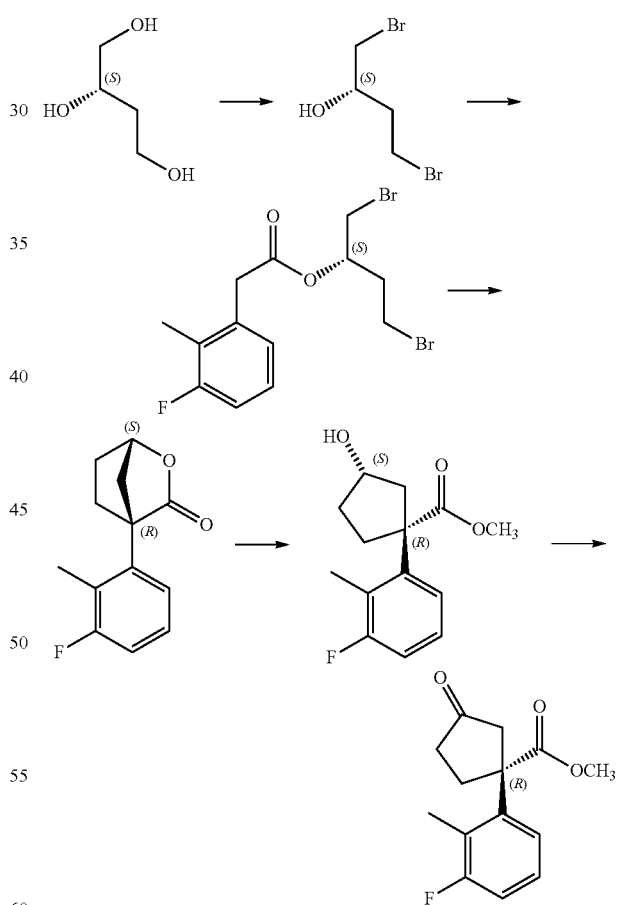

Step 1: (S)-1,4-dibromobutan-2-ol

To a stirred solution of (S)-butane-1,2,4-triol (2 g, 18.9 mmol) and triphenylphosphine (9.9 g, 37.7 mmol) in DCM (100 mL) at 0° C. was added N-bromosuccinimide (6.7 g, 37.7 mmol) portionwise. The mixture was allowed to warm to r.t. and stirred for 17 h. The reaction mixture was washed with water (2×100 mL) and sat. brine solution (100 mL) and the organics passed through a phase separator before concentrating in vacuo. The residue was dissolved in DCM (10 mL) and added to rapidly stirred Et$_2$O (200 mL). The resulting solid was removed by vacuum filtration. Additional solid precipitated in the filtrate during filtration, so this process was repeated several times to remove residual triphenylphosphine oxide. The filtrate was concentrated and the resulting oil purified by flash silica column chromatography (gradient elution 5% EtOAc in iso-hexane to 10% EtOAc in iso-hexane) to give the title compound as a colorless oil (1.5 g, 35%). $^1$H NMR δ (ppm) (CDCl$_3$): 4.09-4.01 (1H, m), 3.61-3.50 (3H, m), 3.42 (1H, dd, J=10.4, 6.7 Hz), 2.18 (1H, dd, J=5.4, 0.8 Hz), 2.13-2.01 (2H, m).

Step 2: (S)-1,4-dibromobutan-2-yl 2-(3-fluoro-2-methylphenyl)acetate

To a stirred solution of (S)-1,4-dibromobutan-2-ol (1.43 g, 6.16 mmol) in DCM (30 mL) was added 2-(3-fluoro-2-methylphenyl)acetic acid (941 mg, 5.60 mmol), dicyclohexylcarbodiimide (1.27 g, 6.16 mmol) and DMAP (20 mg, catalytic) and the mixture stirred at r.t. for 17 h. The reaction was filtered and a white solid was removed by filtration and washed with DCM (3×25 mL). The filtrate was collected and washed with 1 M HCl$_{(aq)}$ (30 mL), sat. brine solution (30 mL) and the organics passed through a phase separator and concentrated. Purification by flash silica chromatography (gradient elution iso-hexane to 20% EtOAc in iso-hexane) gave the title compound as a white crystalline solid (2.06 g, 96%). $^1$H NMR δ (ppm) (CDCl$_3$): 7.15-7.07 (1H, m), 7.02-6.93 (2H, m), 5.20-5.12 (1H, m), 3.70 (2H, s), 3.58 (1H, dd, J=11.1, 4.7 Hz), 3.45 (1H, dd, J=11.1, 4.3 Hz), 3.34 (1H, ddd, J=10.3, 6.6, 5.5 Hz), 3.25 (1H, ddd, J=10.3, 8.4, 6.1 Hz), 2.35-2.26 (1H, m), 2.24 (3H, d, J=2.7 Hz), 2.26-2.12 (1H, m).

Step 3: (1S,4R)-4-(3-fluoro-2-methylphenyl)-2-oxabicyclo[2.2.1]heptan-3-one

To a stirred solution of (S)-1,4-dibromobutan-2-yl 2-(3-fluoro-2-methylphenyl)acetate (2.05 g, 5.37 mmol) in 1,4-dioxane (50 mL) at r.t., was added LiHMDS (11.8 mL, 11.8 mmol, 1 M in THF) at a rate of 1 mL/min. After complete addition, the mixture was stirred for 1 h and quenched with 1 M HCl$_{(aq)}$ (20 mL) and then extracted into EtOAc (3×50 mL). The combined organics were washed with water (50 mL) and sat. brine solution (50 mL), separated, dried (MgSO$_4$), filtered and concentrated. Purification by flash silica chromatography (gradient elution iso-hexane to 5% EtOAc in iso-hexane) gave the title compound as a white crystalline solid (890 mg, 75%). $^1$H NMR δ (ppm) (CDCl$_3$): 7.17-7.08 (1H, m), 7.07-6.97 (2H, m), 5.00 (1H, d, J=2.10 Hz), 2.81 (1H, dd, J=10.4, 2.4 Hz), 2.40-2.18 (2H, m), 2.30 (3H, d, 2.3 Hz), 2.13-2.07 (2H, m), 1.93 (1H, d, J=10.3 Hz).

Step 4: (1R,3S)-methyl-1-(3-fluoro-2-methylphenyl)-3-hydroxycyclopentanecarboxylate To a stirred solution of (1R,4S)-4-(3-fluoro-2-methylphenyl)-2-oxabicyclo[2.2.1]heptan-3-one (890 mg, 4.05 mmol) in MeOH (30 mL) was added 4 M HCl in dioxane (1 mL). The mixture was heated to 60° C. for 17 h and then concentrated. Purification by flash silica chromatography (gradient elution iso-hexane to 30% EtOAc in iso-hexane) gave the title compound as a white crystalline solid (766 mg, 75% [95% based on recovered starting material]). $^1$H NMR δ (ppm) (CDCl$_3$): 7.18-7.06 (2H, m), 6.98-6.89 (1H, m), 4.42-4.37 (1H, m), 3.66 (3H, s), 2.74-2.69 (1H, m), 2.66-2.58 (1H, m), 2.55 (1H, d, J=7.85 Hz), 2.29-2.13 (3H, m), 2.13 (3H, d, J=2.7 Hz), 1.83-1.72 (1H, m).

Step 5: (R)-methyl-1-(3-fluoro-2-methylphenyl)-3-oxocyclopentanecarboxylate (Intermediate 2)

To a solution of (1S,3R)-methyl-1-(3-fluoro-2-methylphenyl)-3-hydroxycyclopentanecarboxylate (766 mg, 3.04 mmol) in anhydrous dichloromethane (20 mL) was added Dess-Martin Periodinane (1.55 g, 3.64 mmol). The reaction mixture was stirred at r.t. for 4 h. Reaction mixture was quenched with a mixture of 10% Na$_2$S$_2$O$_3$ and sat. NaHCO$_3$ solution (1:1, 50 mL) and then rapidly stirred for 30 min. Organic layers were extracted with further CH$_2$Cl$_2$ (2×50 mL), then dried, filtered (phase separation cartridge) and concentrated to give a pale yellow oil. The residue was purified by flash silica column chromatography (gradient elution iso-hexane to 20% EtOAc in iso-hexane) to give the title compound as a colorless solid (656 mg, 86%). $^1$H NMR δ (ppm) (CDCl$_3$): 7.28-7.19 (1H, m), 7.17-7.02 (2H, m), 3.76 (3H, s), 3.23 (1H, d, J=17.9 Hz), 2.88-2.79 (1H, m), 2.69-2.33 (4H, m), 2.19 (3H, d, J=2.7 Hz). SFC (Analytical) (CHIRALPAK IA 5/95 IPA/CO$_2$, 5.0 mL/min, 120 bar, 40° C.) RT 2.4 min; Chiral HPLC (Chiralpak IC 10/90 IPA/MeOH (50/50/0.1% formic acid)/heptane, 1.0 mL/min) RT 10.35 min (95.7% ee).

Step 6: Recrystallization of Intermediate 2

Intermediate 2 (1.8 g, Chiral HPLC: (Chiralpak IC 10/90 IPA/MeOH (50/50/0.1% formic acid)/heptane, 1.0 mL/min) 97.4% ee) was dissolved in minimum hot heptane and the solution allowed to cool. Crystals formed and the supernatant was decanted using a pipette. The process was repeated. The solid crystals were dried in vacuo to give the title compound (1.5 g). Chiral HPLC (Chiralpak IC 10/90 IPA/MeOH (50/50/0.1% formic acid)/heptane, 1.0 mL/min)>99.5% ee).

Preparation of Intermediate 3: (±)-methyl 1-(3-fluoro-2-methylphenyl)-3-oxocyclopentane Carboxylate Prepared from (±)-butane-1,2,4-triol following the procedures described in Method 1 for the preparation of Intermediate 1 but omitting the DBU mediated lactonization step (step 5). LCMS (ES+) 251 (M+H)$^+$, RT 3.80 min (Analytical method 1); $^1$H NMR δ (ppm) (CDCl$_3$): 7.28-7.19 (1H, m), 7.17-7.02 (2H, m), 3.76 (3H, s), 3.28 (1H, d, J=17.9 Hz), 2.88-2.79 (1H, m), 2.69-2.33 (4H, m), 2.19 (3H, d, J=2.7 Hz).

Preparation of Intermediate 4: (S)-methyl 1-phenyl-3-(((trifluoromethyl)sulfonyl)oxy)cyclopent-2-enecarboxylate Intermediate 4

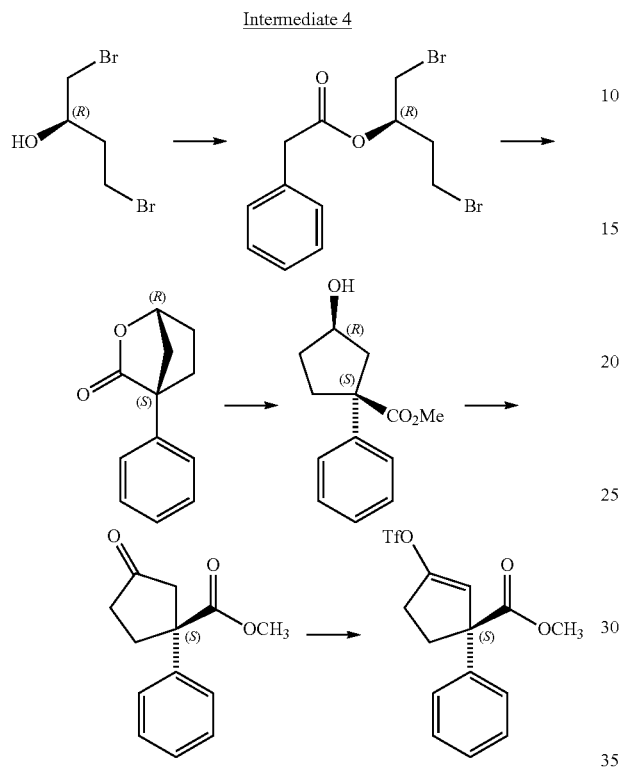

(R)-1,4-Dibromobutan-2-yl 2-phenyl Acetate

To a stirred solution of (R)-1,4-dibromobutan-2-ol (2.70 g, 11.6 mmol), prepared following step 1 of Method 2 using (R)-butane-1,2,4-triol in place of (S)-butane-1,2,4-triol, in DCM (50 mL) was added phenylacetic acid (1.44 g, 10.6 mmol), dicyclohexylcarbodiimide (2.18 g, 10.6 mmol) and DMAP (20 mg, catalytic) and the mixture stirred at r.t for 17 h. The white solid was filtered and washed with DCM (3×25 mL). The filtrate was collected and washed with 1 M HCl$_{(aq)}$ (30 mL), sat. brine solution (30 mL) and the organics passed through a phase separator and concentrated. Purification by flash silica chromatography (gradient elution i-hex to 20% EtOAc in i-hex) gave the title compound as a white crystalline solid (3.95 g, >99%).

(1R,4S)-4-Phenyl-2-oxabicyclo[2.2.1]heptan-3-one

To a stirred solution of (R)-1,4-dibromobutan-2-yl 2-phenyl acetate (3.54 g, 10.1 mmol) in 1,4-dioxane (150 mL) at r.t. was added LiHMDS (24 mL, 1 M in THF, 24 mmol) at a rate of 1 mL/min. After complete addition, the mixture was stirred for 1 h and quenched with 1 M HCl$_{(aq)}$ (20 mL) and then extracted into EtOAc (3×50 mL). The combined organics were washed with water (50 mL) and sat. brine solution (50 mL), separated, dried (MgSO$_4$), filtered and concentrated. Purification by flash silica chromatography (gradient elution, 0-30% EtOAc in iso-hexane) gave the title compound as a white crystalline solid (1.01 g, 53%).

(1S,3R)-Methyl 3-hydroxy-1-phenylcyclopentanecarboxylate

To a stirred solution of (1R,4S)-4-phenyl-2-oxabicyclo [2.2.1]heptan-3-one (1.01 g, 5.37 mmol) in MeOH (25 mL) was added 4 M HCl in dioxane (6 mL). The mixture was stirred at r.t for 17 h and then concentrated. Purification by flash silica chromatography (gradient elution, 0-35% EtOAc in iso-hexane) gave the title compound as a white crystalline solid (699 mg, 59%).

(S)-Methyl 3-oxo-1-phenylcyclopentanecarboxylate

To a solution of (1S,3R)-methyl 3-hydroxy-1-phenylcyclopentanecarboxylate (699 mg, 3.18 mmol) in dichloromethane (20 mL) was added Dess-Martin Periodinane (1.62 g, 3.81 mol). The reaction mixture was stirred at r.t. for 3 h. Reaction mixture was quenched with a mixture of 10% Na$_2$S$_2$O$_3$ and sat. aq. NaHCO$_3$ solution (1:1, 50 mL) and then rapidly stirred for 30 minutes. Organic layers were extracted with further CH$_2$Cl$_2$ (2×50 mL), then dried, filtered (phase separation cartridge) and concentrated to give a pale yellow oil. The residue was purified by flash silica column chromatography (gradient elution, 0-20% EtOAc in iso-hexane) to give the title compound as a colorless solid (656 mg, 86%).

(S)-Methyl 1-phenyl-3-(((trifluoromethyl)sulfonyl)oxy)cyclopent-2-enecarboxylate (Intermediate 4)

(S)-Methyl 3-oxo-1-phenylcyclopentanecarboxylate (630 mg, 2.89 mmol) and THF (25 mL) were combined under a nitrogen atmosphere and cooled with an ice bath. NaHMDS (1 M in THF) (5.2 mL, 5.2 mmol) was added dropwise followed after 20 minutes by N-(5-chloropyridin-2-yl)-1,1,1-trifluoro-N-((trifluoromethyl)sulfonyl)methanesulfonamide (1.59 g, 4.05 mmol). Reaction mixture was allowed to warm to room temperature and stirred for 3 hours. Reaction mixture was then diluted with CH$_2$Cl$_2$, washed with water, evaporated to dryness onto silica and purified by flash chromatography to give the title compound as a clear oil (590 mg, 58%).

Preparation of Examples

General Synthetic Methods

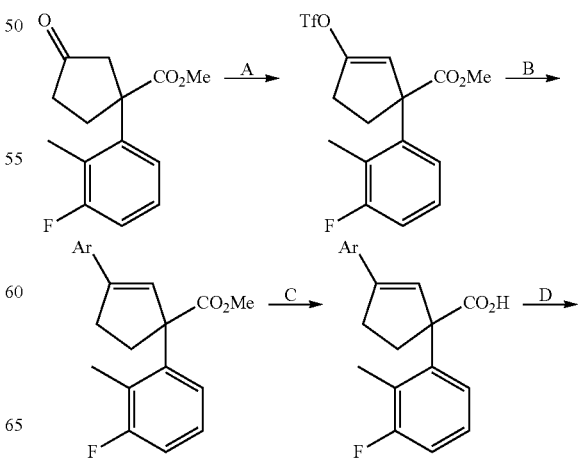

-continued

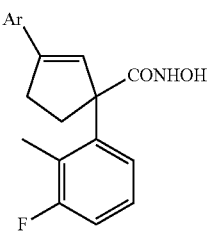

Method A (Vinyl Triflate Formation)

To a solution of methyl 1-(3-fluoro-2-methylphenyl)-3-oxocyclopentanecarboxylate (1.30 g, 5.20 mmol) in anhydrous THF (10 mL) was added drop-wise NaHMDS (1 M in THF, 5.80 mL, 5.80 mmol) at 0° C. The reaction mixture was stirred at 0° C. for 1 h. After this time N-phenylbistriflimide (2.23 g, 6.24 mmol) was added portionwise with 2 h additional stirring. The reaction mixture was quenched via addition of sat. NH$_4$Cl (5 mL) with rapid stirring for 10 min. The reaction mixture was partitioned between EtOAc (50 mL) and water (50 mL). Organic layers were extracted, washed with brine (50 mL), then dried, filtered using a phase separation cartridge and concentrated to give a yellow oil.

Comins' reagent (N,N-bis(trifluoromethylsulfonyl)-5-chloro-2-pyridylamine) may also be used in this method, in place of N-phenylbistriflimide.

Method B (Suzuki Coupling)

To a solution of methyl 1-(3-fluoro-2-methylphenyl)-3-(((trifluoromethyl)sulfonyl) oxy)cyclopent-2-enecarboxylate (0.5 g, 1.31 mmol) in 1,2 dimethoxyethane (8 mL) was added boronic acid (1.31 mmol), potassium carbonate (0.362 g, 2.62 mmol) and water (4 mL). The reaction mixture was heated to 60° C. after which time a colorless solution formed. [1,1'-Bis(diphenylphosphino)ferrocene]dichloropalladium(II), complex with dichloromethane (0.06 g, 0.07 mmol) was added and the reaction mixture was heated to 80° C. under N$_2$ for 2 h. After this time the reaction mixture was cooled to r.t. and filtered through Celite, washing with EtOAc (3×10 mL). Combined organics were extracted with water (15 mL) then brine (20 mL). EtOAc layers were then dried, filtered (phase separation cartridge) and concentrated.

Method B (ii) (Suzuki Coupling)

To a solution of methyl-1-(3-fluoro-2-methylphenyl)-3-(((trifluoromethyl)sulfonyl) oxy)cyclopent-2-enecarboxylate (0.2 g, 0.5 mmol) in 1,2 dimethoxyethane (8 mL) was added bis(pinacolato)diboron (0.15 g, 0.6 mmol), potassium acetate (0.060 g, 0.6 mmol), [1,1'-Bis(diphenylphosphino) ferrocene]dichloropalladium(II), complex with dichloromethane (0.03 g, 0.02 mmol) and water (2 mL). The reaction mixture was heated to 80° C. under N$_2$ for 2 h. After this time the reaction mixture was cooled to r.t. and aryl bromide (0.57 mmol), potassium carbonate (0.036 g, 1.31 mmol) and tetrakis(triphenylphosphine)palladium(O) (0.03 g, 0.026 mmol) were added and the reaction mixture heated to 110° C. under N$_2$ for 2 h. Reaction mixture was cooled to rt and filtered through Celite, washing with EtOAc (3×10 mL). Combined organics were extracted with water (15 mL) then brine (20 mL). EtOAc layers were then dried, filtered (phase separation cartridge) and concentrated.

Method B (iii) (Suzuki Coupling)

To a solution of methyl-1-(3-fluoro-2-methylphenyl)-3-(((trifluoromethyl)sulfonyl) oxy)cyclopent-2-enecarboxylate (0.3 g, 0.78 mmol) in 1,4 dioxane (8 mL) was added bis(pinacolato)diboron (0.298 g, 1.17 mmol), potassium acetate (0.154 g, 1.56 mmol), tris(dibenzylideneacetone) dipalladium(O), (0.215 g, 0.24 mmol) and S-Phos (0.038 g, 0.094 mmol). The reaction mixture was heated to 80° C. under N$_2$ for 2 h. After this time the reaction mixture was cooled to r.t. and aryl bromide (0.86 mmol), cesium carbonate (0.51 g, 1.57 mmol) and palladium tetrakis(triphenylphosphine) (0.045 g, 0.039 mmol) were added and the reaction mixture heated to 110° C. under N$_2$ for 1 h. Reaction mixture was cooled to r.t. and filtered through Celite, washing with EtOAc (3×10 mL). Combined organics were extracted with water (15 mL) then brine (20 mL). EtOAc layers were then dried, filtered (phase separation cartridge) and concentrated.

Method C (Ester Hydrolysis)

To a solution of Suzuki product in methanol (7 mL) was added 15% w/v sodium hydroxide solution (3 mL). The reaction mixture was capped and heated at 60° C. for 18 h. After this time the contents were cooled to r.t. and methanol was removed under reduced pressure. Aqueous residues were partitioned between EtOAc (40 mL) and 1M aqueous HCl (20 mL). Organic layers were extracted, washed with brine (40 mL), dried, filtered (phase separation cartridge) and concentrated.

Method C (ii) (Ester Hydrolysis)

To a solution of ester (0.14 mmol) in THF/methanol/water (1:1:0.5, 2.5 mL) was added lithium hydroxide hydrate (0.03 g, 0.70 mmol). The reaction mixture was capped and heated at 65° C. for 18 h. After this time the contents were cooled to r.t. and methanol was removed under reduced pressure. Aqueous residues were partitioned between EtOAc (15 mL) and 1 M aqueous HCl (15 mL). Organic layers were extracted, washed with brine (20 mL), dried, filtered (phase separation cartridge) and concentrated.

Method D (Hydroxamic Acid Formation)

To a solution of carboxylic acid (0.08 g, 0.27 mmol), triethylamine (0.08 g, 115 µL, 0.81 mmol) in anhydrous DMF (3 mL) was added tetramethylfluoroformamidinium hexafluorophosphate (0.09 g, 0.35 mmol) at 0° C. The reaction mixture was stirred at this temperature for 15 min, then O-(tetrahydro-2H-pyran-2-yl)hydroxylamine (0.05 g, 0.41 mmol) was added in a single portion. Reaction mixture was then stirred at r.t. for 24 h. After this time the reaction mixture was quenched by the addition of 1 M HCl solution (5 mL). The reaction was partitioned between EtOAc (30 mL) and 1 M HCl (15 mL). The organic layer was separated, washed with brine (40 mL), dried, filtered (phase separation cartridge) and concentrated to give the crude THP protected hydroxamic acid as a pale yellow oil. To this oil was added anhydrous methanol (3 mL) and 4 M HCl in dioxane (2 mL). The reaction mixture was stirred at r.t. for 30 min. After this time solvents were removed under reduced pressure to give crude hydroxamic acid which was purified by preparative HPLC.

Where single enantiomers have been obtained from separation of racemic mixtures the (R) and (S) configuration has been assigned based on comparison to samples prepared from pure (R) or (S) intermediates or by the biochemical potency of single enantiomers.

Example 1: (R)-1-(3-fluoro-2-methylphenyl)-N-hydroxy-3-phenylcyclopent-2-enecarboxamide

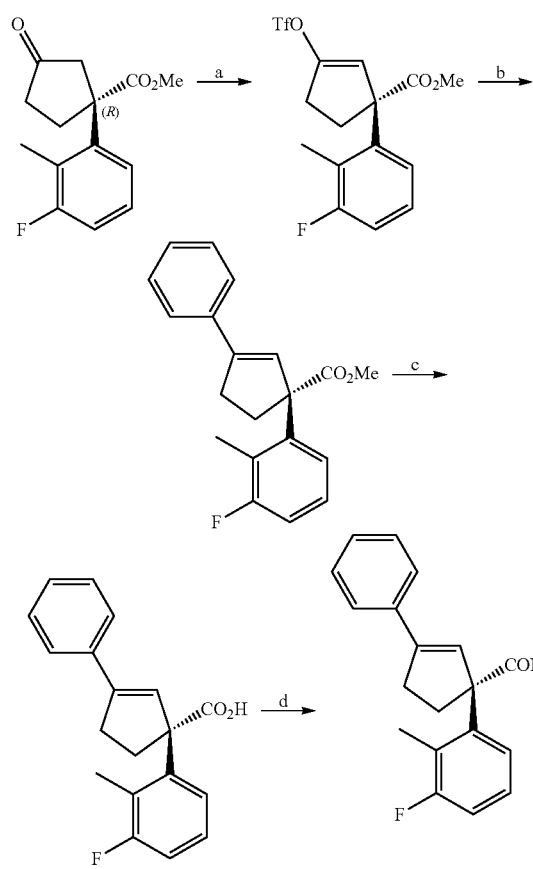

Step 1: (R)-methyl 1-(3-fluoro-2-methylphenyl)-3-(((trifluoromethyl)sulfonyl) oxy)cyclopent-2-enecarboxylate Following Method A from Intermediate 2 (1.30 g, 5.20 mmol). The residue was purified by flash silica column chromatography (gradient elution iso-hexane to 30% EtOAc in iso-hexane) to give the title compound as a colorless semi-solid (2.23 g, 112% by weight; contains residual PhN(Tf)$_2$). MS (ES+) consistent with target (M+H)$^+$.

Step 2: (R)-methyl 1-(3-fluoro-2-methylphenyl)-3-phenylcyclopent-2-enecarboxylate Following Method B from (R)-methyl 1-(3-fluoro-2-methylphenyl)-3-(((trifluoromethyl)sulfonyl) oxy)cyclopent-2-enecarboxylate (0.5 g, 1.31 mmol) and phenylboronic acid (0.16 g, 1.31 mmol). The crude product was purified by flash silica column chromatography (gradient elution iso-hexane to 25% EtOAc in iso-hexane) to give the title compound as a colorless oil (0.23 g, 82%). MS (ES+) consistent with target (M+H)$^+$.

Step 3: (R)-1-(3-fluoro-2-methylphenyl)-3-phenylcyclopent-2-enecarboxylic Acid Following Method C from (R)-methyl 1-(3-fluoro-2-methylphenyl)-3-phenylcyclopent-2-ene-carboxylate (0.23 g) and used without further purification (0.194 g, 92%). MS (ES+) consistent with target (M+H)$^+$.

Step 4: (R)-1-(3-fluoro-2-methylphenyl)-N-hydroxy-3-phenylcyclopent-2-enecarboxamide Following Method D from (R)-1-(3-fluoro-2-methylphenyl)-3-phenylcyclopent-2-enecarboxylic acid (0.08 g, 0.27 mmol) and purified by preparative HPLC to give the title compound as a cream solid (44 mg, 52%). LCMS (ES+) 312 (M+H)$^+$, RT 3.89 min (Analytical method 1); $^1$H NMR δ (ppm) (DMSO-d$_6$): 10.12 (1H, s), 8.73 (1H, s), 7.58 (2H, d, J=1.6 Hz), 7.54-7.28 (3H, m), 7.18 (2H, q, J=1.6 Hz), 7.14 (1H, t, J=1.6 Hz), 6.49 (1H, s), 3.31-3.23 (1H, m), 2.90-2.84 (1H, m), 2.75-2.69 (1H, m), 2.14 (3H, d, J=2.4 Hz), 1.88-1.81 (1H, m).

Example 2: (S)-1-(3-fluoro-2-methylphenyl)-N-hydroxy-3-phenylcyclopent-2-enecarboxamide

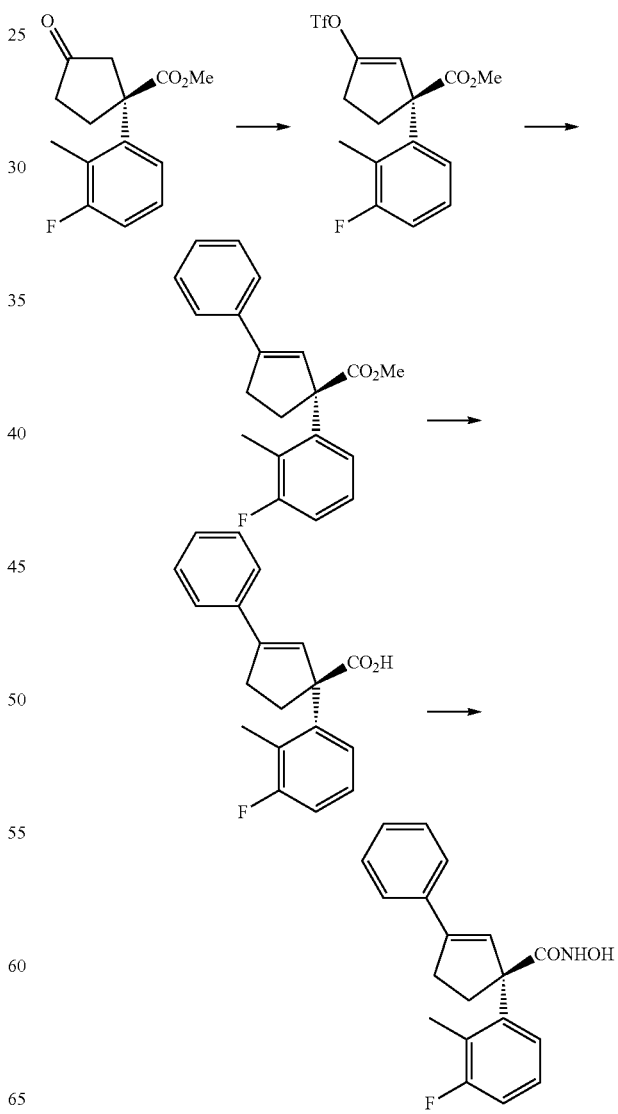

Step 1: (S)-methyl 1-(3-fluoro-2-methylphenyl)-3-(((trifluoromethyl)sulfonyl) oxy)cyclopent-2-enecarboxylate Following Method A from Intermediate 1 (1.50 g, 6.00 mmol). The residue was purified by flash silica column chromatography (gradient elution iso-hexane to 30% EtOAc in iso-hexane) to give the title compound as a colorless oil (1.73 g, 75%). MS (ES+) consistent with target (M+H)+; 1H NMR δ (ppm) (CDCl3): 7.14 (1H, q, J=1.6 Hz), 6.97 (2H, dd, J=1.6 Hz), 5.96 (1H, s), 3.69 (3H, s), 3.62-3.30 (1H, m), 2.88-2.84 (1H, m), 2.69-2.64 (1H, m), 2.08 (3H, d, J=2.4 Hz), 2.02-1.95 (1H, m).

Step 2: (S)-methyl 1-(3-fluoro-2-methylphenyl)-3-phenylcyclopent-2-enecarboxylate Following Method B from (S)-methyl 1-(3-fluoro-2-methylphenyl)-3-(((trifluoromethyl)sulfonyl) oxy)cyclopent-2-enecarboxylate (0.2 g, 0.52 mmol) and phenylboronic acid. The crude product was purified by flash silica column chromatography (gradient elution iso-hexane to 25% EtOAc in iso-hexane) to give the title compound as a colorless oil (0.112 g, 70%). MS (ES+) consistent with target (M+H)+.

Step 3: (S)-1-(3-fluoro-2-methylphenyl)-3-phenylcyclopent-2-enecarboxylic Acid Following Method C from (S)-methyl 1-(3-fluoro-2-methylphenyl)-3-phenylcyclopent-2-ene-carboxylate (0.112 g, 0.36 mmol) and used without further purification (0.1 g, 94%). MS (ES+) consistent with target (M+H)+.

Step 4: (S)-1-(3-fluoro-2-methylphenyl)-N-hydroxy-3-phenylcyclopent-2-enecarboxamide Following Method D from (S)-1-(3-fluoro-2-methylphenyl)-3-phenylcyclopent-2-enecarboxylic acid (0.08 g, 0.27 mmol) and purified by preparative HPLC to give the title compound as a cream solid (0.02 g, 24%). LCMS (ES+) 312 (M+H)+, RT 3.98 min (Analytical method 1); 1H NMR δ (ppm) (DMSO-d6): 10.12 (1H, s), 8.74 (1H, s), 7.58 (2H, d, J=1.6 Hz), 7.54-7.28 (3H, m), 7.18 (2H, q, J=1.6 Hz), 7.14 (1H, t, J=1.6 Hz), 6.49 (1H, s), 3.31-3.23 (1H, m), 2.90-2.84 (1H, m), 2.75-2.69 (1H, m), 2.14 (3H, d, J=2.4 Hz), 1.88-1.81 (1H, m).

Example 3: (R)-1-(3-fluoro-2-methyl-phenyl)-N-hydroxy-3-(o-tolyl)cyclopent-2-ene-1-carboxamide

Example 4: (S)-1-(3-fluoro-2-methyl-phenyl)-N-hydroxy-3-(o-tolyl)cyclopent-2-ene-1-carboxamide

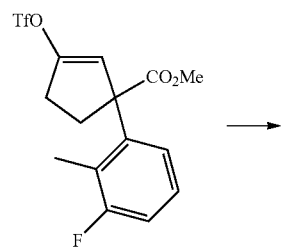

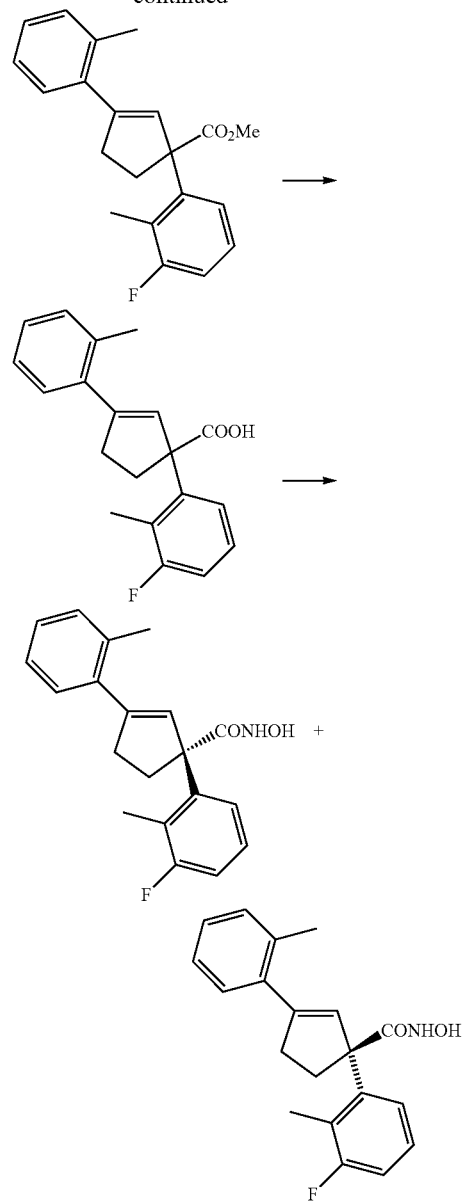

Step 1: (±)-methyl 1-(3-fluoro-2-methyl-phenyl)-3-(o-tolyl)cyclopent-2-ene-1-carboxylate Prepared from (±)-methyl 1-(3-fluoro-2-methyl-phenyl)-3-(trifluoromethylsulfonyloxy)cyclopent-2-ene-1-carboxylate and 2-methylphenyl boronic acid following Method B to give the title compound as a clear oil. MS (ES+) consistent with (M–CO2Me)+.

Step 2: (±)-1-(3-fluoro-2-methyl-phenyl)-3-(o-tolyl)cyclopent-2-ene-1-carboxylic Acid Prepared from (±)-methyl 1-(3-fluoro-2-methyl-phenyl)-3-(o-tolyl)cyclopent-2-ene-1-carboxylate following Method C to give the title compound as a tan oil. MS (ES+) consistent with target (M+H)+.

45

Step 3: (R)-1-(3-fluoro-2-methyl-phenyl)-N-hydroxy-3-(o-tolyl)cyclopent-2-ene-1-carboxamide and (S)-1-(3-fluoro-2-methyl-phenyl)-N-hydroxy-3-(o-tolyl)cyclopent-2-ene-1-carboxamide Following Method D from (±)-1-(3-fluoro-2-methyl-phenyl)-3-(o-tolyl)cyclopent-2-ene-1-carboxylic acid followed by preparative HPLC then separation by chiral HPLC to give the title compounds as off white solids; enantiomer 1 (R) (15 mg, 100% ee) (Chiralpak IC 10/90 IPA/MeOH (50/50/0.1% formic acid)/heptane, 5.0 mL/min), 1000 psi); RT 7.4 min (Chiralpak IC 10/90 IPA/MeOH (50/50/0.1% formic acid)/heptane, 1.0 mL/min); LCMS (ES+) 326 (M+H)$^+$, RT 4.14 min (Analytical method 1); $^1$H NMR δ (ppm) (DMSO-$d_6$): 10.07 (1H, s), 8.73 (1H, s), 7.27-7.16 (6H, m), 7.09-7.04 (1H, m), 6.08 (1H, s), 3.32-3.25 (1H, m), 2.91-2.83 (1H, m), 2.68-2.61 (1H, m), 2.41 (3H, s), 2.14 (3H, d, J=2.5 Hz), 1.83-1.76 (1H, m).

Enantiomer 2 (S) (15 mg, 100% ee) (Chiralpak IC 10/90 IPA/MeOH (50/50/0.1% formic acid)/heptane, 5.0 mL/min), 1000 psi); RT 8.5 mins (Chiralpak IC 10/90 IPA/MeOH (50/50/0.1% formic acid)/heptane, 1.0 mL/min); LCMS (ES+) 326 (M+H)$^+$, RT 4.15 min (Analytical method 1); $^1$H NMR δ (ppm) (DMSO-$d_6$): 10.07 (1H, s), 8.73 (1H, s), 7.27-7.16 (6H, m), 7.09-7.04 (1H, m), 6.08 (1H, s), 3.32-3.25 (1H, m), 2.91-2.83 (1H, m), 2.68-2.61 (1H, m), 2.41 (3H, s), 2.14 (3H, d, J=2.5 Hz), 1.83-1.76 (1H, m).

Example 5: (R)-1-(3-fluoro-2-methylphenyl)-3-(5-fluoropyridin-3-yl)-N-hydroxycyclopent-2-enecarboxamide Example 6: (S)-1-(3-fluoro-2-methylphenyl)-3-(5-fluoropyridin-3-yl)-N-hydroxycyclopent-2-enecarboxamide From Intermediate 3:

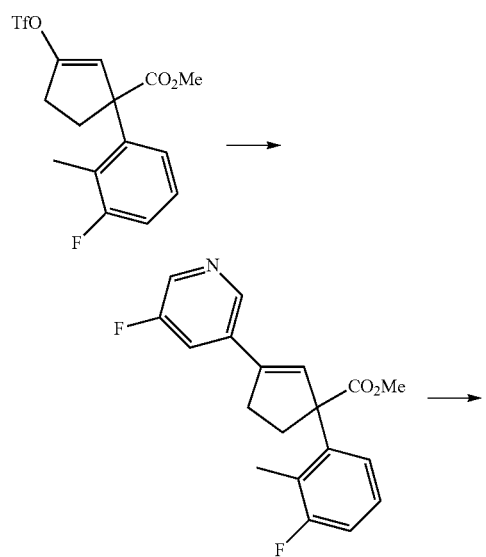

46

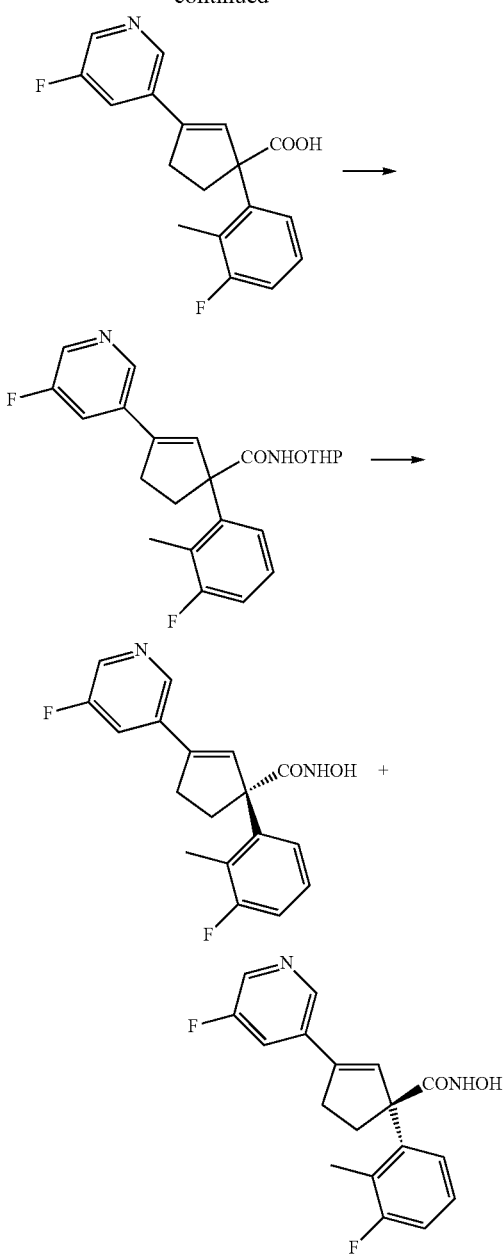

Step 1: (±)-methyl 1-(3-fluoro-2-methyl-phenyl)-3-(5-fluoropyridin-3-yl)cyclopent-2-ene-1-carboxylate A suspension of (±)-methyl 1-(3-fluoro-2-methyl-phenyl)-3-(trifluoromethylsulfonyloxy)cyclopent-2-ene-1-carboxylate (prepared using Method A from Intermediate 3, 1.01 g, 2.64 mmol), 3-fluoropyridine-5-boronic acid (376 mg, 2.67 mmol), Pd(PPh$_3$)$_4$ (153 mg, 0.13 mmol) and CsF (597 mg, 3.93 mmol in 4:1 v/v DME:MeOH (8.7 mL) was stirred at 120° C. for 1 h under microwave irradiation. The mixture was concentrated onto silica and purified by silica column chromatography (gradient elution, 0-100% EtOAc in iso-hexane) to yield the title compound as a white powder (760 mg, 87%). MS (ES+) consistent with target (M+H)$^+$.

Step 2: (±)-1-(3-fluoro-2-methyl-phenyl)-3-(5-fluoropyridin-3-yl)cyclopent-2-ene-1-carboxylic Acid From (±)-methyl 1-(3-fluoro-2-methyl-phenyl)-3-(5-fluoropyridin-3-yl)cyclopent-2-ene-1-carboxylate (760 mg, 2.31 mmol) using Method C. After cooling to room temperature the mixture was concentrated to dryness and partitioned between water (20 mL) and EtOAc (20 mL). The mixture was acidified to pH 6 with acetic acid before separating the two phases. The aqueous phase was extracted with EtOAc (20 mL); the combined organic extracts were dried ($Na_2SO_4$) and concentrated. Purification by flash silica column chromatography (gradient elution $CH_2Cl_2$ to 10% MeOH in $CH_2Cl_2$) yielded the title compound as shiny white prisms (503 mg, 69%).

Step 3: (±)-1-(3-fluoro-2-methyl-phenyl)-3-(5-fluoropyridin-3-yl)-N-tetrahydropyran-2-yloxy-cyclopent-2-ene-1-carboxamide A stirred solution of (±)-1-(3-fluoro-2-methyl-phenyl)-3-(5-fluoro-3-pyridyl)cyclopent-2-ene-1-carboxylic acid (104 mg, 0.33 mmol) in DMF (2.3 mL) at 20° C. was treated with $Et_3N$ (0.13 mL, 0.93 mmol) and TFFH (106 mg, 0.40 mmol). The mixture was stirred for 15 min before addition of O-(tetrahydropyranyl)hydroxylamine (45.2 mg, 0.39 mmol), after which stirring was continued for 19 h. The reaction was poured into water (50 mL) and extracted with EtOAc (3×25 mL). The combined organic extracts were washed with water (3×25 mL) and brine (25 mL), dried ($Na_2SO_4$) and concentrated. Purification by flash silica column chromatography (gradient elution iso-hexane to 100% EtOAc in iso-hexane) yielded the title compound as a colorless oil (81 mg, 59%). MS (ES+) consistent with target $(M+H)^+$.

Step 4: (R)-1-(3-fluoro-2-methylphenyl)-3-(5-fluoropyridin-3-yl)-N-hydroxycyclopent-2-enecarboxamide and (S)-1-(3-fluoro-2-methylphenyl)-3-(5-fluoropyridin-3-yl)-N-hydroxycyclopent-2-enecarboxamide A solution of (±)-1-(3-fluoro-2-methyl-phenyl)-3-(5-fluoropyridin-3-yl)-N-tetrahydropyran-2-yloxy-cyclopent-2-ene-1-carboxamide (81 mg, 0.20 mmol) in 2:1 v/v THF: water (8.6 mL) at 20° C. was treated with PTSA monohydrate (26.5 mg, 0.14 mmol). The mixture was stirred in a sealed tube at 50° C. for 6 h. After cooling to room temperature, MP-carbonate beads (227 mg) were added and the mixture stirred for 50 min. The mixture was filtered to remove solids, washing with EtOAc (5×5 mL). The filtrate was concentrated and purified by preparative HPLC to give the racemic product as a white solid (35 mg, 54%). Preparative chiral purification gave the title compounds as white solids: (R) enantiomer (14 mg, 22% yield, 100% ee); (Chiralpak IA 40/60 EtOH (0.1% formic acid)/heptane, 5.0 mL/min), 1400 psi); RT 13.15 min (Chiralpak IA 40/60 EtOH (0.1% formic acid)/heptane, 1.0 mL/min); LCMS (ES+) 331 $(M+H)^+$, RT 3.32 min (Analytical method 1); $^1H$ NMR δ (ppm) (DMSO-$d_6$): 10.21 (1H, s), 8.82 (1H, s), 8.70 (1H, apparent t, J=1.6 Hz), 8.55 (1H, d, J=2.6 Hz), 7.97 (1H, ddd, J=8.8, 4.0, 3.3 Hz), 7.24-7.19 (2H, m), 7.13-7.06 (1H, m), 6.78 (1H, s), 3.30-3.23 (1H, m), 2.99-2.90 (1H, m), 2.83-2.70 (1H, m), 2.17 (3H, d, J=2.5 Hz), 1.94 (1H, ddd, J=13.1, 9.1, 6.1 Hz);

(S) enantiomer (13 mg, 20% yield, 100% ee); (Chiralpak IA 40/60 EtOH (0.1% formic acid)/heptane, 5.0 mL/min), 1400 psi); RT 9.46 min (Chiralpak IA 40/60 EtOH (0.1% formic acid)/heptane, 1.0 mL/min); LCMS (ES+) 331 $(M+H)^+$, RT 3.32 min (Analytical method 1); $^1H$ NMR δ (ppm) (DMSO-$d_6$): 10.21 (1H, s), 8.82 (1H, s), 8.70 (1H, apparent t, J=1.6 Hz), 8.55 (1H, d, J=2.6 Hz), 7.97 (1H, ddd, J=8.8, 4.0, 3.3 Hz), 7.24-7.19 (2H, m), 7.13-7.06 (1H, m), 6.78 (1H, s), 3.30-3.23 (1H, m), 2.99-2.90 (1H, m), 2.83-2.70 (1H, m), 2.17 (3H, d, J=2.5 Hz), 1.94 (1H, ddd, J=13.1, 9.1, 6.1 Hz).

Example 5: (R)-1-(3-fluoro-2-methylphenyl)-3-(5-fluoropyridin-3-yl)-N-hydroxycyclopent-2-enecarboxamide From Intermediate 2:

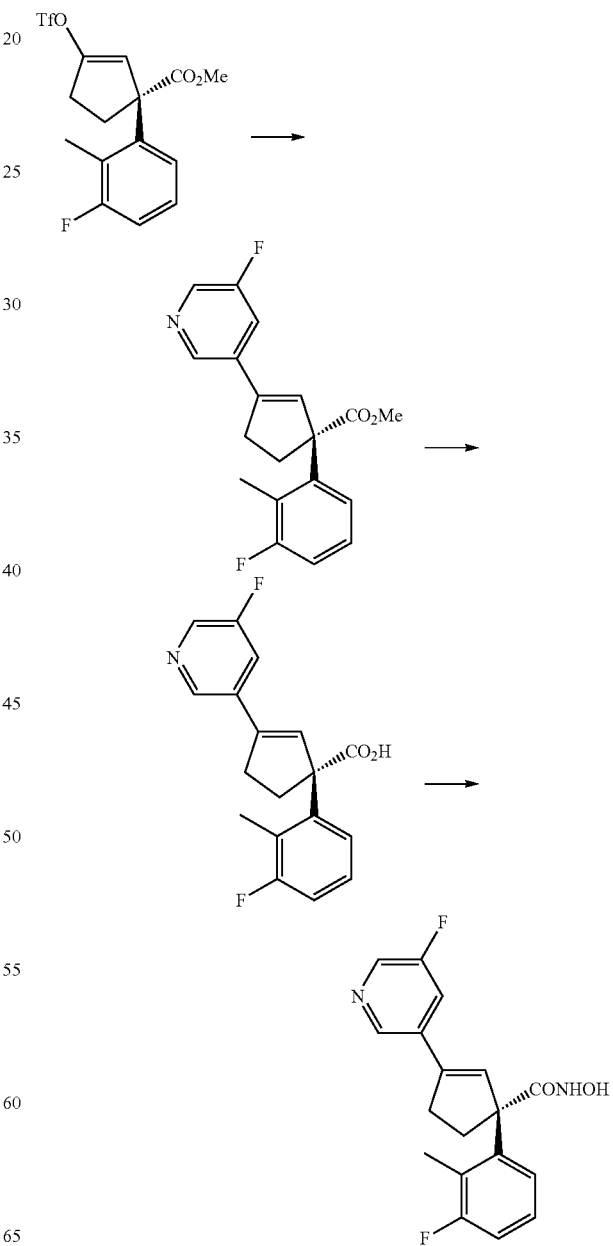

Step 1: (R)-methyl 1-(3-fluoro-2-methylphenyl)-3-(5-fluoropyridin-3-yl)cyclopent-2-enecarboxylate Following Method B from (R)-methyl 1-(3-fluoro-2-methylphenyl)-3-(((trifluoromethyl)sulfonyl) oxy)cyclopent-2-enecarboxylate (0.4 g, 1.05 mmol) and 3-fluoropyridine-5-boronic acid. The crude product was purified by flash silica column chromatography (gradient elution, 0-33% EtOAc in iso-hexane) to give the title compound as a colorless oil (0.23 g, 65%). MS (ES+) consistent with target (M+H)+; ¹H NMR δ (ppm) (CDCl₃): 8.61 (1H, t, J=1.7 Hz), 8.41 (1H, d, J=2.7 Hz), 7.53-7.47 (1H, m), 7.17-7.09 (1H, m), 7.07-6.92 (2H, m), 6.45 (1H, t, J=1.9 Hz), 3.70 (3H, s), 3.37 (1H, ddd, J=13.3, 8.8, 4.3 Hz), 3.08-2.97 (1H, m), 2.83 (1H, dddd, J=16.1, 9.3, 4.5, 1.9 Hz), 2.14 (3H, d, J=2.5 Hz), 2.06 (1H, ddd, J=13.2, 9.3, 6.0 Hz).

Step 2: (R)-1-(3-fluoro-2-methylphenyl)-3-(5-fluoropyridin-3-yl)cyclopent-2-enecarboxylic Acid Following Method C from (R)-1-(3-fluoro-2-methylphenyl)-3-(5-fluoropyridin-3-yl)cyclopent-2-enecarboxylic acid (0.20 g) and used without further purification (0.196 g, 97%). MS (ES+) consistent with target (M+H)+; ¹H NMR δ (ppm) (DMSO-d₆): 12.66 (1H, s), 8.68 (1H, s), 8.48 (1H, d, J=2.7 Hz), 8.01 (1H, d, J=10.5 Hz), 7.18-7.10 (2H, m), 7.05-6.98 (1H, m), 6.80 (1H, s), 3.14 (1H, ddd, J=13.0, 8.9, 4.5 Hz), 2.99-2.88 (1H, m), 2.80-2.70 (1H, m), 2.12 (3H, d, J=2.5 Hz), 1.90 (1H, ddd, J=13.0, 9.3, 5.9 Hz).

Step 3: (R)-1-(3-fluoro-2-methylphenyl)-3-(5-fluoropyridin-3-yl)-N-hydroxycyclopent-2-enecarboxamide Following Method D from (R)-1-(3-fluoro-2-methylphenyl)-3-(5-fluoropyridin-3-yl)cyclopent-2-enecarboxylic acid (0.18 g, 0.57 mmol) and purified by preparative HPLC (130 mg, 69%). LCMS (ES+) 331 (M+H)+; RT 3.41 min (Analytical method 1); ¹H NMR δ (ppm) (DMSO-d₆): 10.21 (1H, s), 8.82 (1H, s), 8.70 (1H, apparent t, J=1.6 Hz), 8.55 (1H, d, J=2.6 Hz), 7.97 (1H, ddd, J=8.8, 4.0, 3.3 Hz), 7.24-7.19 (2H, m), 7.13-7.06 (1H, m), 6.78 (1H, s), 3.30-3.23 (1H, m), 2.99-2.90 (1H, m), 2.83-2.70 (1H, m), 2.17 (3H, d, J=2.5 Hz), 1.94 (1H, ddd, J=13.1, 9.1, 6.1 Hz).

Example 7: (R)-1-(3-fluoro-2-methylphenyl)-N-hydroxy-3-(pyrazin-2-yl)cyclopent-2-ene carboxamide

Example 8: (S)-1-(3-fluoro-2-methylphenyl)-N-hydroxy-3-(pyrazin-2-yl)cyclopent-2-ene carboxamide

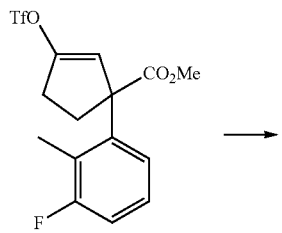

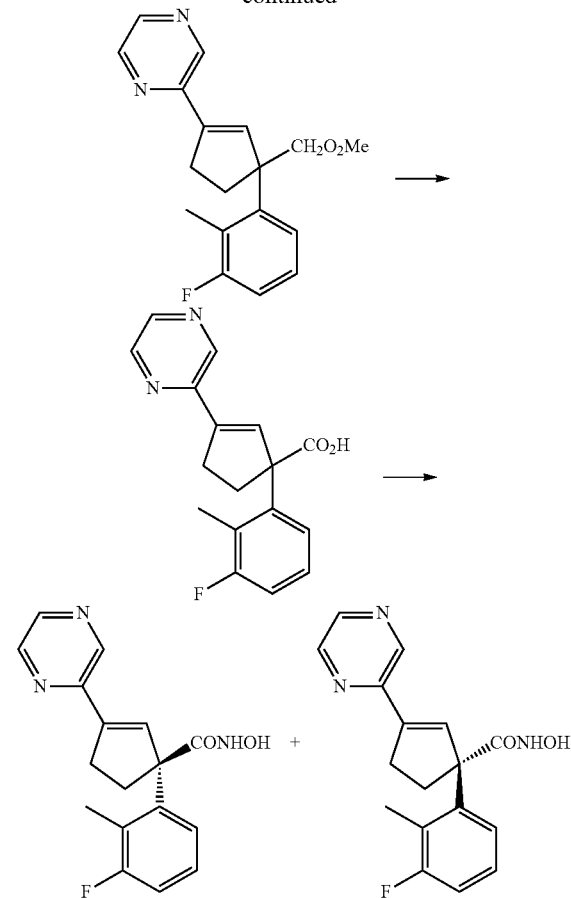

Step 1: (±)-methyl 1-(3-fluoro-2-methylphenyl)-3-(pyrazin-2-yl)cyclopent-2-ene-1-carboxylate Following Method B (ii) from (±)-methyl 1-(3-fluoro-2-methylphenyl)-3-(((trifluoromethyl) sulfonyl) oxy) cyclopent-2-enecarboxylate (0.1 g, 0.26 mmol) and 2-bromopyrazine. The crude product was purified by flash silica column chromatography (gradient elution iso-hexane to 25% EtOAc in iso-hexane) to give the title compound as a pale yellow oil (55 mg, 72%). MS (ES+) consistent with target (M+H)+; ¹H NMR δ (ppm) (CDCl₃): 8.77 (1H, s), 8.58 (1H, d, J=1.6 Hz), 8.48 (1H, d, J=1.6 Hz), 7.14-7.06 (2H, m), 6.97 (1H, t, J=2.6 Hz), 6.87 (1H, s), 3.71 (3H, s), 3.40-3.36 (1H, m), 3.12-3.09 (1H, m), 2.98-2.94 (1H, m), 2.15 (3H, d, J=2.4 Hz), 2.12-2.06 (1H, m).

Step 2: (±)-1-(3-fluoro-2-methylphenyl)-3-(pyrazin-2-yl)cyclopent-2-ene-carboxylic Acid Following Method C from (±)-methyl 1-(3-fluoro-2-methylphenyl)-3-(pyrazin-2-yl)cyclopent-2-ene-1-carboxylate (0.055 g, 0.18 mmol) and used without further purification (0.049 g, 94%). MS (ES+) consistent with target (M+H)+.

Step 3: (S)-1-(3-fluoro-2-methylphenyl)-N-hydroxy-3-(pyrazin-2-yl)cyclopent-2-enecarboxamide and (R)-1-(3-fluoro-2-methylphenyl)-N-hydroxy-3-(pyrazin-2-yl)cyclopent-2-enecarboxamide Following Method D from (S)-1-(3-fluoro-2-methylphenyl)-3-(pyrazin-2-yl)cyclopent-2-enecarboxylic acid (0.1 g, 0.33 mmol) and purified by preparative HPLC to give the racemic product as a cream solid (43 mg, 35%). Preparative chiral purification gave the title compounds as white solids; (S) enantiomer (12 mg, 20%, >99.5% ee) (Chiralpak IA 50/50 IPA/MeOH (0.1% formic acid)/heptane, 5.0 mL/min), r.t., 1400 psi); LCMS (ES+) 331 (M+H)+, RT 3.03 min (Analytical method 1); RT 18.0 min, (Chiralpak IA 40/60 EtOH (0.1% formic acid)/heptane, 1.0 mL/min, r.t.); $^1$H NMR δ (ppm) (DMSO-$d_6$): 10.22 (1H, s), 8.92 (1H, s), 8.78 (1H, s), 8.65 (1H, d, J=1.6 Hz), 8.55 (1H, d, J=1.6 Hz), 7.19-7.04 (3H, m), 7.02 (1H, s), 3.30-3.26 (1H, m), 2.97-2.91 (1H, m), 2.84-2.82 (1H, m), 2.14 (3H, d, J=2.4 Hz), 1.94-1.87 (1H, m).

(R) enantiomer (11.5 mg, 19%, >99.5% ee) (Chiralpak IA 50/50 IPA/MeOH (0.1% formic acid)/heptane, 5.0 mL/min), r.t., 1400 psi). LCMS (ES+) 331 (M+H)+, RT 3.03 min (Analytical method 1); RT 11.8 min (Chiralpak IA 40/60 EtOH (0.1% formic acid)/heptane, 1.0 mL/min); $^1$H NMR δ (ppm) (DMSO-$d_6$): 10.22 (1H, s), 8.92 (1H, s), 8.78 (1H, s), 8.65 (1H, d, J=1.6 Hz), 8.55 (1H, d, J=1.6 Hz), 7.19-7.04 (3H, m), 7.02 (1H, s), 3.30-3.26 (1H, m), 2.97-2.91 (1H, m), 2.84-2.82 (1H, m), 2.14 (3H, d, J=2.4 Hz), 1.94-1.87 (1H, m).

Example 9: (R)-1-(3-fluoro-2-methylphenyl)-N-hydroxy-3-(2-methylpyrimidin-5-yl)cyclopent-2-enecarboxamide

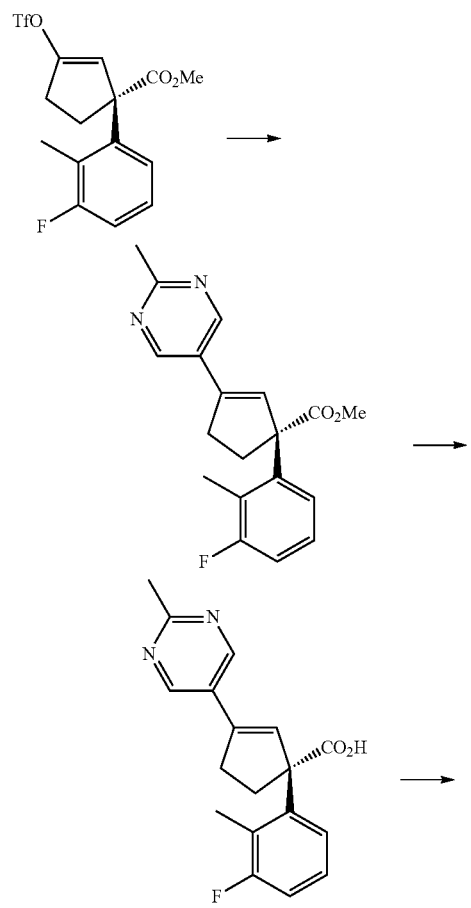

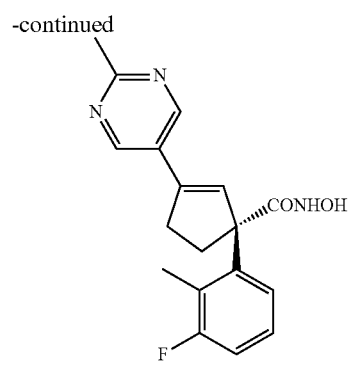

Step 1: (R)-methyl 1-(3-fluoro-2-methylphenyl)-3-(2-methylpyrimidin-5-yl)cyclopent-2-enecarboxylate Following Method B from (R)-methyl 1-(3-fluoro-2-methylphenyl)-3-((((trifluoromethyl)sulfonyl) oxy)cyclopent-2-enecarboxylate (0.5 g, 1.31 mmol). The crude product was purified by flash silica column chromatography (gradient elution, 0-50% EtOAc in iso-hexane) to give the title compound as a brown oil (0.14 g, 33%); MS (ES+) consistent with target (M+H)+; $^1$H NMR δ (ppm) (CDCl$_3$): 8.76 (2H, s), 7.16-7.09 (1H, m), 7.06-6.91 (2H, m), 6.46-6.40 (1H, m), 3.71 (3H, s), 3.37 (1H, ddd, J=13.3, 8.8, 4.4 Hz), 3.07-2.96 (1H, m), 2.83 (1H, dddd, J=16.1, 9.3, 4.4, 1.9 Hz), 2.76 (3H, s), 2.14 (3H, d, J=2.5 Hz), 2.10-1.99 (1H, m).

Step 2: (R)-1-(3-fluoro-2-methylphenyl)-3-(2-methylpyrimidin-5-yl)cyclopent-2-enecarboxylic Acid Following Method C from (R)-methyl 1-(3-fluoro-2-methylphenyl)-3-(2-methylpyrimidin-5-yl) cyclopent-2-enecarboxylate (0.14 g) and used without further purification (0.12 g, 90%); MS (ES+) consistent with target (M+H)+; $^1$H NMR δ (ppm) (DMSO-$d_6$): 12.70 (1H, s), 8.94 (2H, s), 7.20-7.11 (2H, m), 7.08-7.02 (1H, m), 6.79 (1H, s), 3.16 (1H, ddd, J=13.23, 8.77, 4.30 Hz), 2.98-2.87 (1H, m), 2.81-2.71 (1H, m), 2.61 (3H, s), 2.13 (3H, d, J=2.46 Hz), 1.95-1.85 (1H, m).

Step 3: (R)-1-(3-fluoro-2-methylphenyl)-N-hydroxy-3-(2-methylpyrimidin-5-yl)cyclopent-2-enecarboxamide Following Method D from (R)-1-(3-fluoro-2-methylphenyl)-3-(2-methylpyrimidin-5-yl)cyclopent-2-enecarboxylic acid (0.12 g, 0.38 mmol) and purified by preparative HPLC (41 mg, 37%); LCMS (ES+) 328 (M+H)+, RT 3.03 min (Analytical method 1); $^1$H NMR δ (ppm) (DMSO-$d_6$): 10.17 (1H, s), 8.89 (2H, s), 8.78 (1H, s), 7.19-7.05 (3H, m), 6.70 (1H, s), 3.31-3.26 (1H, m), 2.91-2.87 (1H, m), 2.78-2.72 (1H, m), 2.64 (3H, s), 2.14 (3H, d, J=2.4 Hz), 1.93-1.86 (1H, m).

Example 10: (S)-1-(3-fluoro-2-methylphenyl)-N-hydroxy-3-(2-methylpyrimidin-5-yl)cyclopent-2-enecarboxamide

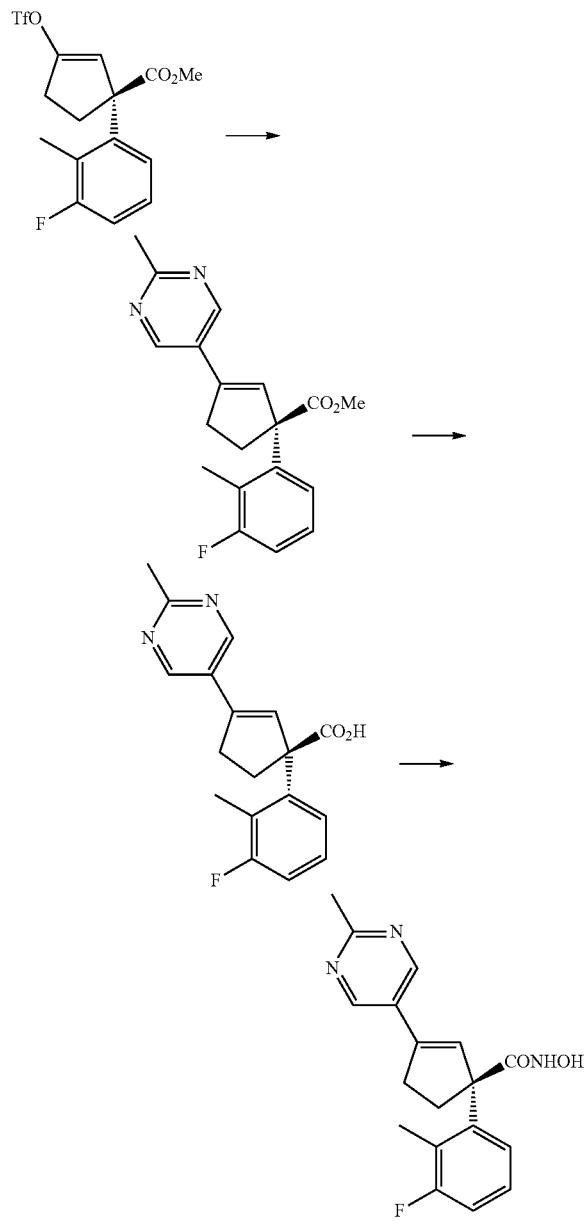

Step 1: (S)-methyl 1-(3-fluoro-2-methylphenyl)-3-(2-methylpyrimidin-5-yl)cyclopent-2-ene Carboxylate Following Method B (ii) from (S)-methyl-1-(3-fluoro-2-methylphenyl)-3-(((trifluoromethyl)sulfonyl) oxy)cyclopent-2-enecarboxylate (0.2 g, 0.5 mmol). Crude material was purified by flash silica column chromatography (gradient elution iso-hexane to 100% EtOAc in iso-hexane) to yield the title compound as a pale yellow oil (0.108 g, 63%). MS (ES+) consistent with target (M+H)+; $^1$H NMR δ (ppm) (CDCl$_3$): 8.62 (2H, s), 7.14-6.97 (3H, m), 6.76 (1H, s), 3.71 (3H, s), 3.40-3.36 (1H, m), 3.12-3.09 (1H, m), 2.98-2.94 (1H, m), 2.68 (3H, s) 2.15 (3H, d, J=2.4 Hz), 2.12-2.06 (1H, m).

Step 2: (S)-1-(3-fluoro-2-methylphenyl)-3-(2-methylpyrimidin-5-yl)cyclopent-2-enecarboxylic Acid Following Method C from (S)-methyl 1-(3-fluoro-2-methylphenyl)-3-(2-methylpyrimidin-5-yl)cyclopent-2-enecarboxylate (0.108 g, 0.33 mmol) and used without further purification (0.074 g, 72%). MS (ES+) consistent with target (M+H)+.

Step 3: (S)-1-(3-fluoro-2-methylphenyl)-N-hydroxy-3-(2-methylpyrimidin-5-yl)cyclopent-2-ene Carboxamide Following Method D from (S)-1-(3-fluoro-2-methylphenyl)-3-(2-methylpyrimidin-5-yl)cyclopent-2-enecarboxylic acid (0.074 g, 0.24 mmol) and purified by preparative HPLC to give the title compound as a cream solid (0.02 g, 28%). LCMS (ES+) 328 (M+H)+, RT 2.93 min (Analytical method 1); $^1$H NMR δ (ppm) (DMSO-d$_6$): 10.17 (1H, s), 8.89 (2H, s), 8.78 (1H, s), 7.19-7.05 (3H, m), 6.70 (1H, s), 3.31-3.26 (1H, m), 2.91-2.87 (1H, m), 2.78-2.72 (1H, m), 2.64 (3H, s), 2.14 (3H, d, J=2.4 Hz), 1.93-1.86 (1H, m).

Example 11: (S)-3-(5-chloropyridin-3-yl)-1-(3-fluoro-2-methylphenyl)-N-hydroxycyclopent-2-enecarboxamide

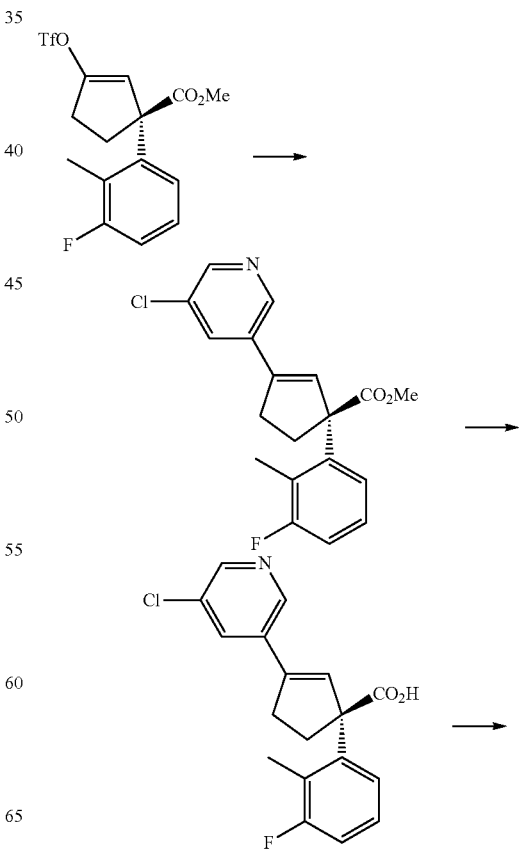

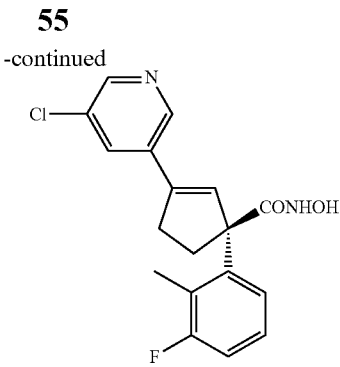

Step 1: (S)-methyl 1-(3-fluoro-2-methylphenyl)-3-(5-chloropyridin-3-yl)cyclopent-2-enecarboxylate Following Method B from (S)-methyl 1-(3-fluoro-2-methylphenyl)-3-(((trifluoromethyl)sulfonyl) oxy)cyclopent-2-enecarboxylate (700 mg, 1.83 mmol) and 3-chloropyridine-5-boronic acid utilizing CsF, DME, MeOH and palladium tetrakis(triphenylphosphine) at 120° C. The crude product was purified by flash column chromatography to give the title compound as a clear gum (354 mg, 56%). MS (ES+) consistent with target (M+H)+.

Step 2: (S)-1-(3-fluoro-2-methylphenyl)-3-(5-chloropyridin-3-yl)cyclopent-2-enecarboxylic Acid Following Method C from (S)-methyl 1-(3-fluoro-2-methylphenyl)-3-(5-chloropyridin-3-yl)cyclopent-2-enecarboxylate (350 mg) and used without further purification (332 mg, 100%). MS (ES+) consistent with target (M+H)+.

Step 3: (S)-3-(5-chloropyridin-3-yl)-1-(3-fluoro-2-methylphenyl)-N-hydroxycyclopent-2-enecarboxamide Following Method D from (S)-1-(3-fluoro-2-methylphenyl)-3-(5-chloropyridin-3-yl)cyclopent-2-enecarboxylic acid (332 mg, 1 mmol) and purified by preparative HPLC to give the title compound as a white solid (144 mg, 42%). LCMS (ES+) 347/349 (M+H)+; RT 3.47 min (Analytical method 1); $^1$H NMR δ (ppm) (DMSO-$d_6$): 10.17 (1H, s), 8.78 (1H, s), 8.74 (1H, d, J=2 Hz), 8.56 (1H, d, J=2.4 Hz), 8.13 (1H, t, J=2 Hz), 7.20-7.17 (2H, m), 7.09-7.05 (1H, m), 6.76 (1H, s), 3.35-3.20 (1H, m), 2.95-2.88 (1H, m), 2.79-2.72 (1H, m), 2.14 (3H, d, J=2.4 Hz), 1.95-1.88 (1H, m).

Example 12: (S)-1-(3-fluoro-2-methylphenyl)-N-hydroxy-3-(quinoxalin-6-yl)cyclopent-2-enecarboxamide

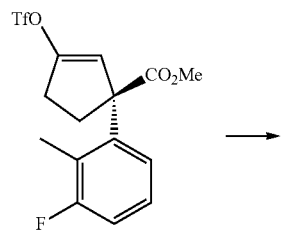

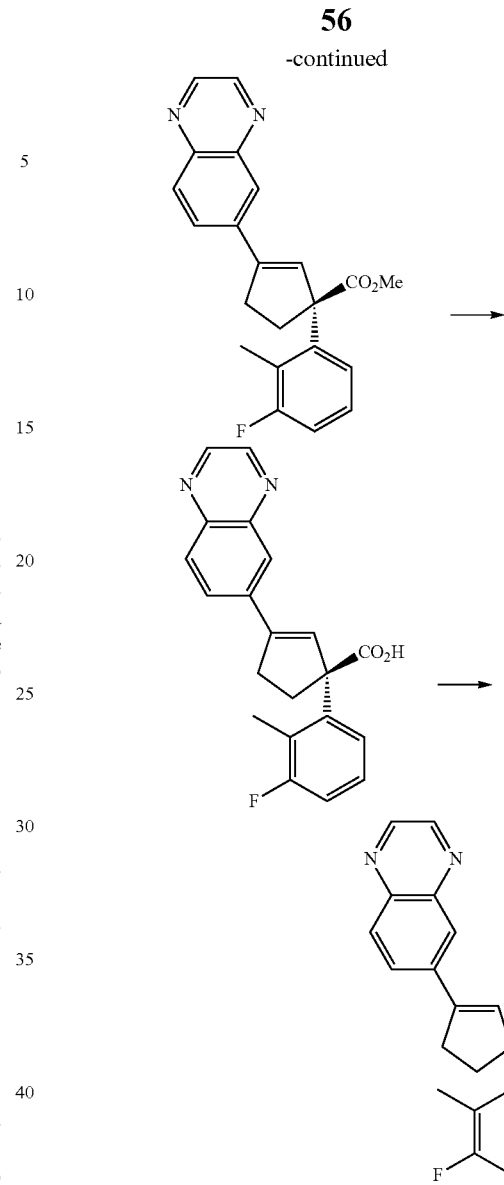

Step 1: (S)-methyl 1-(3-fluoro-2-methylphenyl)-3-(quinoxalin-6-yl)cyclopent-2-enecarboxylate Following Method B from (S)-methyl 1-(3-fluoro-2-methylphenyl)-3-(((trifluoromethyl)sulfonyl) oxy)cyclopent-2-enecarboxylate (330 mg, 0.86 mmol) and quinoxaline-5-boronic acid utilizing CsF, DME, MeOH and palladium tetrakis(triphenylphosphine) at 120° C. The crude product was purified by flash column chromatography to give the title compound as a clear gum (299 mg, 96%). MS (ES+) consistent with target (M+H)+.

Step 2: (S)-1-(3-fluoro-2-methylphenyl)-3-(quinoxalin-6-yl)cyclopent-2-enecarboxylic Acid Following Method C from (S)-methyl 1-(3-fluoro-2-methylphenyl)-3-(quinoxalin-6-yl)cyclopent-2-enecarboxylate (290 mg) and used without further purification (201 mg MS (ES+) consistent with target (M+H)+.

Step 3: (S)-1-(3-fluoro-2-methylphenyl)-N-hydroxy-3-(quinoxalin-6-yl)cyclopent-2-enecarboxamide Following Method D from (S)-1-(3-fluoro-2-methylphenyl)-3-(quinoxalin-6-yl)cyclopent-2-enecarboxylic acid (200 mg, 0.57 mmol) and purified by preparative HPLC to give the title compound as a tan solid (109 mg, 53%). LCMS (ES+) 364 (M+H)+; RT 3.41 min (Analytical method 1); $^1$H NMR δ (ppm) (DMSO-d$_6$): 10.21 (1H, s), 8.97 (1H, d, J=1.6 Hz), 8.93 (1H, d, J=2 Hz), 8.80 (1H, s), 8.22 (1H, dd, J=8.8, 1.6 Hz), 8.11 (1H, d, J=8.8 Hz), 8.05 (1H, d, J=1.6 Hz), 7.25-7.15 (2H, m), 7.11-7.06 (1H, m), 6.86 (1H, s), 3.35-3.25 (1H, m), 3.08-3.01 (1H, m), 2.94-2.89 (1H, m), 2.17 (3H, d, J=2.4 Hz), 1.99-1.92 (1H, m).

Example 13: (S)-1-(3-fluoro-2-methylphenyl)-N-hydroxy-3-(2-(trifluoromethyl)pyridin-4-yl)cyclopent-2-enecarboxamide

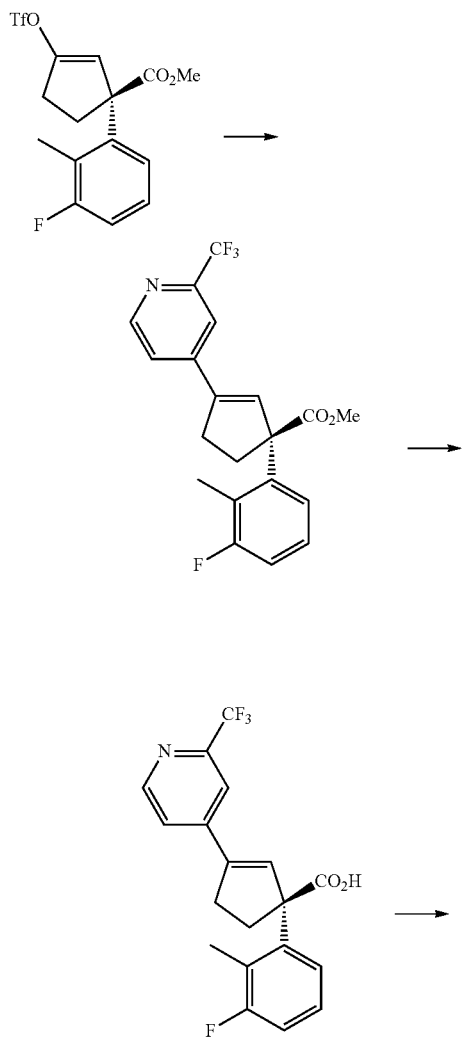

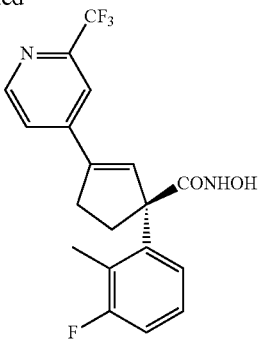

Step 1: (S)-methyl 1-(3-fluoro-2-methylphenyl)-3-(2-(trifluoromethyl)pyridin-4-yl)cyclopent-2-enecarboxylate Following Method B from (S) methyl 1-(3-fluoro-2-methylphenyl)-3-(((trifluoromethyl)sulfonyl)oxy)cyclopent-2-enecarboxylate (310 mg, 0.81 mmol) and 2-trifluoromethyl-pyridine-4-boronic acid utilizing CsF, DME, MeOH and palladium tetrakis(triphenylphosphine) at 120° C. The crude product was purified by flash column chromatography to give the title compound as a clear gum (194 mg, 63%).

Step 2: (S)-1-(3-fluoro-2-methylphenyl)-3-(2-(trifluoromethyl)pyridin-4-yl)cyclopent-2-enecarboxylic Acid Following Method C from (S)-methyl 1-(3-fluoro-2-methylphenyl)-3-(2-(trifluoromethyl)pyridin-4-yl)cyclopent-2-enecarboxylate (190 mg) and used without further purification (141 mg, 77%). MS (ES+) consistent with target (M+H)+.

Step 3: (S)-1-(3-fluoro-2-methylphenyl)-N-hydroxy-3-(2-(trifluoromethyl)pyridin-4-yl)cyclopent-2-enecarboxamide Following Method D from (S)-1-(3-fluoro-2-methylphenyl)-3-(2-(trifluoromethyl)pyridin-4-yl)cyclopent-2-enecarboxylic acid (141 mg, 0.39 mmol) and purified by preparative HPLC to give the title compound as a tan solid (35 mg, 24%). LCMS (ES+) 381 (M+H)+; RT 10.5 min (Analytical method 3); $^1$H NMR δ (ppm) (DMSO-d$_6$): 10.20 (1H, s), 8.82 (1H, s), 8.77 (1H, d, J=5.2 Hz), 8.15 (1H, s), 7.80 (1H, d, J=5.2 Hz), 7.20-7.04 (4H, m), 3.35-3.20 (1H, m), 2.97-2.92 (1H, m), 2.83-2.76 (1H, m), 2.15 (3H, d, J=2.4 Hz), 2.09-1.93 (1H, m).

Example 14: (S)-1-(3-fluoro-2-methylphenyl)-N-hydroxy-3-(pyrimidin-5-yl)cyclopent-2-enecarboxamide

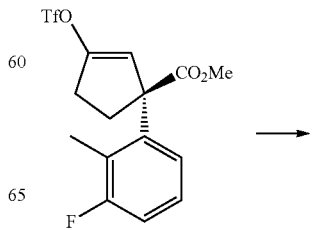

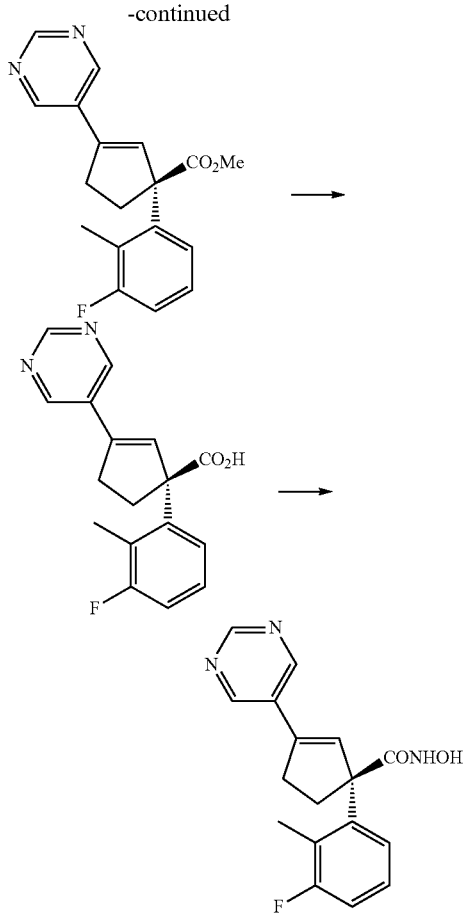

Step 1: (S)-methyl 1-(3-fluoro-2-methylphenyl)-3-(pyrimidin-5-yl)cyclopent-2-enecarboxylate Following Method B from (S) methyl 1-(3-fluoro-2-methylphenyl)-3-(((trifluoromethyl)sulfonyl) oxy)cyclopent-2-enecarboxylate (380 mg, 1 mmol) and pyrimidine-5-boronic acid utilizing CsF, DME, MeOH and palladium tetrakis (triphenylphosphine) at 120° C. The crude product was purified by flash column chromatography to give the title compound as a clear gum (327 mg, 100%). MS (ES+) consistent with target (M+H)+.

Step 2: (S)-1-(3-fluoro-2-methylphenyl)-3-(pyrimidin-5-yl)cyclopent-2-enecarboxylic Acid Following Method C from (S)-methyl 1-(3-fluoro-2-methylphenyl)-3-(pyrimidin-5-yl)cyclopent-2-enecarboxylate (320 mg) and used without further purification (296 mg, 97%). MS (ES+) consistent with target (M+H)+.

Step 3: (S)-1-(3-fluoro-2-methylphenyl)-N-hydroxy-3-(pyrimidin-5-yl)cyclopent-2-enecarboxamide Following Method D from (S)-1-(3-fluoro-2-methylphenyl)-3-(pyrimidin-5-yl)cyclopent-2-enecarboxylic acid (262 mg, 0.88 mmol) and purified by preparative HPLC to give the title compound as a tan solid (144 mg, 52%). LCMS (ES+) 314 (M+H)+; RT 3.02 min (Analytical method 1); 1H NMR δ (ppm) (DMSO-$d_6$): 10.19 (1H, s), 9.15 (1H, s), 9.03 (2H, s), 8.78 (1H, s), 7.21-7.17 (2H, m), 7.15-7.04 (1H, m), 6.86 (1H, s), 3.35-3.21 (1H, m), 2.97-2.90 (1H, m), 2.81-2.74 (1H, m), 2.14 (3H, d, J=2 Hz), 2.09-1.93 (1H, m).

Example 15: (S)-1-(3-fluoro-2-methylphenyl)-3-(5-fluoropyridin-2-yl)-N-hydroxycyclopent-2-enecarboxamide

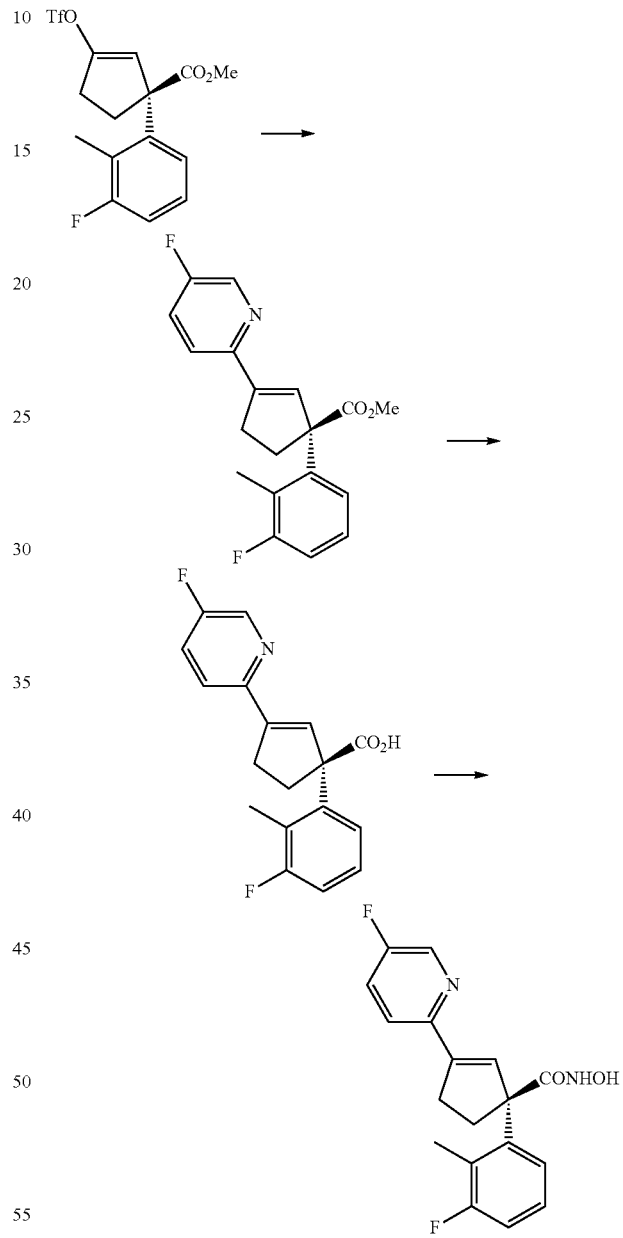

Step 1: (S)-methyl 1-(3-fluoro-2-methylphenyl)-3-(5-fluoropyridin-2-yl)cyclopent-2-enecarboxylate Following Method B (iii) from (S)-methyl 1-(3-fluoro-2-methylphenyl)-3-(((trifluoromethyl)sulfonyl) oxy)cyclopent-2-enecarboxylate (0.3 g, 0.78 mmol). The crude product was purified by flash column chromatography to yield the title compound as a pale yellow gum (217 mg, 84%). MS (ES+) consistent with target (M+H)+.

Step 2: (S)-1-(3-fluoro-2-methylphenyl)-3-(5-fluoro-pyridin-2-yl)cyclopent-2-enecarboxylic Acid Following Method C from (S)-methyl 1-(3-fluoro-2-methylphenyl)-3-(5-fluoropyridin-2-yl)cyclopent-2-enecarboxylate (217 mg) and used without further purification (187 mg, 72%). MS (ES+) consistent with target (M+H)+.

Step 3: (S)-1-(3-fluoro-2-methylphenyl)-3-(5-fluoro-pyridin-2-yl)-N-hydroxycyclopent-2-enecarboxamide Following Method D from (S)-1-(3-fluoro-2-methylphenyl)-3-(5-fluoropyridin-2-yl)cyclopent-2-enecarboxylic acid (187 mg, 0.59 mmol) and purified by preparative HPLC to give the title compound as an off white solid (89 mg, 45%). LCMS (ES+) 331 (M+H)+; RT 3.53 min (Analytical method 1). $^1$H NMR δ (ppm) (DMSO-$d_6$): 10.16 (1H, s), 8.73 (1H, s), 8.57 (1H, d, J=2.9 Hz), 7.77-7.64 (2H, m), 7.22-7.00 (3H, m), 6.79 (1H, s), 3.29-3.22 (1H, m), 2.93-2.82 (1H, m), 2.80-2.70 (1H, m), 2.12 (3H, d, J=2.4 Hz), 1.90-1.79 (1H, m).

Example 16: (S)-1-(3-fluoro-2-methylphenyl)-N-hydroxy-3-(6-(trifluoromethyl)pyridin-3-yl)cyclopent-2-enecarboxamide

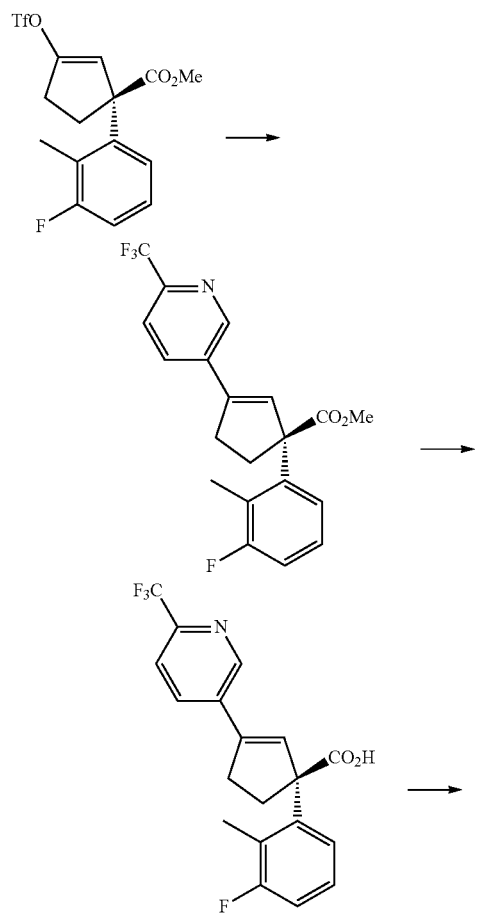

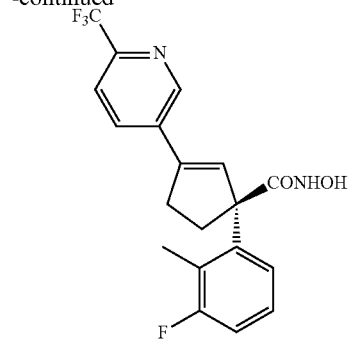

Step 1: (S)-methyl 1-(3-fluoro-2-methylphenyl)-3-(6-(trifluoromethyl)pyridin-3-yl)cyclopent-2-enecarboxylate Following Method B from (S)-methyl 1-(3-fluoro-2-methylphenyl)-3-(((trifluoromethyl)sulfonyl)oxy)cyclopent-2-enecarboxylate (0.25 g, 0.65 mmol), (6-(trifluoromethyl)pyridin-3-yl)boronic acid utilizing CsF, DME, MeOH and palladium tetrakis(triphenylphosphine) under microwave conditions at 120° C. for 1 h. The crude product was triturated with diethyl ether to give the title compound as an orange solid (274 mg). MS (ES+) consistent with target (M+H)+.

Step 2: (S)-1-(3-fluoro-2-methylphenyl)-3-(6-(trifluoromethyl)pyridin-3-yl)cyclopent-2-enecarboxylic Acid Following Method C from (S)-methyl 1-(3-fluoro-2-methylphenyl)-3-(6-(trifluoromethyl)pyridin-3-yl)cyclopent-2-enecarboxylate (274 mg) and used without further purification (193 mg, 80% over two steps). MS (ES+) consistent with target (M+H)+.

Step 3: (S)-1-(3-fluoro-2-methylphenyl)-N-hydroxy-3-(6-(trifluoromethyl)pyridin-3-yl)cyclopent-2-enecarboxamide Following Method D from (S)-1-(3-fluoro-2-methylphenyl)-3-(6-(trifluoromethyl)pyridin-3-yl)cyclopent-2-enecarboxylic acid (193 mg, 0.53 mmol) and purified by recrystallization from DCM to give the title compound as an off white solid (91 mg, 45%). LCMS (ES+) 381 (M+H)+; RT 10.7 min (Analytical method 3). $^1$H NMR δ (ppm) (DMSO-$d_6$): 10.19 (1H, s), 8.98 (1H, s), 8.78 (1H, s), 8.19 (1H, d, J=8.2 Hz), 7.90 (1H, d, J=8.2 Hz), 7.22-7.11 (2H, m), 7.12-7.02 (1H, m), 6.82 (1H, s), 3.25 (1H, ddd, J=13.2, 8.8, 4.4 Hz), 2.98-2.87 (1H, m), 2.82-2.73 (1H, m), 2.13 (3H, d, J=2.5 Hz), 1.97-1.86 (1H, m).

Example 17: (S)-1-(3-fluoro-2-methylphenyl)-N-hydroxy-3-(5-(trifluoromethyl)pyridin-3-yl)cyclopent-2-enecarboxamide

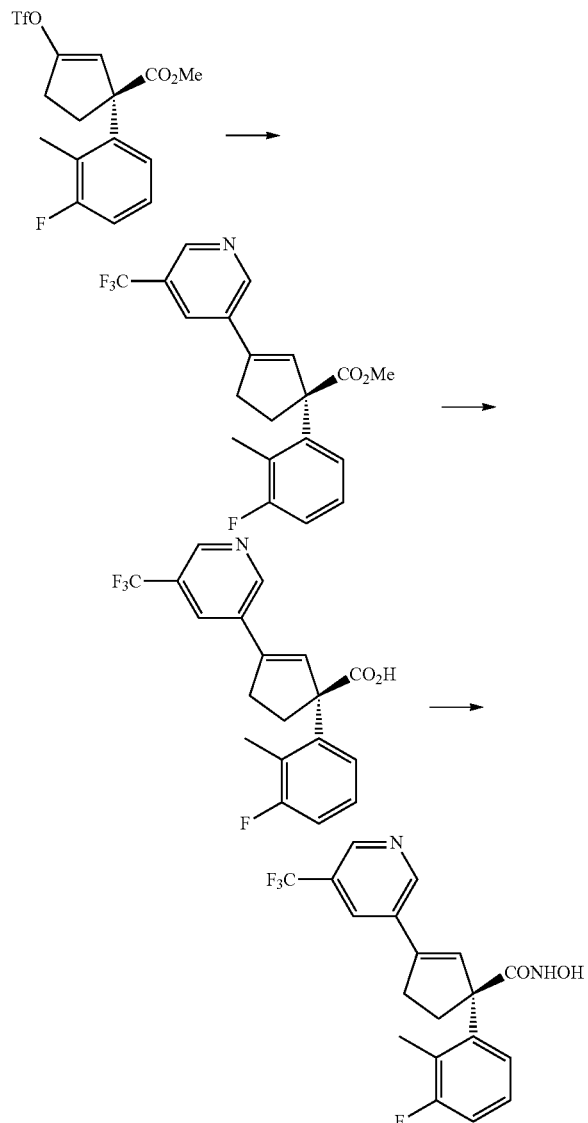

Step 1: (S)-methyl 1-(3-fluoro-2-methylphenyl)-3-(5-(trifluoromethyl)pyridin-3-yl)cyclopent-2-enecarboxylate Following Method B from (S)-methyl 1-(3-fluoro-2-methylphenyl)-3-(((trifluoromethyl)sulfonyl) oxy)cyclopent-2-enecarboxylate (0.25 g, 0.65 mmol) and (5-(trifluoromethyl)pyridin-3-yl)boronic acid utilizing CsF, DME, MeOH and palladium tetrakis(triphenylphosphine) under microwave conditions at 120° C. for 1 h. The crude product (340 mg) was used without further purification in the next step. MS (ES+) consistent with target (M+H)+.

Step 2: (S)-1-(3-fluoro-2-methylphenyl)-3-(5-(trifluoromethyl)pyridin-3-yl)cyclopent-2-enecarboxylic Acid Following Method C from (S)-methyl 1-(3-fluoro-2-methylphenyl)-3-(5-(trifluoromethyl)pyridin-3-yl)cyclopent-2-enecarboxylate (340 mg) and used without further purification (262 mg, 92% over two steps). MS (ES+) consistent with target (M+H)+.

Step 3: (S)-1-(3-fluoro-2-methylphenyl)-N-hydroxy-3-(5-(trifluoromethyl)pyridin-3-yl)cyclopent-2-enecarboxamide Following Method D from (S)-1-(3-fluoro-2-methylphenyl)-3-(5-(trifluoromethyl)pyridin-3-yl)cyclopent-2-enecarboxylic acid (193 mg, 0.53 mmol) and purified by recrystallization from DCM to give the title compound as an off white solid (91 mg, 45%). LCMS (ES+) 381 (M+H)+; RT 10.4 min (Analytical method 3); $^1$H NMR δ (ppm) (DMSO-$d_6$): 10.17 (1H, s), 9.07 (1H, s), 8.91 (1H, s), 8.79 (1H, s), 8.37 (1H, s), 7.24-7.14 (2H, m), 7.12-7.04 (1H, m), 6.88 (1H, s), 3.29-3.19 (1H, m), 3.04-2.92 (1H, m), 2.87-2.77 (1H, m), 2.16 (3H, d, J=2.5 Hz), 2.01-1.90 (1H, m).

Example 18: (S)-3-(1-(difluoromethyl)-1H-pyrazol-4-yl)-1-(3-fluoro-2-methylphenyl)-N-hydroxycyclopent-2-enecarboxamide

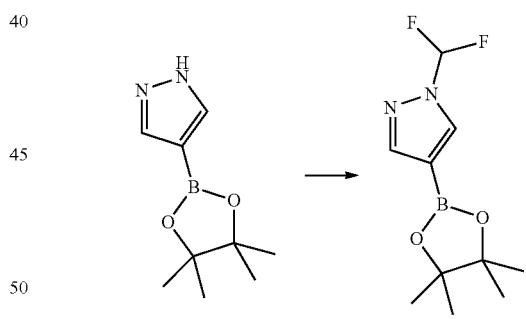

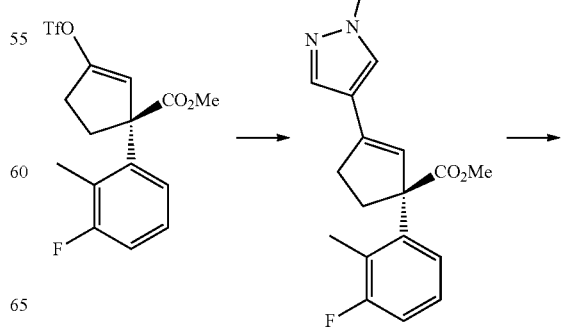

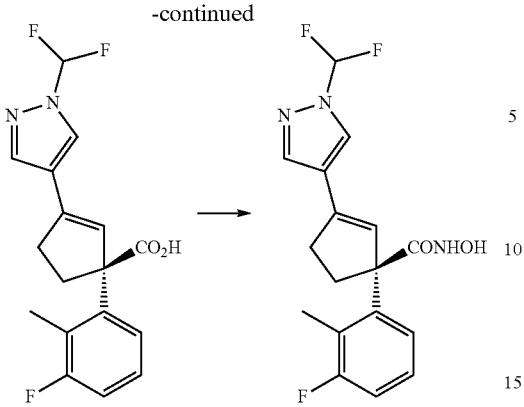

Step 1: 1-(difluoromethyl)-4-(4,4,5,5-tetramethyl-1,3,2-dioxaborolan-2-yl)-1H-pyrazole A 100 mL round bottom flask was charged with 4-pyrazoleboronic acid pinacol ester (1.0 g, 5.15 mmol), 18-crown-6 (0.27 g, 1.03 mmol) and anhydrous acetonitrile (25 mL). The reagents were stirred until a colorless solution formed then sodium chlorodifluoroacetate (0.94 g, 6.18 mmol) was added and the reaction mixture heated to reflux for 18 h. After this time the reaction mixture was cooled to r.t. and the precipitated solid removed by filtration through celite, washing with EtOAc (3×20 mL). Combined organics were filtered through a hydrophobic frit and condensed to give a pale yellow oil. The crude product was purified by flash silica column chromatography (gradient elution iso-hexane to 33% EtOAc in iso-hexane) to give the title compound as a colorless solid (1.06 g, 84%). MS (ES+) consistent with target (M+H)+.

Step 2: (S)-methyl 3-(1-(difluoromethyl)-1H-pyrazol-4-yl)-1-(3-fluoro-2-methylphenyl)cyclopent-2-enecarboxylate Following Method B from (S)-methyl 1-(3-fluoro-2-methylphenyl)-3-(((trifluoromethyl)sulfonyl) oxy)cyclopent-2-enecarboxylate (0.15 g, 0.40 mmol) and 1-(difluoromethyl)-4-(4,4,5,5-tetramethyl-1,3,2-dioxaborolan-2-yl)-1H-pyrazole (0.10 g, 0.41 mmol). The crude product was purified by flash silica column chromatography (gradient elution iso-hexane to 33% EtOAc in iso-hexane) to give the title compound as a colorless oil (0.12 g, 77%). MS (ES+) consistent with target (M+H)+.

Step 3: (S)-3-(1-(difluoromethyl)-1H-pyrazol-4-yl)-1-(3-fluoro-2-methylphenyl)cyclopent-2-enecarboxylic Acid Following Method C (ii) from (S)-methyl 3-(1-(difluoromethyl)-1H-pyrazol-4-yl)-1-(3-fluoro-2-methylphenyl)cyclopent-2-enecarboxylate (0.05 g, 0.14 mmol) to give a colorless residue which crystallized on standing (0.43 g, 89%). MS (ES+) consistent with target (M+H)+.

Step 4: (S)-3-(1-(difluoromethyl)-1H-pyrazol-4-yl)-1-(3-fluoro-2-methylphenyl)-N-hydroxycyclopent-2-enecarboxamide Following Method D from (S)-3-(1-(difluoromethyl)-1H-pyrazol-4-yl)-1-(3-fluoro-2-methylphenyl)cyclopent-2-enecarboxylic acid (0.04 g, 0.12 mmol) and purified by preparative HPLC (22 mg, 52%). LCMS (ES+) 352 (M+H)+; RT 3.57 min (Analytical method 1); 1H NMR δ (ppm) (DMSO-d6): 10.17 (1H, s), 8.78 (1H, s), 8.42 (1H, s), 8.15 (1H, s), 7.85 (1H, t, J=59.2 Hz), 7.23-7.07 (3H, m), 6.33 (1H, s), 3.27-3.20 (1H, m), 2.84-2.78 (1H, m), 2.68-2.59 (1H, m), 2.16 (3H, d, J=2.4 Hz), 1.88-1.83 (1H, m).

Example 19: (S)-3-(2-cyclopropyl-5-fluoropyridin-3-yl)-1-(3-fluoro-2-methylphenyl)-N-hydroxycyclopent-2-enecarboxamide

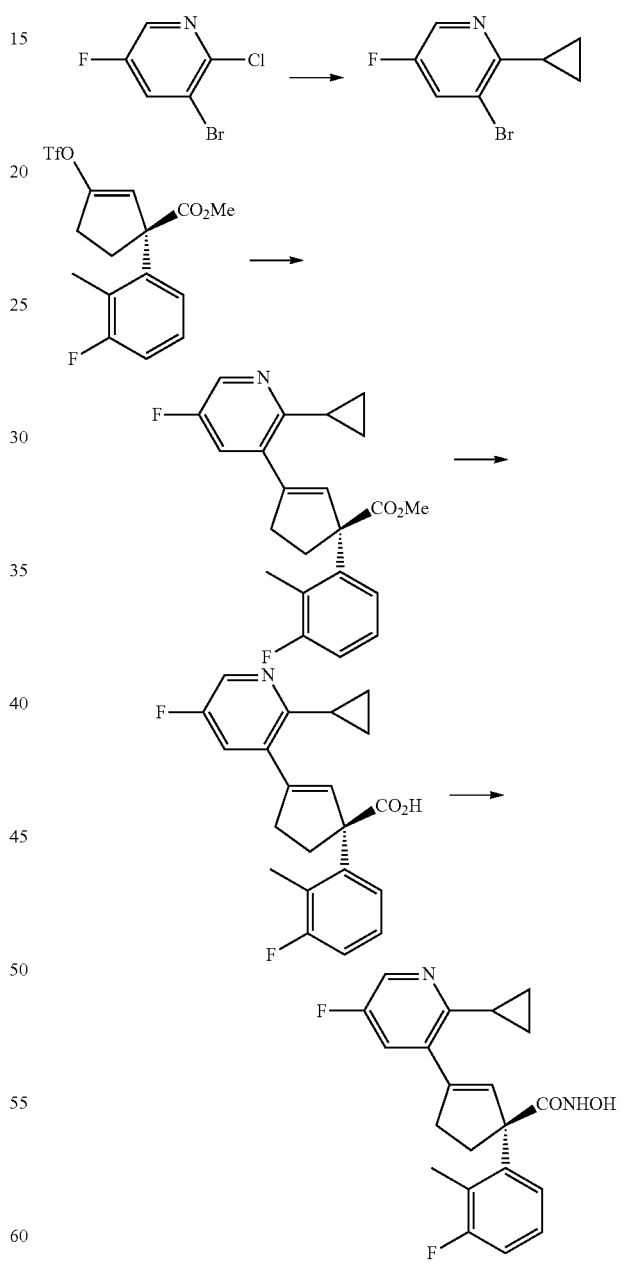

Step 1: 3-bromo-2-cyclopropyl-5-fluoropyridine

To a solution of 3-bromo-2-chloro-5-fluoropyridine (760 mg, 3.62 mmol) in THF (3 mL) was added a solution of cyclopropylzinc bromide in THF (0.5 M, 8 mL, 4 mmol) and Pd(PPh₃)₄ (125 mg) and the reaction mixture was stirred at 20° C. overnight. Additional cyclopropylzinc bromide (0.5 M, 4 mL, 2 mmol) and Pd(PPh₃)₄ (65 mg) was needed to consume all starting material. The reaction mixture was stirred at 20° C. for an additional 6 h, then it was partitioned between EtOAc (30 mL) and 1 M HCl (15 mL). The organic layer was separated, washed with brine (40 mL), dried, filtered (phase separation cartridge) and concentrated. Purification by flash column chromatography (SNAP column 25 g, iso-hexane-EtOAc: 0-25%) gave the title compound as a yellow oil (401 mg, 51%).

Step 2: (S)-methyl-3-(2-cyclopropyl-5-fluoropyridin-3-yl)-1-(3-fluoro-2-methylphenyl)cyclopent-2-enecarboxylate Following Method B (iii) from (S)-methyl-1-(3-fluoro-2-methylphenyl)-3-(((trifluoromethyl)sulfonyl) oxy)cyclopent-2-enecarboxylate (0.54 g, 1.4 mmol) and 3-bromo-2-cyclopropyl-5-fluoropyrimidine (0.40 g, 1.86 mmol). The crude product was purified by flash column chromatography to give the title compound as pale yellow oil (301 mg, 58%). MS (ES+) consistent with target (M+H)⁺.

Step 3: (S)-3-(2-cyclopropyl-5-fluoropyridin-3-yl)-1-(3-fluoro-2-methylphenyl)cyclopent-2-enecarboxylic Acid Following Method C from (S)-methyl-3-(2-cyclopropyl-5-fluoropyridin-3-yl)-1-(3-fluoro-2-methylphenyl)cyclopent-2-enecarboxylate (300 mg, 0.81 mmol). The crude product (250 mg) was used without further purification. MS (ES+) consistent with target (M+H)⁺.

Step 4: (S)-3-(2-cyclopropyl-5-fluoropyridin-3-yl)-1-(3-fluoro-2-methylphenyl)-N-hydroxycyclopent-2-enecarboxamide Following Method D from (S)-3-(2-cyclopropyl-5-fluoropyridin-3-yl)-1-(3-fluoro-2-methylphenyl)cyclopent-2-enecarboxylic acid (250 mg, 0.70 mmol) and purified by preparative HPLC to give the title compound as a white solid (62 mg, 24%). LCMS (ES+) 371 (M+H)⁺; RT 10.6 min (Analytical method 3); ¹H NMR δ (ppm) (DMSO-d₆): 10.07 (1H, s), 8.65 (1H, d, J=1.5 Hz), 8.31 (1H, d, J=2.7 Hz), 7.34 (1H, dd, J=10.3, 2.8 Hz), 7.16-6.95 (3H, m), 6.51 (1H, s), 3.18 (1H, m), 2.98-2.88 (1H, m), 2.78-2.69 (1H, m), 2.12-2.05 (4H, m), 1.71 (1H, m), 1.03-0.97 (2H, m), 0.82-0.71 (2H, m).

Example 20: (S)-1-(3-fluoro-2-methylphenyl)-N-hydroxy-3-(2-(trifluoromethyl)quinoxalin-6-yl)cyclopent-2-enecarboxamide

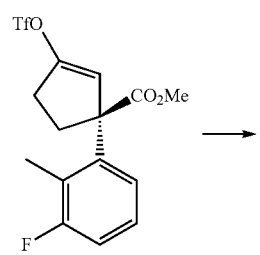

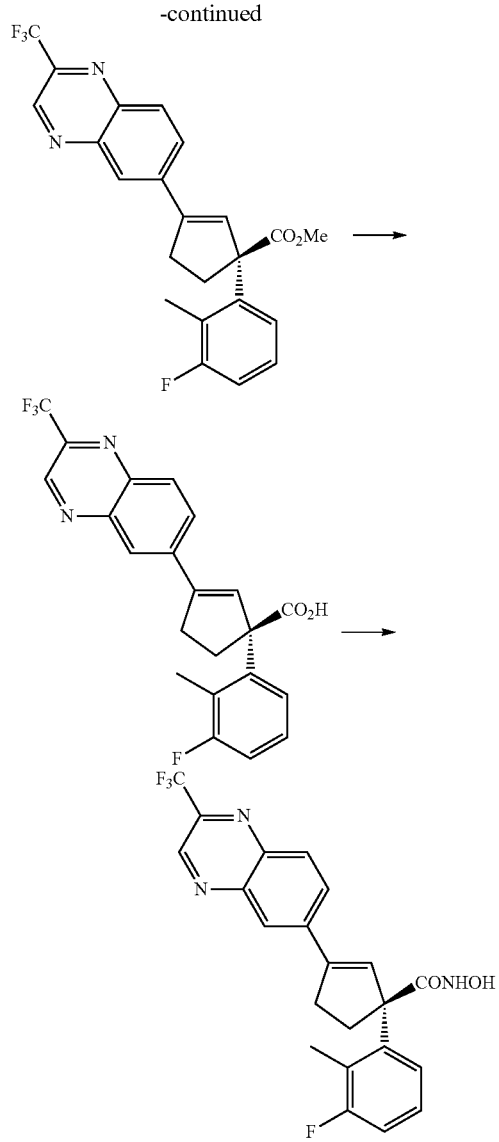

Step 1: (S)-methyl-1-(3-fluoro-2-methylphenyl)-3-(2-(trifluoromethyl)quinoxalin-6-yl)cyclopent-2-enecarboxylate Following Method B (iii) from (S)-methyl-1-(3-fluoro-2-methylphenyl)-3-(((trifluoromethyl)sulfonyl) oxy)cyclopent-2-enecarboxylate (0.65 g, 1.7 mmol) and a mixture of 7 & 6-bromo-2-(trifluoromethyl)quinoxaline (0.53 g, 1.88 mmol). The crude product was purified by flash column chromatography to give the title compound as pale yellow oil (230 mg, 57%). MS (ES+) consistent with target (M+H)⁺.

Step 2: (S)-1-(3-fluoro-2-methylphenyl)-3-(2-(trifluoromethyl)quinoxalin-6-yl)cyclopent-2-enecarboxylic Acid Following Method C from (S)-methyl-1-(3-fluoro-2-methylphenyl)-3-(2-(trifluoromethyl)quinoxalin-6-yl)cyclopent-2-enecarboxylate (230 mg, 0.53 mmol) and used without further purification (210 mg). MS (ES+) consistent with target (M+H)⁺.

Step 3: (S)-1-(3-fluoro-2-methylphenyl)-N-hydroxy-3-(2-(trifluoromethyl)quinoxalin-6-yl)cyclopent-2-enecarboxamide Following Method D from (S)-1-(3-fluoro-2-methylphenyl)-3-(2-(trifluoromethyl)quinoxalin-6-yl)cyclopent-2-enecarboxylic acid (210 mg, 0.51 mmol) and purified by preparative HPLC to give the title compound as an off-white solid (60 mg, 28%). LCMS (ES+) 432 (M+H)+; RT 4.23 min (Analytical method 1); $^1$H NMR δ (ppm) (DMSO-$d_6$): 10.28 (1H, s), 9.46 (1H, s), 8.85 (1H, s), 8.49 (1H, d, J=9.0 Hz), 8.31 (1H, d, J=8.9 Hz), 8.25 (1H, s), 7.28-7.22 (2H, m), 7.16-7.09 (1H, m), 7.01 (1H, s), 3.41-3.32 (1H obscured by water), 3.15-3.02 (1H, m), 3.01-2.88 (1H, m), 2.22 (3H, s), 2.06-1.96 (1H, m).

Example 21: (S)-1-(3-fluoro-2-methylphenyl)-N-hydroxy-3-(imidazo[1,2-a]pyridin-7-yl)cyclopent-2-enecarboxamide

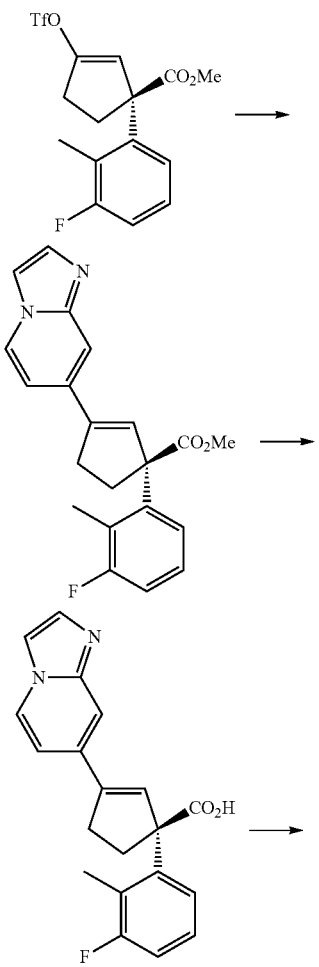

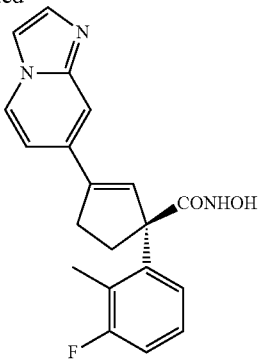

Step 1: (S)-methyl 1-(3-fluoro-2-methylphenyl)-3-(imidazo[1,2-a]pyridin-7-yl)cyclopent-2-enecarboxylate Following Method B (iii) from (S)-methyl 1-(3-fluoro-2-methylphenyl)-3-(((trifluoromethyl)sulfonyl) oxy)cyclopent-2-enecarboxylate (0.3 g, 0.78 mmol) and 7-bromoimidazo[1,2-a]pyridine (0.169 g, 0.86 mmol). The crude product was purified by flash column chromatography to give the title compound as a pale yellow gum (157 mg, 57%). MS (ES+) consistent with target (M+H)+.

Step 2: (S)-1-(3-fluoro-2-methylphenyl)-3-(imidazo[1,2-a]pyridin-7-yl)cyclopent-2-enecarboxylic Acid Following Method C from (S)-methyl 1-(3-fluoro-2-methylphenyl)-3-(imidazo[1,2-a]pyridin-7-yl)cyclopent-2-enecarboxylate (217 mg). The crude product was obtained as an off white solid (156 mg) and used without further purification. MS (ES+) consistent with target (M+H)+.

Step 3: (S)-1-(3-fluoro-2-methylphenyl)-N-hydroxy-3-(imidazo[1,2-a]pyridin-7-yl)cyclopent-2-enecarboxamide Following Method D from (S)-1-(3-fluoro-2-methylphenyl)-3-(imidazo[1,2-a]pyridin-7-yl)cyclopent-2-enecarboxylic acid (156 mg, 0.46 mmol) and purified by preparative HPLC to give the title compound as an off white solid (52 mg, 31%). LCMS (ES+) 352 (M+H)+; RT 2.39 min (Analytical method 1); $^1$H NMR δ (ppm) (DMSO-$d_6$): 10.16 (1H, s), 8.78 (1H, s), 8.52 (1H, d, J=7.1 Hz), 7.95 (1H, s), 7.58 (1H, d, J=1.2 Hz), 7.49 (1H, s), 7.28-7.14 (3H, m), 7.10-7.02 (1H, m), 6.65 (1H, s), 3.29-3.22 (1H, m), 2.97-2.86 (1H, m), 2.83-2.73 (1H, m), 2.15 (3H, d, J=2.5 Hz), 1.94-1.84 (1H, m).

Example 22: (S)-1-(3-fluoro-2-methylphenyl)-N-hydroxy-3-(3-methylbenzo[d]isoxazol-5-yl)cyclopent-2-enecarboxamide

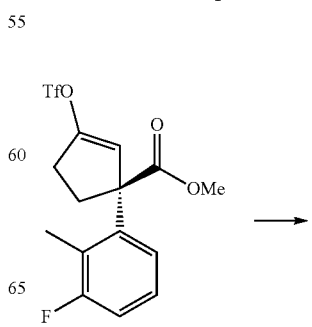

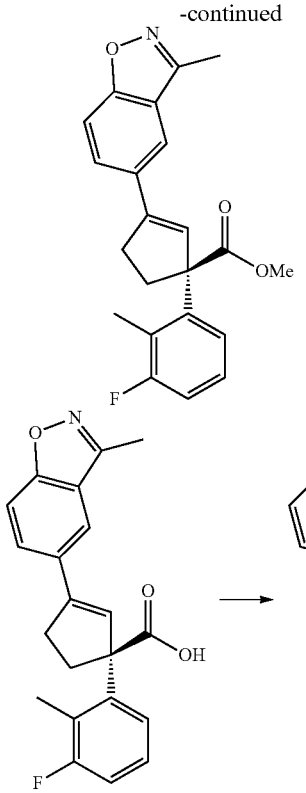

8.75 (1H, s), 7.95 (1H, s), 7.89 (1H, dd, J=8.8, 1.7 Hz), 7.69 (1H, d, J=8.8 Hz), 7.18-7.14 (2H, m), 7.08-7.01 (1H, m), 6.54 (1H, s), 3.30-3.22 (1H, m), 2.97-2.87 (1H, m), 2.82-2.72 (1H, m), 2.57 (3H, s), 2.13 (3H, d, J=2.4 Hz), 1.87 (1H, ddd, J=13.0, 9.1, 6.1 Hz).

Example 23: (S)-1-(3-fluoro-2-methylphenyl)-3-(5-fluoro-6-methoxypyridin-3-yl)-N-hydroxycyclopent-2-enecarboxamide

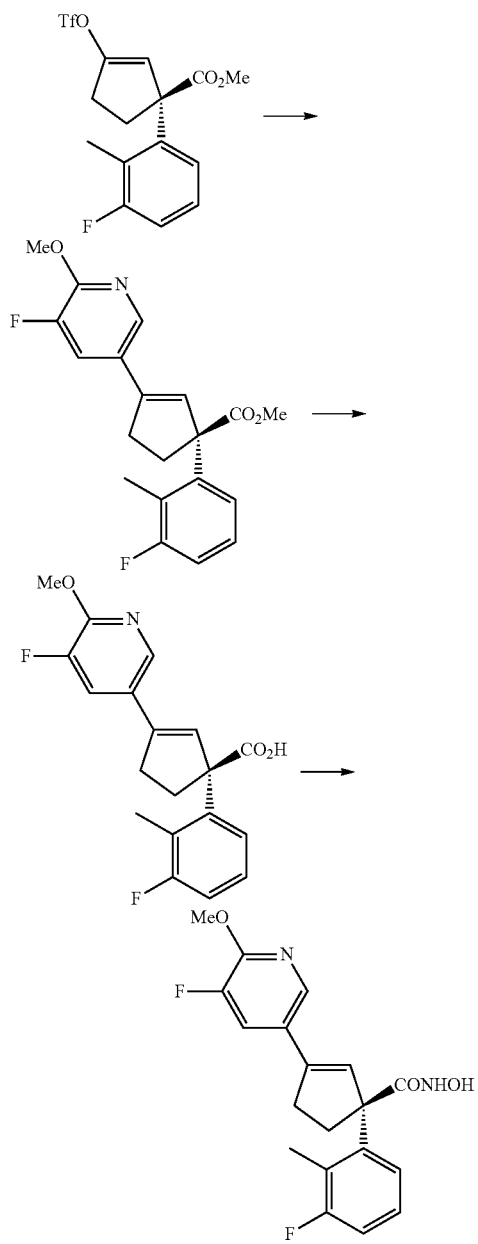

Step 1: (S)-methyl 1-(3-fluoro-2-methylphenyl)-3-(3-methylbenzo[d]isoxazol-5-yl)cyclopent-2-ene Carboxylate Following Method B from (S)-methyl-1-(3-fluoro-2-methylphenyl)-3-(((trifluoromethyl)sulfonyl) oxy)cyclopent-2-enecarboxylate (0.15 g, 0.40 mmol) and 3-methyl-5-(4,4,5,5-tetramethyl-1,3,2-dioxaborolan-2-yl)benzo[d]isoxazole (0.11 g, 0.42 mmol). The crude product was purified by flash silica column chromatography (gradient elution iso-hexane to 20% EtOAc in iso-hexane) to give the title compound as a colorless oil (0.12 g, 82%). MS (ES+) consistent with target (M+H)+.

Step 2: (S)-1-(3-fluoro-2-methylphenyl)-3-(3-methylbenzo[d]isoxazol-5-yl)cyclopent-2-enecarboxylic Acid Following Method C (ii) from (S)-methyl 1-(3-fluoro-2-methylphenyl)-3-(3-methylbenzo[d]isoxazol-5-yl)cyclopent-2-enecarboxylate (0.12 g, 0.33 mmol) to give a colorless solid (0.09 g, 81%). MS (ES+) consistent with target (M+H)+.

Step 3: (S)-1-(3-fluoro-2-methylphenyl)-N-hydroxy-3-(3-methylbenzo[d]isoxazol-5-yl)cyclopent-2-enecarboxamide Following Method D from (S)-1-(3-fluoro-2-methylphenyl)-3-(3-methylbenzo[d]isoxazol-5-yl)cyclopent-2-enecarboxylic acid (0.09 g, 0.26 mmol) and purified by preparative HPLC to give the title compound as a white solid (0.06 g, 63%). LCMS (ES+) 367 (M+H)+; RT 3.82 min (Analytical method 1); $^1$H NMR δ (ppm) (DMSO-$d_6$): 10.14 (1H, s), Step 1: (S)-methyl 1-(3-fluoro-2-methylphenyl)-3-(5-fluoro-6-methoxypyridin-3-yl)cyclopent-2-enecarboxylate Following Method B from (S)-methyl 1-(3-fluoro-2-methylphenyl)-3-((((trifluoromethyl)sulfonyl) oxy)cyclopent-2-enecarboxylate (500 mg, 1.31 mmol) and 2-methoxy-3-fluoropyridine-5-boronic acid utilizing CsF, DME, MeOH and palladium tetrakis(triphenylphosphine) at 120° C. The crude product was purified by flash column chromatography to give the title compound as a clear gum (385 mg, 82%). MS (ES+) consistent with target (M+H)+.

Step 2: (S)-1-(3-fluoro-2-methylphenyl)-3-(5-fluoro-6-methoxypyridin-3-yl)cyclopent-2-enecarboxylic Acid Following Method C from (S)-methyl 1-(3-fluoro-2-methylphenyl)-3-(5-fluoro-6-methoxypyridin-3-yl)cyclopent-2-enecarboxylate (190 mg) and used without further purification (149 mg). MS (ES+) consistent with target (M+H)+.

Step 3: (S)-1-(3-fluoro-2-methylphenyl)-3-(5-fluoro-6-methoxypyridin-3-yl)-N-hydroxycyclopent-2-enecarboxamide Following Method D from (S)-1-(3-fluoro-2-methylphenyl)-3-(5-fluoro-6-methoxypyridin-3-yl)cyclopent-2-enecarboxylic acid (148 mg, 0.43 mmol) and purified by preparative HPLC to give the title compound as a white solid (76 mg, 49%). LCMS (ES+) 361 (M+H)+; RT 3.75 min (Analytical method 1); $^1$H NMR δ (ppm) (DMSO-$d_6$): 10.17 (1H, s), 8.79 (1H, s), 8.15 (1H, d, J=1.6 Hz), 8.03 (1H, dd, J=1.6 Hz, J=11.6 Hz), 7.22-7.18 (2H, m), 7.15-7.05 (1H, m), 6.57 (1H, s), 4.02 (3H, s), 3.35-3.25 (1H, m), 2.95-2.85 (1H, m), 2.80-2.65 (1H, m), 2.18 (3H, d, J=2.4 Hz), 1.99-1.92 (1H, m).

Example 24: (S)-3-(2-cyclopropylpyrimidin-5-yl)-1-(3-fluoro-2-methylphenyl)-N-hydroxycyclopent-2-enecarboxamide

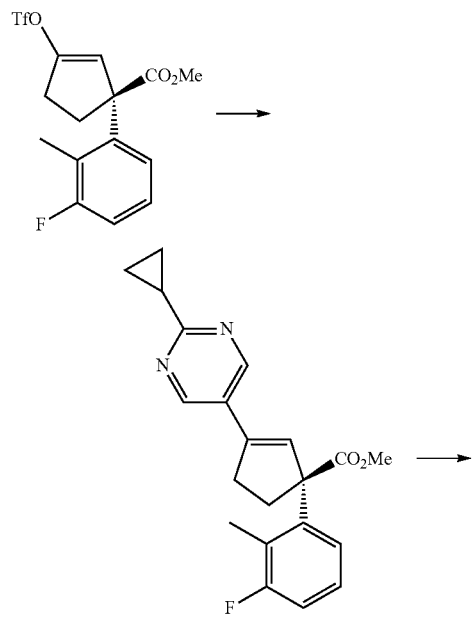

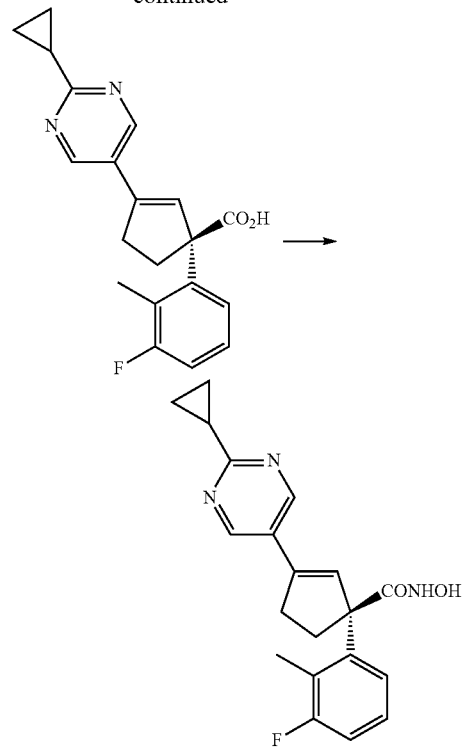

Step 1: (S)-methyl 3-(2-cyclopropylpyrimidin-5-yl)-1-(3-fluoro-2-methylphenyl)cyclopent-2-enecarboxylate Following Method B from (S)-methyl 1-(3-fluoro-2-methylphenyl)-3-(((trifluoromethyl)sulfonyl) oxy)cyclopent-2-enecarboxylate (300 mg, 0.79 mmol) and 2-cyclopropylpyrimidine-5-boronic acid utilizing CsF, DME, MeOH and palladium tetrakis(triphenylphosphine) at 120° C. The crude product was purified by flash column chromatography to give the title compound as a clear oil (191 mg, 69%). MS (ES+) consistent with target (M+H)+.

Step 2: (S)-3-(2-cyclopropylpyrimidin-5-yl)-1-(3-fluoro-2-methylphenyl)cyclopent-2-enecarboxylic Acid Following Method C from (S)-methyl 3-(2-cyclopropylpyrimidin-5-yl)-1-(3-fluoro-2-methylphenyl)cyclopent-2-enecarboxylate (190 mg) and used without further purification (160 mg). MS (ES+) consistent with target (M+H)+.

Step 3: (S)-3-(2-cyclopropylpyrimidin-5-yl)-1-(3-fluoro-2-methylphenyl)-N-hydroxycyclopent-2-enecarboxamide Following Method D from (S)-3-(2-cyclopropylpyrimidin-5-yl)-1-(3-fluoro-2-methylphenyl)cyclopent-2-enecarboxylic acid (154 mg, 0.46 mmol) and purified by preparative HPLC to give the title compound as a white solid (93 mg, 58%). LCMS (ES+) 354 (M+H)+; RT 3.51 min (Analytical method 1); $^1$H NMR δ (ppm) (DMSO-$d_6$): 10.16 (1H, s), 8.82 (2H, s), 8.77 (1H, s), 7.18-7.14 (2H, m), 7.08-7.05 (1H, m), 6.65 (1H, s), 3.30-3.20 (1H, m), 2.95-2.85 (1H, m), 2.80-2.65 (1H, m), 2.27-2.19 (1H, m), 2.20 (3H, d, J=2.3 Hz), 1.95-1.85 (1H, m), 1.1-0.98 (4H, m).

Example 25: (S)-1-(3-fluoro-2-methylphenyl)-N-hydroxy-3-(6-methylpyridin-3-yl)cyclopent-2-enecarboxamide Example 26: (S)-3-(5-chloro-6-methylpyridin-3-yl)-1-(3-fluoro-2-methylphenyl)-N-hydroxycyclopent-2-enecarboxamide

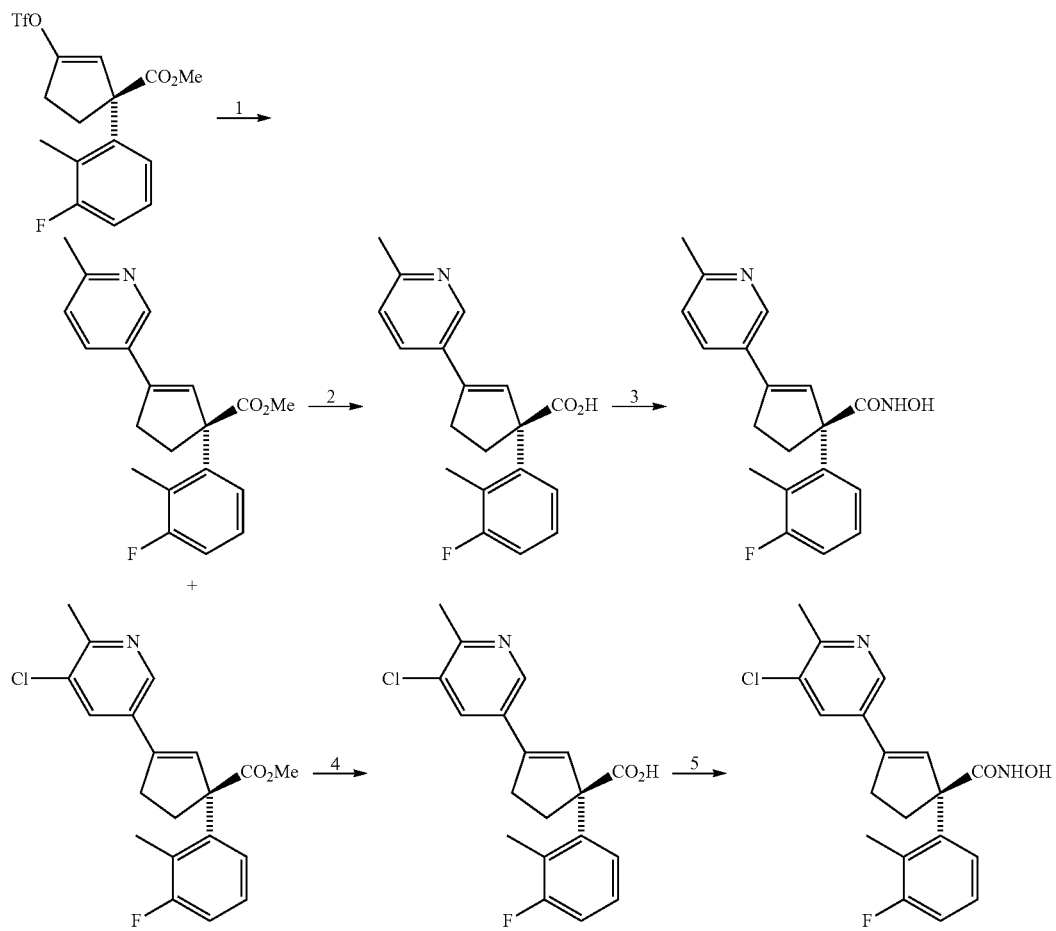

Step 1: (S)-methyl 1-(3-fluoro-2-methylphenyl)-3-(6-methylpyridin-3-yl)cyclopent-2-enecarboxylate and (S)-methyl 3-(5-chloro-6-methylpyridin-3-yl)-1-(3-fluoro-2-methylphenyl)cyclopent-2-enecarboxylate Following Method B from (S)-methyl 1-(3-fluoro-2-methylphenyl)-3-(((trifluoromethyl)sulfonyl) oxy)cyclopent-2-enecarboxylate (300 mg, 0.79 mmol) and 2-methyl-3-chloropyridine-5-boronic acid utilizing CsF, DME, MeOH and palladium tetrakis(triphenylphosphine) at 120° C. The crude material was purified by flash column chromatography to give the title compounds as clear oils (24 mg and 180 mg). MS (ES+) consistent with targets (M+H)⁺.

Step 2: (S)-1-(3-fluoro-2-methylphenyl)-3-(6-methylpyridin-3-yl)cyclopent-2-enecarboxylic Acid Following Method C from (S)-methyl 1-(3-fluoro-2-methylphenyl)-3-(6-methylpyridin-3-yl)cyclopent-2-enecarboxylate (170 mg) and used without further purification (172 mg). MS (ES+) consistent with target (M+H)⁺.

Step 3: (S)-1-(3-fluoro-2-methylphenyl)-N-hydroxy-3-(6-methylpyridin-3-yl)cyclopent-2-enecarboxamide Following Method D from (S)-1-(3-fluoro-2-methylphenyl)-3-(6-methylpyridin-3-yl)cyclopent-2-enecarboxylic acid (172 mg, 0.46 mmol) and purified by preparative HPLC to give the title compound as a white solid (72 mg, 48%). LCMS (ES+) 327 (M+H)⁺; RT 2.53 min (Analytical method 1); ¹H NMR δ (ppm) (DMSO-d₆): 10.14 (1H, s), 8.75 (1H, s), 8.57 (1H, s), 8.35 (1H, s), 8.14 (1H, s), 7.25-7.05 (3H, m), 6.61 (1H, s), 3.30-3.20 (1H, m), 2.95-2.85 (1H, m), 2.75-2.65 (1H, m), 2.31 (3H, s), 2.16 (3H, d, J=2.8 Hz), 1.95-1.80 (1H, m).

Step 4: (S)-3-(5-chloro-6-methylpyridin-3-yl)-1-(3-fluoro-2-methylphenyl)cyclopent-2-enecarboxylic Acid Following Method C from (S)-methyl 3-(5-chloro-6-methylpyridin-3-yl)-1-(3-fluoro-2-methylphenyl)cyclopent-2-enecarboxylate (350 mg) and used without further purification (199 mg). MS (ES+) consistent with target (M+H)+.

Step 5: (S)-3-(5-chloro-6-methylpyridin-3-yl)-1-(3-fluoro-2-methylphenyl)-N-hydroxycyclopent-2-enecarboxamide Following Method D from (S)-3-(5-chloro-6-methylpyridin-3-yl)-1-(3-fluoro-2-methylphenyl)cyclopent-2-enecarboxylic acid (199 mg, 0.58 mmol) and purified by preparative HPLC to give the title compound as a white solid (137 mg, 66%). LCMS (ES+) 361/363 (M+H)+, RT 10.6 min (Analytical method 3); $^1$H NMR δ (ppm) (DMSO-$d_6$): 10.16 (1H, s), 8.76 (1H, s), 8.41 (1H, s), 8.03 (1H, s), 7.25-7.05 (3H, m), 6.65 (1H, s), 3.30-3.20 (1H, m), 2.95-2.85 (1H, m), 2.75-2.65 (1H, m), 2.38 (3H, s), 2.16 (3H, d, J=2.8 Hz), 1.95-1.80 (1H, m).

Example 27: (S)-1-(3-fluoro-2-methylphenyl)-N-hydroxy-3-(1-methyl-1H-pyrazol-5-yl)cyclopent-2-enecarboxamide

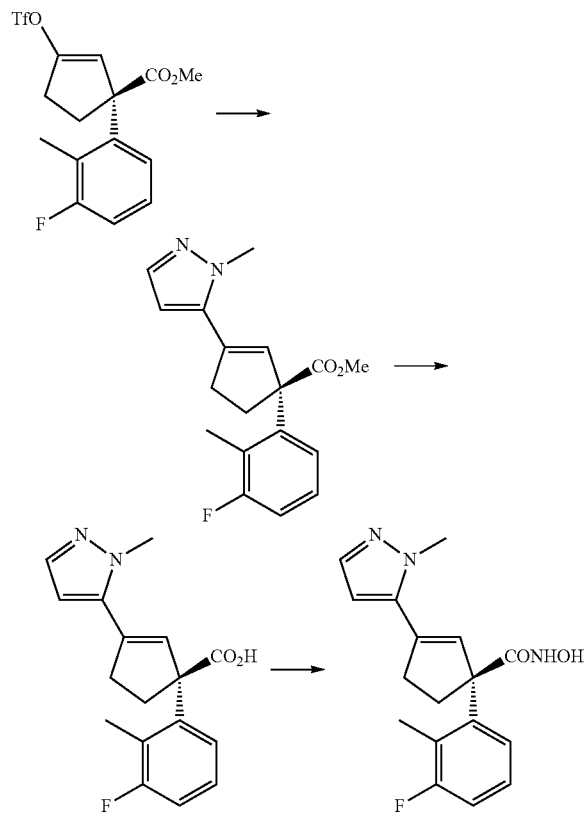

Step 1: (S)-methyl 1-(3-fluoro-2-methylphenyl)-3-(1-methyl-1H-pyrazol-5-yl)cyclopent-2-enecarboxylate Following Method B from (S)-methyl 1-(3-fluoro-2-methylphenyl)-3-(((trifluoromethyl)sulfonyl) oxy)cyclopent-2-enecarboxylate (300 mg, 0.79 mmol) and (1-methyl-1H-pyrazol-5-yl)boronic acid utilizing CsF, DME, MeOH and palladium tetrakis(triphenylphosphine) at 120° C. The crude product was purified by flash column chromatography to give the title compound as a clear oil (221 mg). MS (ES+) consistent with target (M+H)+.

Step 2: (S)-1-(3-fluoro-2-methylphenyl)-3-(1-methyl-1H-pyrazol-5-yl)cyclopent-2-enecarboxylic Acid Following Method C from (S)-methyl 1-(3-fluoro-2-methylphenyl)-3-(1-methyl-1H-pyrazol-5-yl)cyclopent-2-enecarboxylate (220 mg) and the impure crude material used without further purification (313 mg). MS (ES+) consistent with target (M+H)+.

Step 3: (S)-1-(3-fluoro-2-methylphenyl)-N-hydroxy-3-(1-methyl-1H-pyrazol-5-yl)cyclopent-2-enecarboxamide Following Method D from (S)-1-(3-fluoro-2-methylphenyl)-3-(1-methyl-1H-pyrazol-5-yl)cyclopent-2-enecarboxylic acid (200 mg, 0.66 mmol) and purified by preparative HPLC to give the title compound as a white solid (16 mg, 8%). LCMS (ES+) 316 (M+H)+, RT 3.15 min (Analytical method 1); $^1$H NMR δ (ppm) (DMSO-$d_6$): 10.13 (1H, s), 8.76 (1H, s), 7.40 (1H, s), 7.25-7.05 (3H, m), 6.34 (1H, s), 4.00 (3H, s), 3.30-3.20 (1H, m), 2.95-2.85 (1H, m), 2.75-2.65 (1H, m), 2.18 (3H, d, J=2.8 Hz), 1.85-1.75 (1H, m). 1H obscured by DMSO.

Example 28: (S)-1-(3-fluoro-2-methylphenyl)-N-hydroxy-3-(1-(2,2,2-trifluoroethyl)-1H-pyrazol-4-yl)cyclopent-2-enecarboxamide

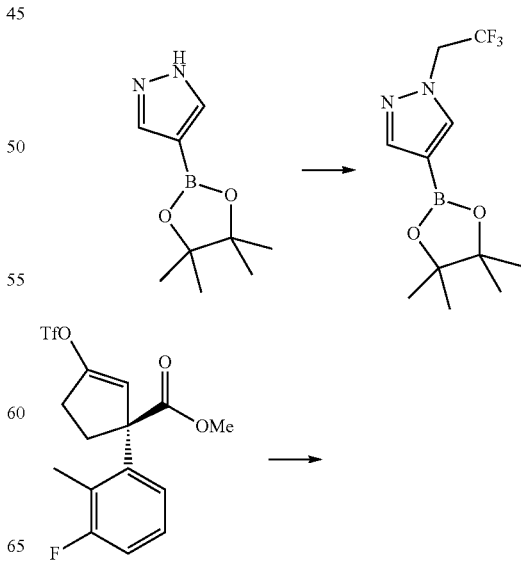

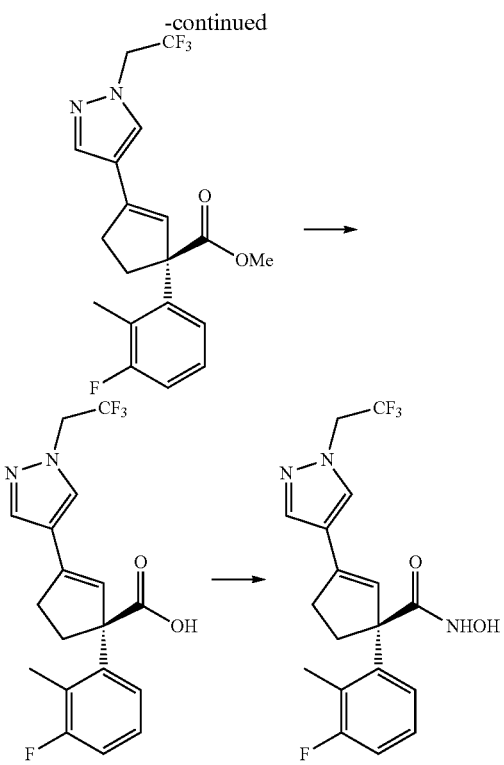

Step 1: 4-(4,4,5,5-tetramethyl-1,3,2-dioxaborolan-2-yl)-1-(2,2,2-trifluoroethyl)-1H-pyrazole A 25 mL teflon cap tube was charged with 4-pyrazoleboronic acid pinacol ester (0.94 g, 4.87 mmol), cesium carbonate (2.58 g, 7.31 mmol), 2,2,2 trifluoroethyl methanesulfonate (1.30 g, 0.86 mL, 7.31 mmol) and anhydrous DMF (8 mL). The reagents were capped under $N_2$ and heated at 100° C. under microwave irradiation for 1 h. After this time the reaction mixture was cooled to rt and partitioned with EtOAc (60 mL) and water (100 mL). Organic layers were extracted, washed with brine (2×65 mL), then dried and filtered (phase separator) to give a pale yellow oil. The crude product was purified by flash silica column chromatography (gradient elution iso-hexane to 33% EtOAc in iso-hexane) to give the title compound as a colorless oil (0.37 g, 35%—mixture of target material and 2,2,2 trifluoroethyl methanesulfonate 1:2). MS (ES+) consistent with target (M+H)$^+$.

Step 2: (S)-methyl 1-(3-fluoro-2-methylphenyl)-3-(1-(2,2,2-trifluoroethyl)-1H-pyrazol-4-yl)cyclopent-2-enecarboxylate Following Method B from (S)-methyl 1-(3-fluoro-2-methylphenyl)-3-(((trifluoromethyl)sulfonyl) oxy)cyclopent-2-enecarboxylate (0.15 g, 0.40 mmol) and 4-(4,4,5,5-tetramethyl-1,3,2-dioxaborolan-2-yl)-1-(2,2,2-trifluoroethyl)-1H-pyrazole (0.33 g, 1.2 mmol, 30% purity). The crude product was purified by flash silica column chromatography (gradient elution iso-hexane to 33% EtOAc in iso-hexane) to give the title compound as a colorless oil (0.32 g, 77%, 1:1 mixture of TM and 2,2,2 trifluoroethyl methanesulfonate). MS (ES+) consistent with target (M+H)$^+$.

Step 3: (S)-1-(3-fluoro-2-methylphenyl)-3-(1-(2,2,2-trifluoroethyl)-1H-pyrazol-4-yl)cyclopent-2-enecarboxylic Acid Following Method C (ii) from (S)-methyl 1-(3-fluoro-2-methylphenyl)-3-(1-(2,2,2-trifluoroethyl)-1H-pyrazol-4-yl)cyclopent-2-enecarboxylate (0.32 g, 0.84 mmol, 50% purity) as far as removal of methanol under reduced pressure. Aqueous residues were then partitioned between $CH_2Cl_2$ (15 mL) and water (15 mL). Organic layers were discarded and basic aqueous layers acidified to pH=3 (1 M HCl). Acidic aqueous layers were then partitioned with EtOAc (20 mL). Organic layers were extracted, washed with brine (20 mL), dried, filtered (phase separation cartridge) and concentrated to give a colorless oil (0.13 g, 82%). MS (ES+) consistent with target (M+H)$^+$.

Step 4: (S)-1-(3-fluoro-2-methylphenyl)-N-hydroxy-3-(1-(2,2,2-trifluoroethyl)-1H-pyrazol-4-yl)cyclopent-2-enecarboxamide Following Method D from (S)-1-(3-fluoro-2-methylphenyl)-3-(1-(2,2,2-trifluoroethyl)-1H-pyrazol-4-yl)cyclopent-2-enecarboxylic acid (0.12 g, 0.33 mmol) and purified by preparative HPLC (70 mg, 52%). LCMS (ES+) 384 (M+H)$^+$; RT 10.0 min (Analytical method 3); $^1$H NMR δ (ppm) (DMSO-$d_6$): 10.06 (1H, s), 8.69 (1H, s), 7.97 (1H, s), 7.84 (1H, s), 7.21-7.09 (2H, m), 7.04 (1H, t, J=8.9 Hz), 6.16 (1H, s), 5.13 (2H, q, J=9.1 Hz), 3.20 (1H, ddd, J=13.2, 8.7, 4.4 Hz), 2.76-2.65 (1H, m), 2.62-2.53 (1H, m), 2.12 (3H, d, J=2.5 Hz), 1.83-1.75 (1H, m).

Example 29: (S)-3-(benzo[d]isothiazol-7-yl)-1-(3-fluoro-2-methylphenyl)-N-hydroxycyclopent-2-enecarboxamide

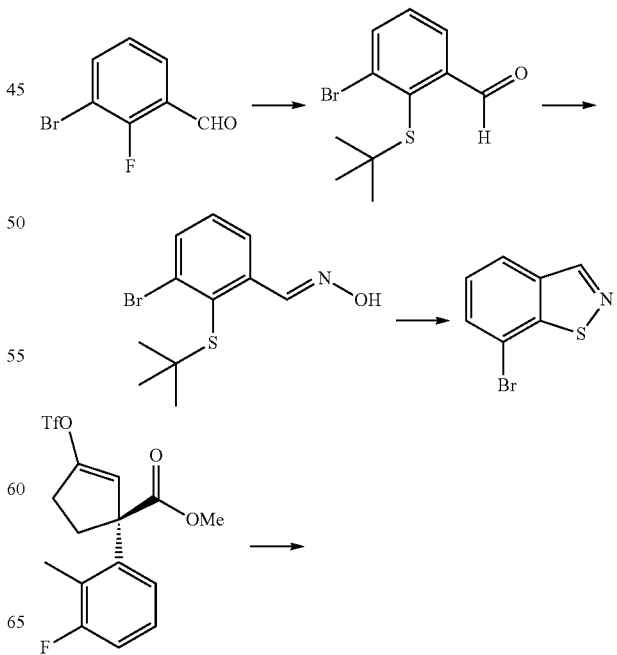

81

-continued

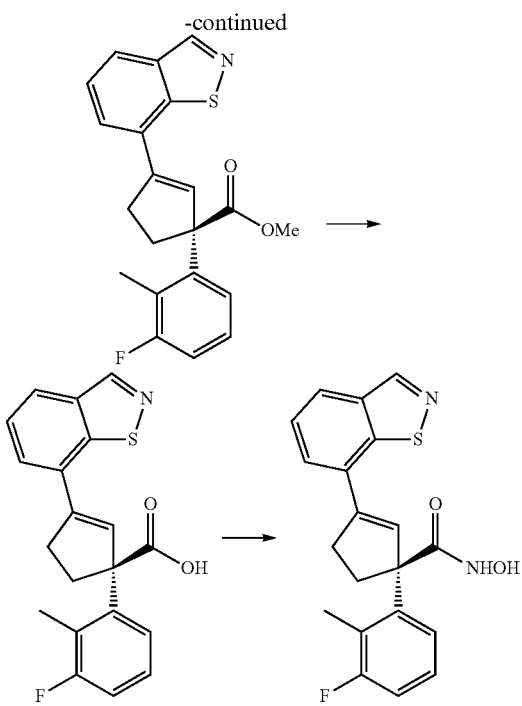

Step 1: 3-bromo-2-(tert-butylthio)benzaldehyde

A 25 mL screw cap tube was charged with 3-bromo-2-fluorobenzaldehyde (4.0 g, 19.7 mmol), potassium carbonate (5.44 g, 39.4 mmol), 2-methyl-2-propanethiol (2.13 g, 2.70 mL, 23.6 mmol) and anhydrous DMF (15 mL). The tube was capped and the reaction mixture heated at 80° C. for 18 h. After this time only 50% of starting material was consumed, so the reaction was heated at 110° C. for a further 24 h. Once completed, the reaction mixture was cooled to r.t. and solids were dissolved in water (15 mL). Solution was then partitioned between Et$_2$O (75 mL) and further water (125 mL). Combined organics were washed with brine (120 mL), then dried and filtered (phase separator) to give a yellow oil. The crude product was purified by flash silica column chromatography (gradient elution iso-hexane to 20% EtOAc in iso-hexane) to give the title compound as a pale yellow semi-solid (4.70 g, 88%). MS (ES+) consistent with target (M+H)$^+$.

Step 2: (E)-3-bromo-2-(tert-butylthio)benzaldehyde Oxime

A 250 mL round-bottom flask was charged with 3-bromo-2-(tert-butylthio)benzaldehyde (4.75 g, 18.2 mmol). To this was added a pre-mixed solution of hydroxylamine hydrochloride (5.70 g, 82.0 mmol) in iso-propanol/water (130 mL/25 mL). The reaction was then heated at 70° C. for 6 h. After this time mixture was cooled to r.t. and volatiles removed under reduced pressure. To the resulting residue was added water (50 mL) followed by sat. aq. NaHCO$_3$ solution (40 mL)—the pH became 8.5. Aqueous layers were then extracted with EtOAc (2×100 mL). Combined organics were washed with water (100 mL) then brine (150 mL), then dried, filtered and concentrated under reduced pressure to give a yellow oil. Trituration from iso-hexane/Et$_2$O gave a colorless solid which was filtered and air dried to give the title compound (3.70 g, 71%). MS (ES+) consistent with target (M+H)$^+$.

82

Step 3: 7-bromobenzo[d]isothiazole

A 100 mL round-bottom flask was charged with (E)-3-bromo-2-(tert-butylthio)benzaldehyde oxime (3.50 g, 12.1 mmol), pTSA.H$_2$O (0.46 g, 2.42 mmol) and anhydrous 1-butanol (40 mL). Reaction mixture was then refluxed for 36 h. After this time volatiles were removed under reduced pressure and the resulting residue partitioned between EtOAc (120 mL) and sat. aq. NaHCO$_3$ solution (50 mL). Organic layers were extracted, washed with brine (50 mL) then dried, filtered and concentrated under reduced pressure to give a pale brown residue. The crude product was purified by flash silica column chromatography (gradient elution iso-hexane to 20% EtOAc in iso-hexane) to give the title compound as a colorless solid (2.41 g, 93%). MS (ES+) consistent with target (M+H)$^+$.

Step 4: (S)-methyl 3-(benzo[d]isothiazol-7-yl)-1-(3-fluoro-2-methylphenyl)cyclopent-2-enecarboxylate Following Method B (iii) from methyl-1-(3-fluoro-2-methylphenyl)-3-(((trifluoromethyl)sulfonyl) oxy)cyclopent-2-enecarboxylate (0.2 g, 0.52 mmol) and 7-bromobenzo[d]isothiazole (0.1 g, 0.52 mmol). Reaction mixture was cooled to r.t. and filtered through silica, washing with CH$_2$Cl$_2$ (3×10 mL). Combined organics were then concentrated to give an orange residue. The crude product was purified by flash silica column chromatography (gradient elution iso-hexane to 20% EtOAc in iso-hexane) to give the title compound as a pale yellow oil (0.15 g, 79%). MS (ES+) consistent with target (M+H)$^+$.

Step 5: (S)-3-(benzo[d]isothiazol-7-yl)-1-(3-fluoro-2-methylphenyl)cyclopent-2-enecarboxylic Acid Following Method C (ii) from (S)-methyl 3-(benzo[d]isothiazol-7-yl)-1-(3-fluoro-2-methylphenyl) cyclopent-2-enecarboxylate (0.15 g, 0.4 mmol) as far as removal of methanol under reduced pressure. Aqueous residues were partitioned between CH$_2$Cl$_2$ (15 mL) and water (15 mL). Organic layers were discarded and basic aqueous layers acidified to pH 3 using 1 M HCl. Acidic aqueous layers were then partitioned with EtOAc (20 mL). Organic layers were extracted, washed with brine (20 mL), dried by filtering through a hydrophobic frit and concentrated to give a colorless oil (0.12 g, 89%). MS (ES+) consistent with target (M+H)$^+$.

Step 6: (S)-3-(benzo[d]isothiazol-7-yl)-1-(3-fluoro-2-methylphenyl)-N-hydroxycyclopent-2-enecarboxamide Following Method D from (S)-3-(benzo[d]isothiazol-7-yl)-1-(3-fluoro-2-methylphenyl)cyclopent-2-enecarboxylic acid (0.12 g, 0.34 mmol) and purified by preparative HPLC (40 mg, 47%). LCMS (ES+) 369 (M+H)$^+$; RT 10.8 min (Analytical method 1); $^1$H NMR δ (ppm) (DMSO-d$_6$): 10.30 (1H, s), 9.27 (1H, s), 8.79 (1H, d, J=1.5 Hz), 8.25 (1H, d, J=7.9 Hz), 7.70 (1H, d, J=7.2 Hz), 7.62 (1H, t, J=7.6 Hz), 7.26-7.22 (1H, m), 7.12-7.05 (1H, m), 6.58 (1H, s), 3.43-3.33 (1H, m), 3.19-3.08 (1H, m), 2.94-2.83 (1H, m), 2.68 (1H, d, J=4.4 Hz), 2.17 (3H, d, J=2.5 Hz), 1.92-1.84 (1H, m).

Example 30: N-hydroxy-1-phenyl-cyclopent-3-enecarboxamide

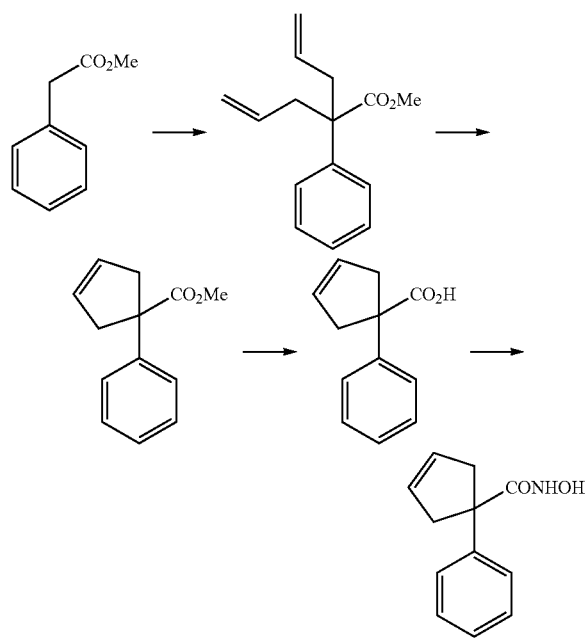

Step 1: methyl 2-allyl-2-phenylpent-4-enoate

Methyl phenyl acetate (2 mL, 13.9 mmol), allyl bromide (2.42 mL, 28 mmol), DMF (20 mL) and NaH (60% dispersion in oil, 1.12 g, 28 mmol) were combined under nitrogen at room temperature and stirred for 18 h. The reaction mixture was then diluted with EtOAc (50 mL), washed with water (3×20 mL) and evaporated to dryness onto silica. Purification by flash chromatography gave a clear oil (2.92 g).

Step 2: methyl 1-phenylcyclopent-3-enecarboxylate

The clear oil from step 1 (1.49 g, 6.48 mmol), dichloromethane (300 mL) and Grubbs $2^{nd}$ generation catalyst (50 mg) were combined and stirred for 12 days. The reaction mixture was then evaporated to dryness onto silica and purified by flash chromatography to give a clear oil (1.34 g).

Step 3: 1-phenylcyclopent-3-enecarboxylic Acid

The clear oil from step 2 (425 mg, 2.1 mmol), MeOH (5 mL) and 15% aq. NaOH (1 mL) were combined in a sealed tube and heated to 120° C. for 36 h. Reaction mixture was then partitioned between EtOAc (20 mL) and 1 N aq. HCl (20 mL). Organic layer was dried (MgSO₄) and evaporated to dryness onto silica. Purification by flash chromatography gave an off-white solid (235 mg).

Step 4: N-hydroxy-1-phenyl-cyclopent-3-enecarboxamide

The off-white solid from step 3 (235 mg, 1.25 mmol), dichloromethane (10 mL) and oxalyl chloride (0.21 mL, 2.5 mmol) were combined and stirred at room temperature under nitrogen for 18 h. Reaction mixture was evaporated to dryness. Dichloromethane (10 mL) and 50% aq. hydroxylamine (1.5 mL) were added and the mixture stirred at room temperature for 2 h. Reaction mixture was then evaporated to dryness and purified by preparative HPLC to give the title compound as a white solid (160 mg); LCMS (ES+) 204 (M+H)⁺, RT 2.97 min (Analytical method 1); ¹H NMR δ (ppm) (DMSO-d₆): 10.49 (1H, s), 8.68 (1H, s), 7.31-7.20 (5H, m), 5.74 (2H, s), 3.26-3.22 (2H, m), 2.61-2.57 (2H, m).

Example 31: 1-(2-fluorophenyl)-N-hydroxy-cyclopent-3-enecarboxamide

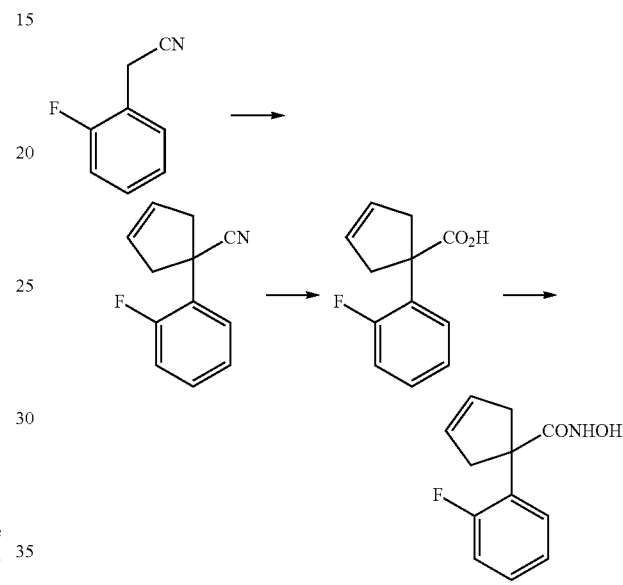

Step 1: 1-(2-fluorophenyl)cyclopent-3-enecarbonitrile 1-(2-Fluorophenyl)acetonitrile (803 mg, 5.95 mmol), cis-1,4-dichloro-2-butene (0.63 mL, 5.95 mmol), DMF (20 mL) and NaH (60% dispersion in oil, 595 mg, 14.87 mmol) were combined under nitrogen at room temperature and stirred for 3 days. The reaction mixture was then diluted with EtOAc (50 mL), washed with water (4×25 mL) and evaporated to dryness onto silica. Purification by flash chromatography gave a colorless solid (746 mg).

Step 2: 1-(2-fluorophenyl)cyclopent-3-enecarboxylic Acid

The colorless solid from step 1 (706 mg) was combined with KOH (500 mg), water (2 mL) and MeOH (10 mL). Reaction mixture was heated to 90° C. for 10 days then partitioned between 1 N aq. HCl (20 mL) and EtOAc (50 mL). Organic layer was evaporated to dryness onto silica and purified by flash chromatography to give a white solid (313 mg).

Step 3: 1-(2-fluorophenyl)-N-hydroxy-cyclopent-3-enecarboxamide

The white solid from step 2 (204 mg), DCM (10 mL) and oxalyl chloride (0.17 mL, 2 mmol) were combined and stirred at room temperature under nitrogen for 18 h. Reaction mixture was evaporated to dryness. DCM (20 mL) and 50% aq. hydroxylamine (2 mL) were added and the mixture stirred at room temperature for 2 h. The reaction mixture was then evaporated to dryness and purified by preparative HPLC to give the title compound as an off white solid (38 mg). LCMS (ES+) 222 (M+H)+, RT 7.94 min (Analytical method 2); $^1$H NMR δ (ppm) (DMSO-$d_6$): 10.20 (1H, s), 8.65 (1H, s), 7.33-7.27 (2H, m), 7.16-7.10 (2H, m), 5.69 (2H, s), 3.21-3.17 (2H, m), 2.65-2.61 (2H, m).

Example 32: (S)-3-cyclopropyl-1-(3-fluoro-2-methylphenyl)-N-hydroxycyclopent-2-enecarboxamide

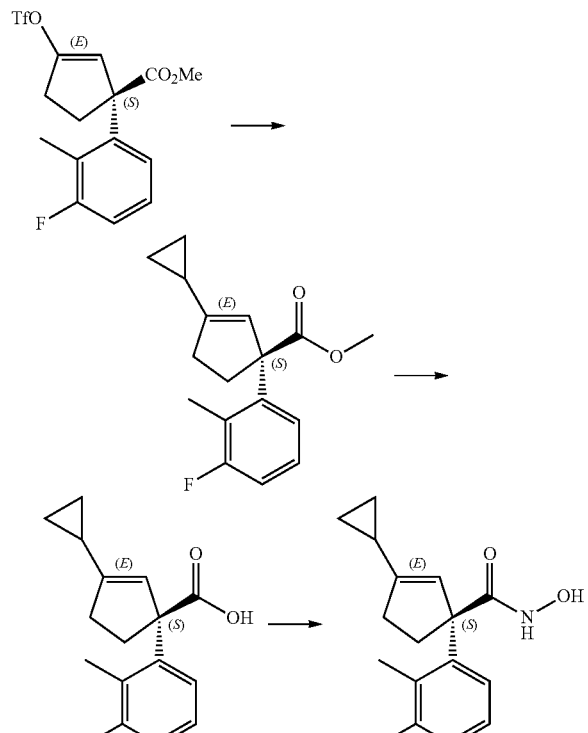

Step 1: (S)-methyl-3-cyclopropyl-1-(3-fluoro-2-methylphenyl)cyclopent-2-enecarboxylate Following Method B from (S)-methyl 1-(3-fluoro-2-methylphenyl)-3-(((trifluoromethyl)sulfonyl)oxy)cyclopent-2-enecarboxylate (100 mg, 0.26 mmol) and cyclopropylboronic acid utilizing $Cs_2CO_3$, dioxane, water and palladium tetrakis(triphenylphosphine) at 100° C. The crude product was purified by flash column chromatography to give the title compound as a clear gum (65 mg).

Step 2: (S)-3-cyclopropyl-1-(3-fluoro-2-methylphenyl)cyclopent-2-enecarboxylic Acid Following Method C from (S)-methyl-3-cyclopropyl-1-(3-fluoro-2-methylphenyl)cyclopent-2-enecarboxylate (65 mg, 0.24 mmol) to give the title compound as a cream solid (50 mg).

Step 3: (S)-3-cyclopropyl-1-(3-fluoro-2-methylphenyl)-N-hydroxycyclopent-2-enecarboxamide Following Method D from (S)-3-cyclopropyl-1-(3-fluoro-2-methylphenyl)cyclopent-2-enecarboxylic acid (50 mg, 0.19 mmol) and purified by preparative HPLC to give the title compound as a white solid (10 mg, 20%). LCMS (ES+) 276 (M+H)+, RT 3.64 min (Analytical method 1); $^1$H NMR δ (ppm) (DMSO-$d_6$): 9.91 (1H, s), 8.62 (1H, s), 7.18-7.12 (1H, m), 7.08-6.96 (2H, m), 5.65 (1H, s), 3.15-3.08 (1H, m), 2.51-2.43 (1H, m), 2.18-2.11 (1H, m), 2.17 (3H, d, J=2.4 Hz), 1.78-1.61 (2H, m), 0.77-0.70 (2H, m), 0.61-0.54 (2H, m).

Example 33: (S)-N-hydroxy-1,3-diphenylcyclopent-2-enecarboxamide

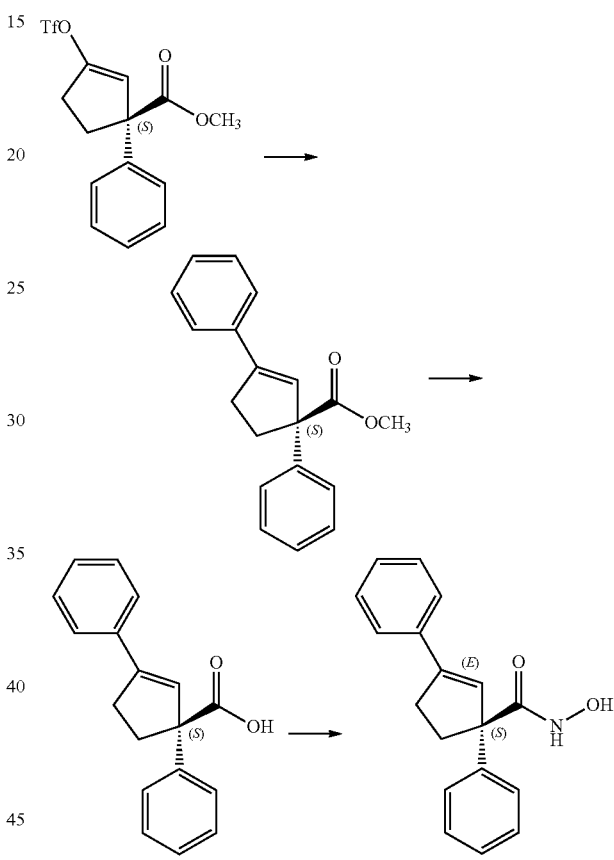

Step 1: (S)-methyl 1,3-diphenylcyclopent-2-enecarboxylate

Following Method B from Intermediate 4 (190 mg, 0.54 mmol) and phenylboronic acid (65 mg) utilizing $Cs_2CO_3$ (352 mg) in place of $K_2CO_3$. The crude product was purified by flash column chromatography (gradient elution, 0-5% EtOAc in iso-hexane) to give the title compound as a crystalline solid (115 mg).

Step 2: (S)-1,3-diphenylcyclopent-2-enecarboxylic Acid

Following Method C from (S)-methyl 1,3-diphenylcyclopent-2-enecarboxylate (115 mg, 0.41 mmol), utilizing KOH in place of NaOH and heating for 2 h to give the title compound as a white solid (100 mg).

Step 3: (S)-N-hydroxy-1,3-diphenylcyclopent-2-enecarboxamide

Following Method D from (S)-1,3-diphenylcyclopent-2-enecarboxylic acid (100 mg, 0.38 mmol), running the reaction at r.t. Purification by silica column chromatography (gradient elution, 0-50% EtOAc in iso-hexane) gave the title compound as a white solid (20 mg, 49%). LCMS (ES+) 280 (M+H)$^+$, RT 3.66 min (Analytical method 1); $^1$H NMR δ (ppm) (DMSO-d$_6$): 10.35 (1H, d, J=1.7 Hz), 8.71 (1H, d, J=1.6 Hz), 7.49-7.44 (2H, m), 7.34-7.19 (7H, m), 7.17-7.12 (1H, m), 6.67 (1H, s), 2.92 (1H, dt, J=13.0, 6.4 Hz), 2.66-2.60 (2H, m), 2.03 (1H, dt, J=13.0, 7.5 Hz).

Example 34: (R)-N-hydroxy-1,3-diphenylcyclopent-2-enecarboxamide

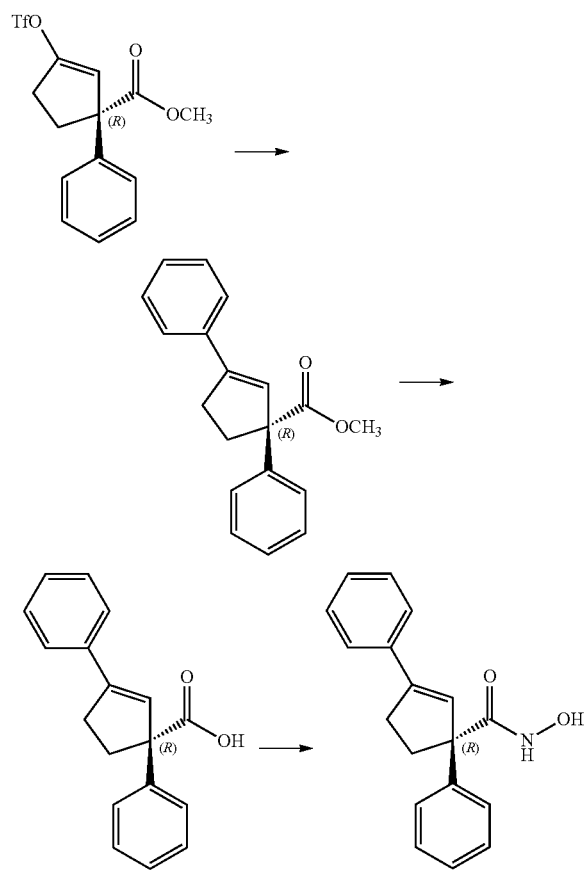

Step 1: (R)-methyl 1,3-diphenylcyclopent-2-enecarboxylate

Following Method B from Intermediate 4 (110 mg, 0.31 mmol) and phenylboronic acid (42 mg) utilizing Cs$_2$CO$_3$ (195 mg) in place of K$_2$CO$_3$. The crude product was purified by flash column chromatography (gradient elution, 0-50% EtOAc in iso-hexane) to give the title compound as a crystalline solid (50 mg).

Step 2: (R)-1,3-diphenylcyclopent-2-enecarboxylic Acid

Following Method C (ii) from (R)-methyl 1,3-diphenylcyclopent-2-enecarboxylate (50 mg, 0.18 mmol), running the reaction at r.t. for 16 h. The title compound was obtained as a white solid (48 mg).

Step 3: (R)-N-hydroxy-1,3-diphenylcyclopent-2-enecarboxamide

Following Method D from (R)-1,3-diphenylcyclopent-2-enecarboxylic acid (45 mg, 0.17 mmol). The title compound was obtained as a white solid (37 mg, 78%). LCMS (ES+) 280 (M+H)$^+$, RT 3.67 min (Analytical method 1); $^1$H NMR δ (ppm) (DMSO-d$_6$): 10.35 (1H, d, J=1.7 Hz), 8.71 (1H, d, J=1.6 Hz), 7.49-7.44 (2H, m), 7.34-7.19 (7H, m), 7.17-7.12 (1H, m), 6.67 (1H, s), 2.92 (1H, dt, J=13.0, 6.4 Hz), 2.66-2.60 (2H, m), 2.03 (1H, dt, J=13.0, 7.5 Hz).

Example 35: (S)-3-(5-fluoropyridin-3-yl)-N-hydroxy-1-phenylcyclopent-2-enecarboxamide

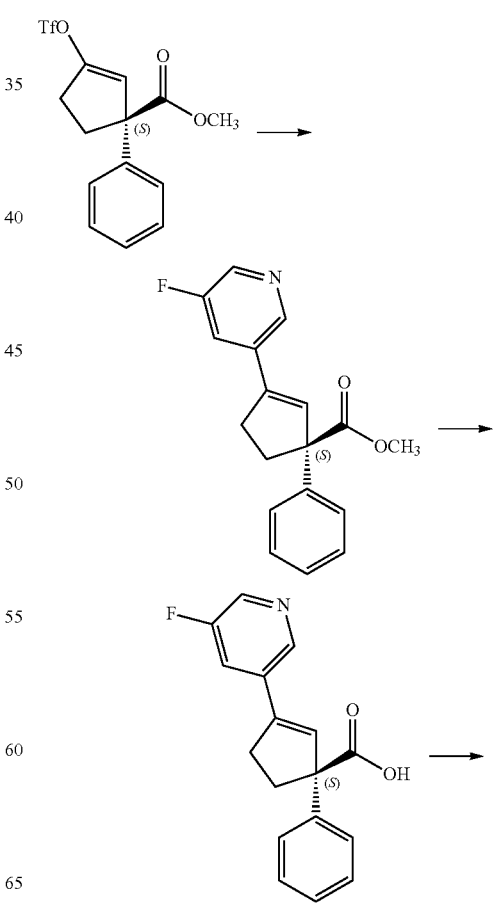

-continued

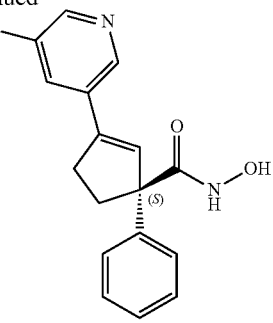

Step 1: (S)-methyl 3-(5-fluoropyridin-3-yl)-1-phenylcyclopent-2-enecarboxylate

Following Method B from Intermediate 4 (400 mg, 1.14 mmol) and (5-fluoropyridin-3-yl)boronic acid (160 mg) utilizing $Cs_2CO_3$ (743 mg) in place of $K_2CO_3$. The crude product was purified by flash column chromatography (gradient elution, 0-50% EtOAc in iso-hexane) to give the title compound as a crystalline solid (300 mg).

Step 2: (S)-3-(5-fluoropyridin-3-yl)-1-phenylcyclopent-2-enecarboxylic Acid

Following Method C from (S)-methyl 3-(5-fluoropyridin-3-yl)-1-phenylcyclopent-2-enecarboxylate (300 mg, 1.01 mmol), utilizing KOH in place of NaOH and heating for 2 h to give the title compound as a white solid (276 mg).

Step 3: (S)-3-(5-fluoropyridin-3-yl)-N-hydroxy-1-phenylcyclopent-2-enecarboxamide Following Method D from (S)-3-(5-fluoropyridin-3-yl)-1-phenylcyclopent-2-enecarboxylic acid (276 mg, 0.98 mmol). The title compound was obtained as a white solid (52 mg, 18%). LCMS (ES+) 299 (M+H)$^+$, RT 3.20 min(Analytical method 1); $^1$H NMR δ (ppm) (DMSO-d$_6$): 10.47 (1H, s), 8.87 (1H, s), 8.69 (1H, t, J=1.6 Hz), 8.54 (1H, d, J=2.8 Hz), 7.93-7.88 (1H, m), 7.43-7.34 (4H, m), 7.30-7.24 (1H, m), 7.00 (1H, s), 3.05-2.97 (1H, m), 2.82-2.76 (2H, m), 2.24-2.16 (1H, m).

Example 36: (S)-3-(5-chloro-2-methylpyridin-3-yl)-1-(3-fluoro-2-methylphenyl)-N-hydroxycyclopent-2-enecarboxamide Example 37: (S)-1-(3-fluoro-2-methylphenyl)-N-hydroxy-3-(2-methylpyridin-3-yl)cyclopent-2-enecarboxamide

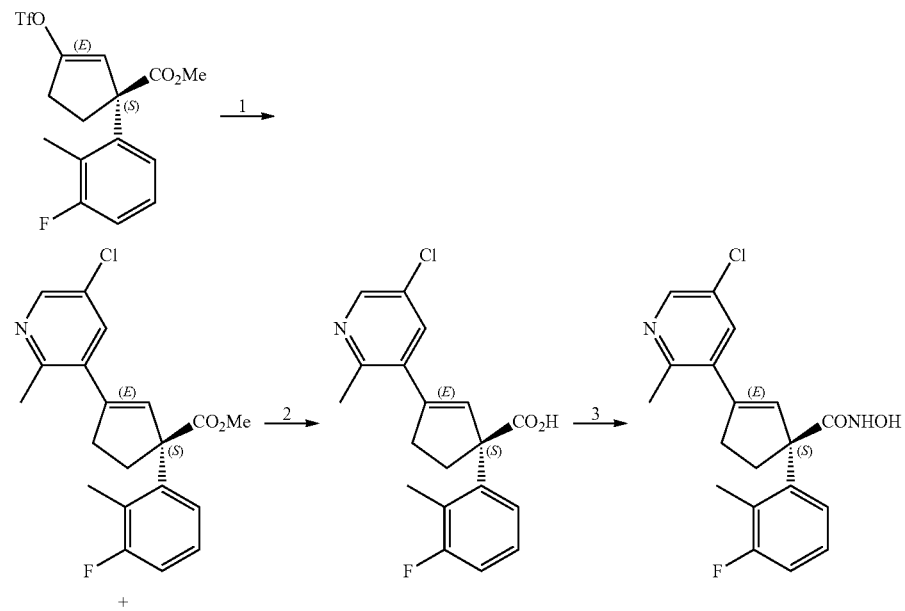

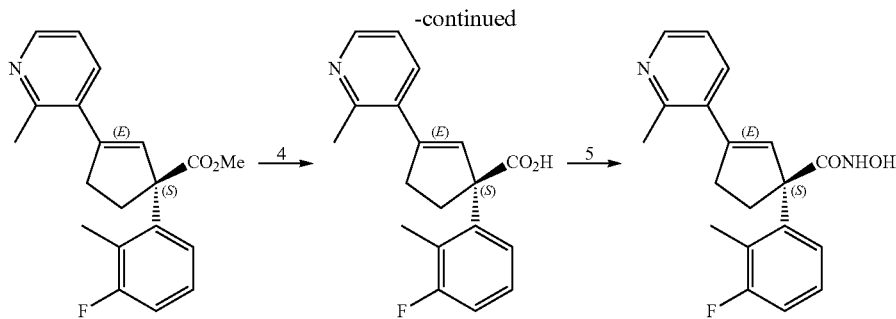

Step 1: (S)-methyl 3-(5-chloro-2-methylpyridin-3-yl)-1-(3-fluoro-2-methylphenyl)cyclopent-2-enecarboxylate and (S)-methyl 1-(3-fluoro-2-methylphenyl)-3-(2-methylpyridin-3-yl)cyclopent-2-enecarboxylate (S)-Methyl 1-(3-fluoro-2-methylphenyl)-3-(((trifluoromethyl)sulfonyl)oxy)cyclopent-2-enecarboxylate (400 mg, 1.05 mmol), 5-chloro-2-methylpyridine-3-boronic acid (179 mg, 1.05 mmol), CsF (200 mg), DME (15 mL), MeOH (2 mL) and palladium tetrakis(triphenylphosphine) (10 mg) were combined in a sealed tube and heated by microwave to 120° C. for 2 h. The reaction mixture was then evaporated to dryness onto silica and purified by flash chromatography to give: (S)-Methyl 3-(5-chloro-2-methylpyridin-3-yl)-1-(3-fluoro-2-methylphenyl)cyclopent-2-enecarboxylate (266 mg) as a clear gum.

(S)-Methyl 1-(3-fluoro-2-methylphenyl)-3-(2-methylpyridin-3-yl)cyclopent-2-enecarboxylate (75 mg) as a clear gum.

Step 2: (S)-3-(5-chloro-2-methylpyridin-3-yl)-1-(3-fluoro-2-methylphenyl)cyclopent-2-enecarboxylic Acid (S)-Methyl 3-(5-chloro-2-methylpyridin-3-yl)-1-(3-fluoro-2-methylphenyl)cyclopent-2-enecarboxylate (265 mg, 0.737 mmol), MeOH (10 mL) and 15% aq. NaOH solution (2 mL) were combined in a sealed tube and heated to 65° C. for 2 days. The reaction mixture was evaporated in vacuo then partitioned between EtOAc and $H_2O$/AcOH. The organic layer was dried ($MgSO_4$) and evaporated in vacuo to give the title compound as an off white solid (200 mg, 79%).

Step 3: (S)-3-(5-chloro-2-methylpyridin-3-yl)-1-(3-fluoro-2-methylphenyl)-N-hydroxycyclopent-2-enecarboxamide (S)-3-(5-chloro-2-methylpyridin-3-yl)-1-(3-fluoro-2-methylphenyl)cyclopent-2-enecarboxylic acid (200 mg, 0.58 mmol), TFFH (214 mg, 0.81 mmol), DMF (2 mL) and $Et_3N$ (0.28 mL, 2 mmol) were combined and stirred at room temperature under a nitrogen atmosphere. After 18 hours O-(tetrahydro-2H-pyran-2-yl)hydroxylamine (117 mg, 1 mmol) was added and the mixture stirred for 3 days. MeOH (2 mL) and 2 N HCl in diethyl ether (2 mL) were added and the mixture stirred for 5 hours. Volatile solvents were removed in vacuo and the crude material was purified by preparative HPLC to give the title compound as a tan solid (139 mg). LCMS (ES+) 361/363 (M+H)$^+$, RT 3.71 min (Analytical method 1); $^1$H NMR δ (ppm) (DMSO-$d_6$): 10.16 (1H, s), 8.76 (1H, br s), 8.19 (1H, dd, J=2.4, 0.8 Hz), 7.74 (1H, d, J=1.6 Hz), 7.25-7.15 (2H, m), 7.10-7.05 (1H, m), 6.53 (1H, s), 3.40-3.25 (1H, m), 3.05-2.95 (1H, m), 2.75-2.65 (1H, m), 2.33 (3H, s), 2.14 (3H, d, J=2.4 Hz), 1.85-1.75 (1H, m).

Step 4: (S)-1-(3-fluoro-2-methylphenyl)-3-(2-methylpyridin-3-yl)cyclopent-2-enecarboxylic Acid (S)-Methyl 1-(3-fluoro-2-methylphenyl)-3-(2-methylpyridin-3-yl)cyclopent-2-enecarboxylate (75 mg), MeOH (10 mL) and 15% aq. NaOH solution (2 mL) were combined in a sealed tube and heated to 65° C. for 1 day. The reaction mixture was evaporated in vacuo then partitioned between EtOAc and $H_2O$/AcOH. Organic layer was dried ($MgSO_4$) and evaporated in vacuo to give the title compound as an off white solid (70 mg).

Step 5: (S)-1-(3-fluoro-2-methylphenyl)-N-hydroxy-3-(2-methylpyridin-3-yl)cyclopent-2-enecarboxamide (S)-1-(3-fluoro-2-methylphenyl)-3-(2-methylpyridin-3-yl)cyclopent-2-enecarboxylic acid (70 mg, 0.23 mmol), TFFH (130 mg, 0.5 mmol), DMF (1 mL) and $Et_3N$ (0.21 mL, 1.5 mmol) were combined and stirred at room temperature under a nitrogen atmosphere. After 30 minutes O-(tetrahydro-2H-pyran-2-yl)hydroxylamine (100 mg, 0.85 mmol) was added and the mixture stirred for 1 day. MeOH (2 mL) and 2 N HCl in diethyl ether (2 mL) were added and the mixture stirred for 1 h. Volatile solvents were removed in vacuo and the crude material was purified by preparative HPLC to give the title compound as a pale yellow solid (37 mg). LCMS (ES+) 327 (M+H)$^+$, RT 2.47 min (Analytical method 1); $^1$H NMR δ (ppm) (DMSO-$d_6$): 10.14 (1H, s), 8.77 (1H, br s), 8.57 (1H, d, J=1.6 Hz), 8.35 (1H, d, J=1.2 Hz), 7.79 (1H, s), 7.25-7.00 (3H, m), 6.61 (1H, s), 3.40-3.25 (1H, m), 2.95-2.85 (1H, m), 2.80-2.65 (1H, m), 2.34 (3H, s), 2.14 (3H, d, J=2.4 Hz), 1.95-1.85 (1H, m).

Example 38: (S)-1-(3-fluoro-2-methylphenyl)-N-hydroxy-3-(1-methyl-1H-indazol-6-yl)cyclopent-2-enecarboxamide

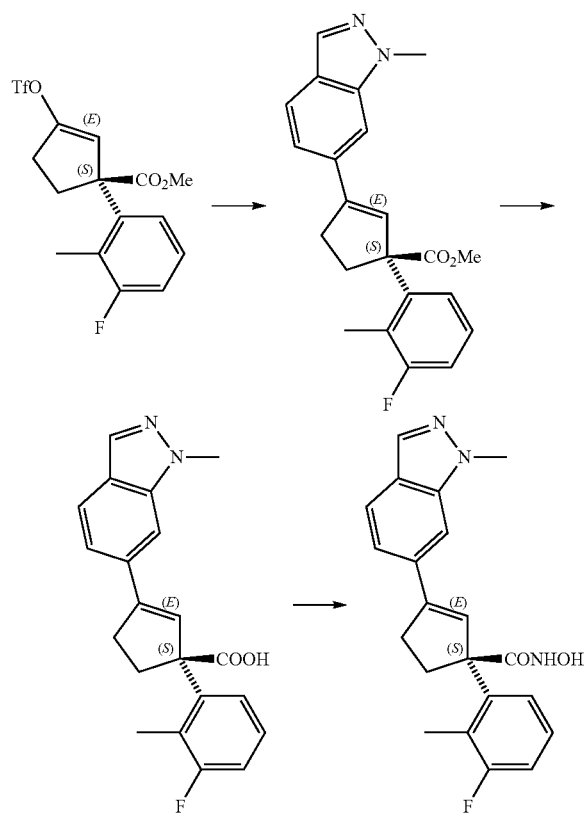

Step 1: (S)-methyl 1-(3-fluoro-2-methylphenyl)-3-(1-methyl-1H-indazol-6-yl)cyclopent-2-enecarboxylate (S)-Methyl 1-(3-fluoro-2-methylphenyl)-3-(((trifluoromethyl)sulfonyl)oxy)cyclopent-2-enecarboxylate (300 mg, 0.79 mmol), (1-methyl-1H-indazol-6-yl)boronic acid (139 mg, 0.79 mmol), CsF (200 mg), DME (15 mL), MeOH (3 mL) and palladium tetrakis(triphenylphosphine) (20 mg) were combined in a sealed tube and heated by microwave to 120° C. for 2 h. The reaction mixture was then evaporated to dryness onto silica and purified by flash chromatography (gradient elution, 0-100% EtOAc in iso-hexane) to give the title compound as a colorless gum (176 mg).

Step 2: (S)-1-(3-fluoro-2-methylphenyl)-3-(1-methyl-1H-indazol-6-yl)cyclopent-2-enecarboxylic Acid Following Method C from (S)-methyl 1-(3-fluoro-2-methylphenyl)-3-(1-methyl-1H-indazol-6-yl)cyclopent-2-enecarboxylate (170 mg). The title compound was obtained as a tan solid (150 mg).

Step 3: (S)-1-(3-fluoro-2-methylphenyl)-N-hydroxy-3-(1-methyl-1H-indazol-6-yl)cyclopent-2-enecarboxamide Following Method D from (S)-1-(3-fluoro-2-methylphenyl)-3-(1-methyl-1H-indazol-6-yl)cyclopent-2-enecarboxylic acid (150 mg). The compound was obtained as a colorless solid (59 mg, 38%). LCMS (ES+) 366 (M+H)+, RT 10.2 min (Analytical method 3); $^1$H NMR δ (ppm) (DMSO-$d_6$): 10.17 (1H, s), 8.78 (1H, d, J=1.1 Hz), 8.06 (1H, d, J=0.8 Hz), 7.78 (1H, dd, J=8.6, 0.5 Hz), 7.72 (1H, s), 7.48 (1H, dd, J=8.5, 1.1 Hz), 7.24-7.20 (2H, m), 7.13-7.07 (1H, m), 6.64 (1H, s), 4.11 (3H, s), 3.34-3.30 (1H, m), 3.06-2.97 (1H, m), 2.90-2.82 (1H, m), 2.19 (3H, d, J=2.4 Hz), 1.96-1.88 (1H, m).

Example 39: (S)-3-(1-(difluoromethyl)-1H-indazol-6-yl)-1-(3-fluoro-2-methylphenyl)-N-hydroxycyclopent-2-enecarboxamide

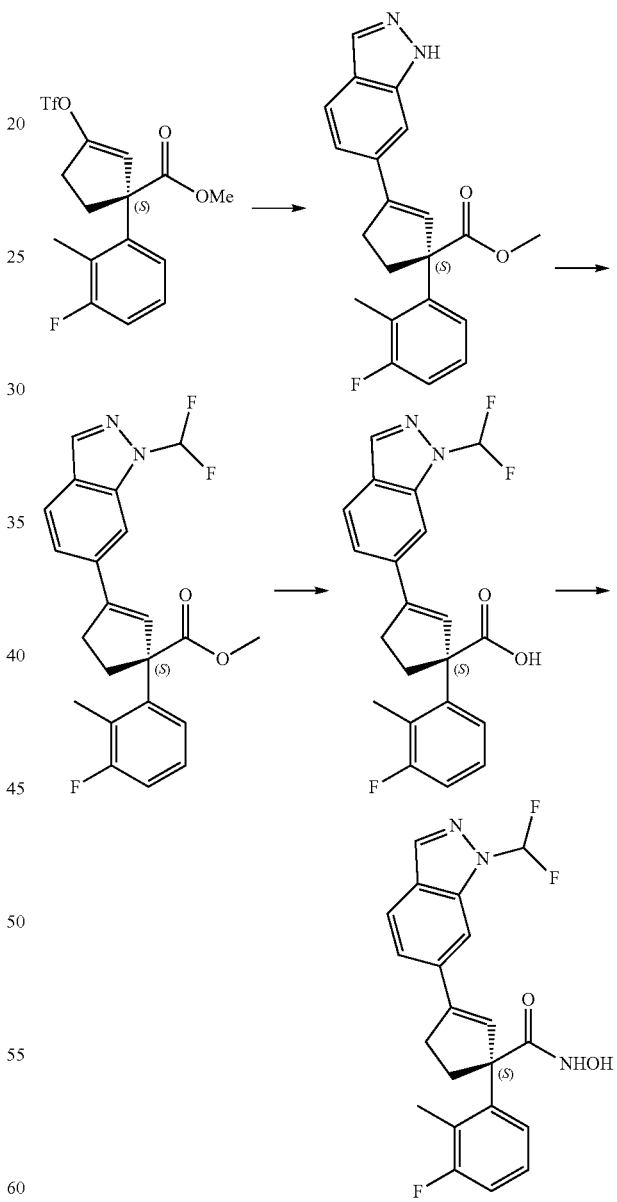

Step 1: (S)-methyl 1-(3-fluoro-2-methylphenyl)-3-(1H-indazol-6-yl)cyclopent-2-enecarboxylate Following Method B from (S)-methyl 1-(3-fluoro-2-methylphenyl)-3-((((trifluoromethyl)sulfonyl) oxy)cyclopent-2-enecarboxylate (0.30 g, 0.79 mmol) and 6-(4,4,5,5-tetramethyl-1,3,2-dioxaborolan-2-yl)-1H-indazole (0.26 g, 0.16 mmol). The crude product was purified by silica column chromatography (gradient elution, 0-25% EtOAc in iso-hexane) to give the title compound as a colorless solid (0.15 g, 56%).

Step 2: (S)-methyl 3-(1-(difluoromethyl)-1H-indazol-6-yl)-1-(3-fluoro-2-methylphenyl)cyclopent-2-enecarboxylate A 25 mL round bottom flask was charged with (S)-methyl 1-(3-fluoro-2-methylphenyl)-3-(1H-indazol-6-yl)cyclopent-2-enecarboxylate (0.14 g, 0.48 mmol), 18-crown-6 (0.02 g, 0.09 mmol) and anhydrous acetonitrile (10 mL). The reagents were stirred until a colorless solution formed then sodium chlorodifluoroacetate (0.08 g, 0.48 mmol) was added and the reaction mixture refluxed for 18 h. After this time a further portion of 18-crown-6 (0.02 g, 0.09 mmol) and sodium chlorodifluoroacetate (0.08 g, 0.48 mmol) were added and the reaction mixture was refluxed for a further 20 h. After this time the reaction was cooled to r.t. and precipitated solid filtered through Celite, washing with EtOAc (3×20 mL). The combined organics were then dried and filtered (phase separator) to give a yellow residue. The crude product was purified by silica column chromatography (gradient elution, 0-20% EtOAc in iso-hexane) to give the title compound as a colorless oil (0.07 g, 28%).

Step 3: (S)-3-(1-(difluoromethyl)-1H-indazol-6-yl)-1-(3-fluoro-2-methylphenyl)cyclopent-2-enecarboxylic Acid Following Method C (ii) from (S)-methyl 3-(1-(difluoromethyl)-1H-indazol-6-yl)-1-(3-fluoro-2-methylphenyl) cyclopent-2-enecarboxylate (0.06 g, 0.16 mmol). After removing methanol, the aqueous residues were partitioned between $CH_2Cl_2$ (15 mL) and water (15 mL). Organic layers were discarded and basic aqueous layers acidified to pH 3 using 1 M HCl. Acidic aqueous layers were then partitioned with EtOAc (20 mL); the organic layers were extracted, washed with brine (20 mL), dried, filtered (phase separation cartridge) and concentrated to give the title compound as a colorless solid (0.04 g, 70%).

Step 4: (S)-3-(1-(difluoromethyl)-1H-indazol-6-yl)-1-(3-fluoro-2-methylphenyl)-N-hydroxycyclopent-2-enecarboxamide Following Method D from (S)-3-(1-(difluoromethyl)-1H-indazol-6-yl)-1-(3-fluoro-2-methylphenyl)cyclopent-2-enecarboxylic acid (0.04 g, 0.26 mmol) and purified by preparative HPLC (0.007 g, 18%). LCMS (ES+) 402 (M+H)+; RT 10.5 min (Analytical method 3); $^1$H NMR δ (ppm) (DMSO-$d_6$): 10.19 (1H, s), 8.88 (1H, d, J=0.9 Hz), 8.80 (1H, s), 8.17 (1H, t, J=59.1 Hz), 7.83 (1H, dd, J=9.0, 0.6 Hz), 7.68 (1H, s), 7.59 (1H, dd, J=9.0, 1.2 Hz), 7.24-7.18 (2H, m), 7.13-7.06 (1H, m), 6.68 (1H, s), 3.34-3.29 (1H, m), 3.03-2.95 (1H, m), 2.88-2.81 (1H, m), 2.19 (3H, d, J=2.4 Hz), 1.96-1.88 (1H, m).

Example 40: (S)-3-(benzo[d]thiazol-5-yl)-1-(3-fluoro-2-methylphenyl)-N-hydroxycyclopent-2-enecarboxamide

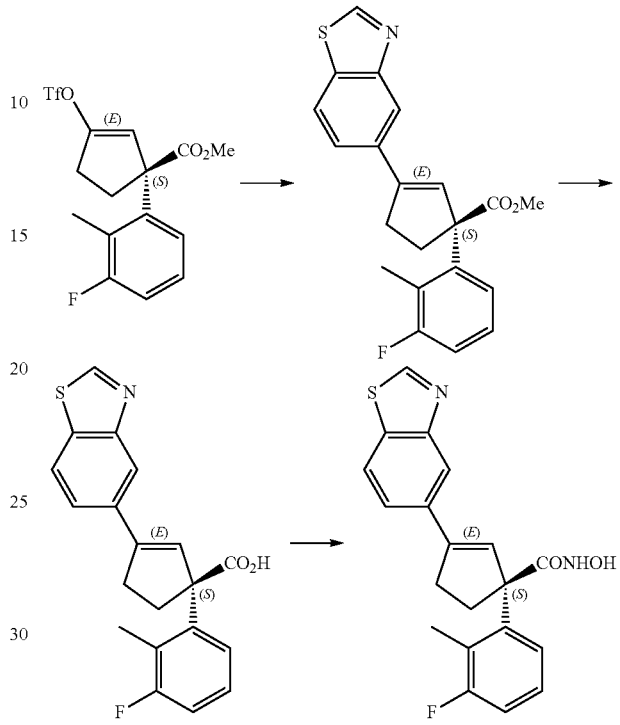

Step 1: (S)-methyl 3-(benzo[d]thiazol-5-yl)-1-(3-fluoro-2-methylphenyl)cyclopent-2-enecarboxylate (S)-Methyl 1-(3-fluoro-2-methylphenyl)-3-(((trifluoromethyl)sulfonyl)oxy)cyclopent-2-enecarboxylate (250 mg, 0.65 mmol), benzthiazole-5-boronic acid (170 mg, 0.65 mmol), CsF (200 mg), DME (15 mL), MeOH (2 mL) and palladium tetrakis(triphenylphosphine) (10 mg) were combined in a sealed tube and heated by microwave to 120° C. for 2 h. The reaction mixture was then evaporated to dryness onto silica and purified by flash chromatography to give the title compound as a clear gum (204 mg, 86%). LCMS (ES+) 368 (M+H)+.

Step 2: (S)-3-(benzo[d]thiazol-5-yl)-1-(3-fluoro-2-methylphenyl)cyclopent-2-enecarboxylic Acid (S)-Methyl 3-(benzo[d]thiazol-5-yl)-1-(3-fluoro-2-methylphenyl)cyclopent-2-enecarboxylate (200 mg), MeOH (10 mL) and 15% aq. NaOH solution (2 mL) were combined in a sealed tube and heated to 65° C. for 4 days. The reaction mixture was evaporated in vacuo then partitioned between EtOAc and $H_2O$/AcOH. Organic layer was dried (MgSO$_4$) and evaporated in vacuo to give the crude title compound as a brown solid (239 mg). LCMS (ES+) 354 (M+H)+.

Step 3: (S)-3-(benzo[d]thiazol-5-yl)-1-(3-fluoro-2-methylphenyl)-N-hydroxycyclopent-2-enecarboxamide (S)-3-(Benzo[d]thiazol-5-yl)-1-(3-fluoro-2-methylphenyl)cyclopent-2-enecarboxylic acid (239 mg), TFFH (201 mg, 0.76 mmol), DMF (3 mL) and Et₃N (0.42 mL, 3 mmol) were combined and stirred at room temperature under a nitrogen atmosphere. After 16 hours O-(tetrahydro-2H-pyran-2-yl)hydroxylamine (117 mg, 1 mmol) was added and the mixture stirred for 3 days. MeOH (2 mL) and 2 N HCl in diethyl ether (2 mL) were both added and the mixture stirred for 4 h. Volatile solvents were removed in vacuo and the remaining crude product was purified by preparative HPLC to give the title compound as a brown solid (16 mg). LCMS (ES+) 369 (M+H)⁺, RT 3.67 min (Analytical method 1); ¹H NMR δ (ppm) (DMSO-d₆): 10.15 (1H, s), 9.42 (1H, s), 8.75 (1H, br s), 8.25-8.15 (2H, m), 7.80-7.70 (1H, m), 7.25-7.15 (2H, m), 7.15-7.00 (1H, m), 6.50 (1H, s), 3.40-3.35 (1H, m), 3.05-2.95 (1H, m), 2.85-2.75 (1H, m), 2.16 (3H, d, J=2.4 Hz), 1.95-1.85 (1H, m).

Example 41: (S)-3-(benzo[b]thiophen-2-yl)-1-(3-fluoro-2-methylphenyl)-N-hydroxycyclopent-2-enecarboxamide

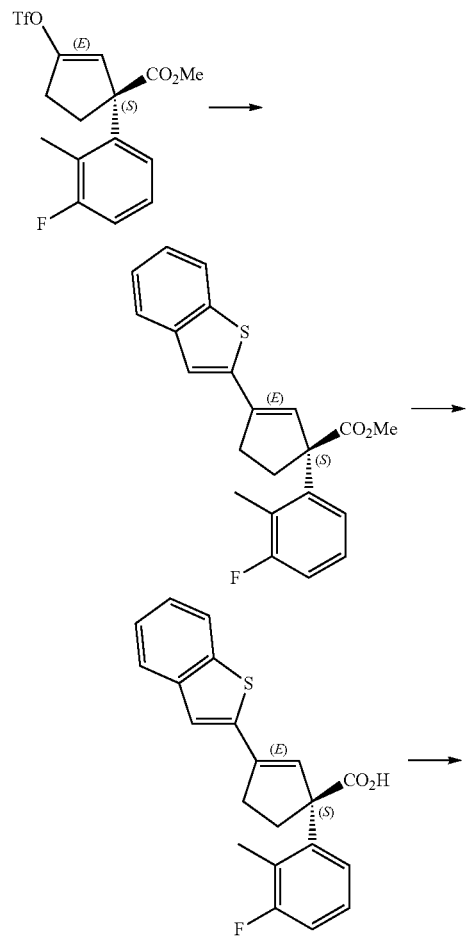

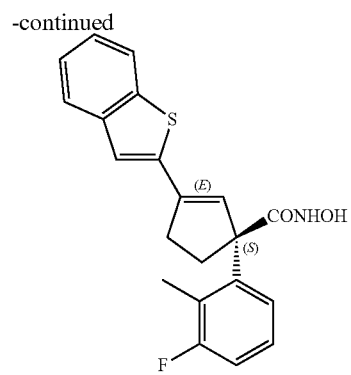

Step 1: (S)-methyl 3-(benzo[b]thiophen-2-yl)-1-(3-fluoro-2-methylphenyl)cyclopent-2-enecarboxylate (S)-Methyl 1-(3-fluoro-2-methylphenyl)-3-(((trifluoromethyl)sulfonyl)oxy)cyclopent-2-enecarboxylate (550 mg, 1.44 mmol), benzothiophene-2-boronic acid (256 mg, 1.44 mmol), CsF (300 mg), DME (15 mL), MeOH (2 mL) and palladium tetrakis(triphenylphosphine) (10 mg) were combined in a sealed tube and heated by microwave to 120° C. for 2 h. The reaction mixture was then evaporated to dryness onto silica and purified by flash chromatography to give the title compound as a white solid (392 mg, 74%).

Step 2: (S)-3-(benzo[b]thiophen-2-yl)-1-(3-fluoro-2-methylphenyl)cyclopent-2-enecarboxylic Acid (S)-Methyl 3-(benzo[b]thiophen-2-yl)-1-(3-fluoro-2-methylphenyl)cyclopent-2-enecarboxylate (390 mg, 1.06 mmol), MeOH (15 mL) and 15% aq. NaOH solution (3 mL) were combined in a sealed tube and heated to 65° C. for 3 days. The reaction mixture was evaporated in vacuo then partitioned between EtOAc and H₂O/AcOH. Organic layer was dried (MgSO₄) and evaporated in vacuo to give the title compound as an off white solid (351 mg, 94%). MS (ES−) consistent with target (M−CO₂H)⁻

Step 3: (S)-3-(benzo[b]thiophen-2-yl)-1-(3-fluoro-2-methylphenyl)-N-hydroxycyclopent-2-enecarboxamide (S)-3-(Benzo[b]thiophen-2-yl)-1-(3-fluoro-2-methylphenyl)cyclopent-2-enecarboxylic acid (350 mg, 0.99 mmol), TFFH (370 mg, 1.4 mmol), DMF (2 mL) and Et₃N (0.42 mL, 3 mmol) were combined and stirred at room temperature under a nitrogen atmosphere. After 16 hours O-(tetrahydro-2H-pyran-2-yl)hydroxylamine (117 mg, 1 mmol) was added and the mixture stirred for 3 days. MeOH (2 mL) and 2 N HCl in diethyl ether (2 mL) were both added and the mixture stirred for 5 h. Volatile solvents were removed in vacuo and the remaining crude product was purified by preparative HPLC to give the title compound as a tan solid (113 mg). LCMS (ES+) 368 (M+H)⁺, RT 4.30 min (Analytical method 1); ¹H NMR δ (ppm) (DMSO-d₆): 10.18 (1H, s), 8.80 (1H, s), 8.00-7.90 (1H, m), 7.85-7.78 (1H, m), 7.44 (1H, s), 7.40-7.30 (2H, m), 7.25-7.15 (1H, m), 7.15-7.00 (2H, m), 6.39 (1H, s), 3.45-3.30 (1H, m), 3.00-2.85 (1H, m), 2.85-2.75 (1H, m), 2.14 (3H, d, J=2.4 Hz), 1.95-1.80 (1H, m).

Example 42: (S)-1-(3,4-difluoro-2-methylphenyl)-N-hydroxy-3-(1-methyl-1H-indazol-6-yl)cyclopent-2-enecarboxamide

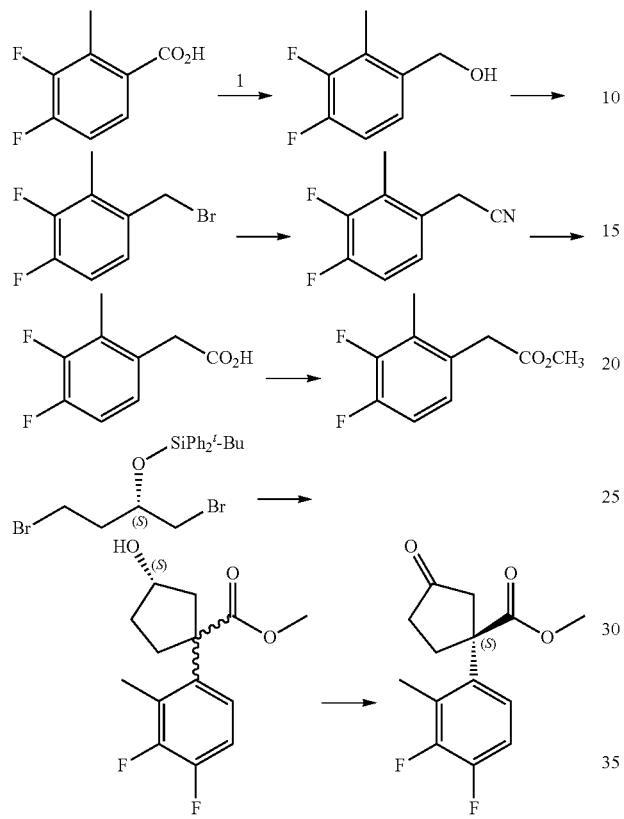

Step 1: (3,4-difluoro-2-methylphenyl)methanol

To a solution of 3,4-difluoro-2-methylbenzoic acid (9.50 g, 55.2 mmol) in anhydrous dichloromethane (200 mL) was added oxalyl chloride (8.57 g, 67.5 mmol, 6 mL) and DMF (0.1 mL, cat.) and the reaction mixture stirred at r.t. for 1 h and then refluxed for a further 1.5 h. After this time the reaction mixture was cooled to r.t. and concentrated under reduced pressure to give the crude acid chloride as a yellow oil. The crude mixture was dissolved in anhydrous THF (150 mL) and sodium borohydride (6.26 g, 166 mmol) added portion-wise at 0° C. The pale yellow suspension was stirred at 0° C. for 1 h then at r.t. for a further 20 h. After this time the reaction was carefully quenched with ice-water (25 mL), and volatile solvents removed under reduced pressure. The residue was partitioned between EtOAc (200 mL) and water (150 mL). The organic layers were extracted, washed with brine (150 mL) then dried, filtered (phase separation cartridge) and concentrated to give a colorless oil. The oil was triturated from iso-hexane/diethyl ether to give the title compound as a colorless solid (7.2 g, 82%).

Step 2: 1-(bromomethyl)-3,4-difluoro-2-methylbenzene

To a 4° C. solution of (3,4-difluoro-2-methylphenyl)methanol (7.0 g, 44.2 mmol) and carbon tetrabromide (17.6 g, 53.2 mmol) in anhydrous dichloromethane (100 mL) was added a dropwise solution of triphenylphosphine (14.0 g, 53.2 mmol) in DCM (25 mL). The reaction mixture was warmed to r.t. and stirred for 20 h. After this time the reaction mixture was concentrated under reduced pressure and the crude residue passed through a pad of silica gel (elution: iso-hexane/diethyl ether). Fractions containing the desired product were concentrated under reduced pressure to give a pale yellow oil. The crude reaction material was purified by flash silica chromatography (gradient elution iso-hexane to 20% EtOAc in iso-hexane) to give the title compound as a pale yellow oil (11.8 g) in an approximately 5:1 ratio with bromoform.

Step 3: 2-(3,4-difluoro-2-methylphenyl)acetonitrile

To a 4° C. solution of 1-(bromomethyl)-3,4-difluoro-2-methylbenzene (10.0 g, 45.2 mmol) and sodium cyanide (3.32 g, 67.8 mmol) in DMF (65 mL) was added water (8 mL). The reaction mixture was stirred at 4° C. for 3 hours. After this time the reaction mixture was partitioned between sat. aq. NaHCO$_3$/water (1:1, 300 mL) and diethyl ether (200 mL). The aqueous layer was extracted with diethyl ether (2×200 mL); the combined organics were washed with brine (150 mL) then dried, filtered (phase separation cartridge) and concentrated to give a brown oil. The crude reaction material was purified by flash silica chromatography (gradient elution, 0-33% EtOAc in iso-hexane) to give the title compound as a yellow oil (6.2 g, 83%).

Step 4: 2-(3,4-difluoro-2-methylphenyl)acetic Acid

To a solution of 2-(3,4-difluoro-2-methylphenyl)acetonitrile (6.20 g, 37.1 mmol) in acetic acid (30 mL) was added c.H$_2$SO$_4$/water (1:1, 25 mL) and the reaction mixture was refluxed for 24 h. After this time the reaction mixture was cooled to r.t. and adjusted to pH 3 using solid Na$_2$CO$_3$. The aqueous reaction mixture was then extracted with dichloromethane (3×50 mL). The combined organics were washed with water (65 mL) and brine (65 mL), then dried, filtered (phase separation cartridge) and concentrated to give a pale yellow solid. The solid was triturated from iso-hexane/diethyl ether to give the title compound as a colorless solid (6.5 g, 94%).

Step 5: methyl 2-(3,4-difluoro-2-methylphenyl)acetate

To a solution of 2-(3,4-difluoro-2-methylphenyl)acetic acid (6.52 g, 35.0 mmol) in methanol (100 mL) was added c.H$_2$SO$_4$ (0.1 mL, cat.) and the reaction mixture was refluxed for 20 h. After this time the reaction mixture was cooled to r.t. and concentrated under reduced pressure. The crude residue was partitioned between EtOAc (75 mL) and sat. aq. NaHCO$_3$/water (1:1, 50 mL). The aqueous layer was extracted with EtOAc (2×50 mL); the combined organics washed with brine (50 mL), dried, filtered (phase separation cartridge) and concentrated to give a pale yellow oil. The crude reaction material was purified by flash silica chromatography (gradient elution, 0-15% EtOAc in iso-hexane) to give the title compound as a colorless oil (7.12 g, 95%).

Step 6: (1S,3S)-methyl 1-(3,4-difluoro-2-methylphenyl)-3-hydroxycyclopentanecarboxylate To a solution of (S)-tert-butyl((1,4-dibromobutan-2-yl)oxy)diphenylsilane (4.70 g, 0.010 mol) and methyl 2-(3,4-difluoro-2-methylphenyl)acetate (2.0 g, 0.010 mol) in anhydrous DMF (90 mL) was added 18-crown-6 (0.1 g, catalytic). The reaction mixture was stirred at r.t. for 10 min then sodium hydride (60% dispersion in mineral oil 0.96 g, 0.025 mol) was added portion-wise over 1.5 h. Reaction mixture was stirred at r.t. for a further 1.5 h. The reaction mixture was cooled to 4° C. and quenched by drop-wise addition of sat. aq. NH$_4$Cl solution (10 mL) and residual DMF removed under reduced pressure. The residue was then partitioned between Et$_2$O (240 mL) and water (100 mL). The organic layer was washed with further water (150 mL) and brine (200 mL), then dried, filtered (phase separation cartridge) and concentrated to give a yellow oil. This oil was dissolved in anhydrous THF (75 mL) and TBAF (1 M in THF, 0.02 mol, 20 mL) was added. Reaction mixture was then stirred at r.t. for 2 h. After this time the reaction mixture was concentrated under reduced pressure and purified by silica column chromatography (gradient elution, 0-40% EtOAc in iso-hexane) to give the title compound as a colorless oil (2.30 g, 83%, 8:1 mixture with (1R,3S)-methyl 1-(3,4-difluoro-2-methylphenyl)-3-hydroxycyclopentanecarboxylate). 625 mg of the title compound was separated from the mixture of isomers. R$_f$=0.1 (20% EtOAc/iso-hexane); MS (ES+) consistent with target (M+H)$^+$.

Step 7: (S)-methyl 1-(3,4-difluoro-2-methylphenyl)-3-oxocyclopentanecarboxylate To a solution of (1S,3S)-methyl 1-(3,4-difluoro-2-methylphenyl)-3-hydroxycyclopentanecarboxylate (0.60 g, 2.2 mmol) in anhydrous dichloromethane (30 mL) was added Dess-Martin Periodinane (1.20 g, 2.76 mmol). The reaction mixture was stirred at r.t. for 20 h. Reaction mixture was quenched with a mixture of 10% Na$_2$S$_2$O$_3$ and sat. aq. NaHCO$_3$ solution (1:1, 100 mL) and then rapidly stirred for 30 min. Organic layers were extracted with further CH$_2$Cl$_2$ (2×50 mL), then dried, filtered (phase separation cartridge) and concentrated to give a pale yellow oil. The residue was purified by silica column chromatography (gradient elution, 0-20% EtOAc in iso-hexane) to give the title compound as a colorless oil (0.58 g, 92%, >99.5% ee).

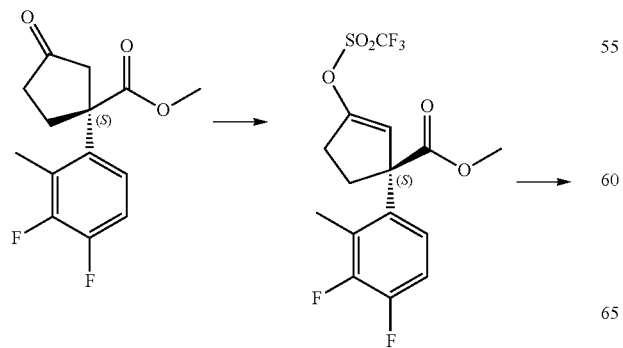

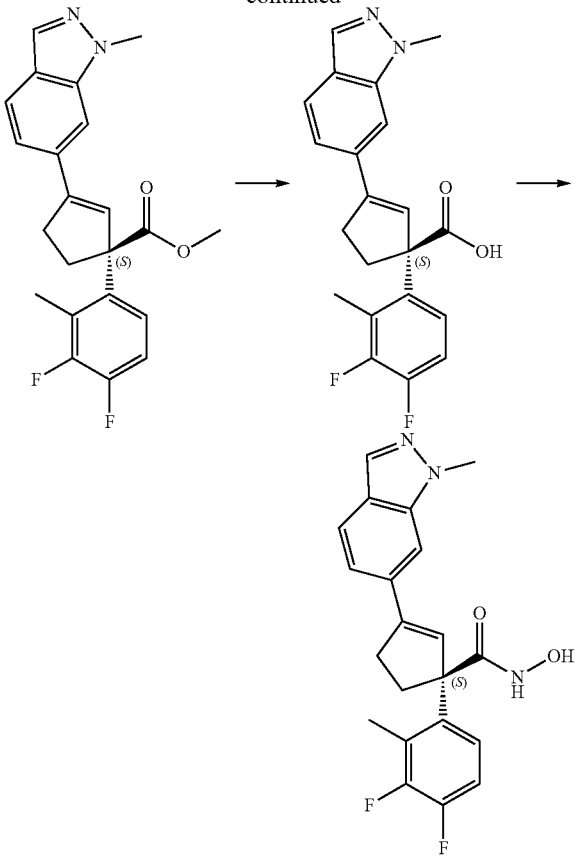

Step 8: (S)-methyl 1-(3,4-difluoro-2-methylphenyl)-3-(((trifluoromethyl)sulfonyl)oxy)cyclopent-2-enecarboxylate Following Method A using (S)-methyl 1-(3,4-difluoro-2-methylphenyl)-3-oxocyclopentanecarboxylate (0.62 g, 2.32 mmol). The residue was purified by silica column chromatography (gradient elution, 0-25% EtOAc in iso-hexane) to give the title compound as a colorless oil (0.64 g, 81%).

Step 9: (S)-methyl 1-(3,4-difluoro-2-methylphenyl)-3-(1-methyl-1H-indazol-6-yl)cyclopent-2-enecarboxylate Following Method B (ii) using (S)-methyl 1-(3,4-difluoro-2-methylphenyl)-3-(((trifluoromethyl)sulfonyl)oxy) cyclopent-2-enecarboxylate (0.62 g, 1.55 mmol) and (1-methyl-1H-indazol-6-yl) boronic acid (0.34 g, 1.90 mmol). The residue was purified by silica column chromatography (gradient elution, 0-35% EtOAc in iso-hexane) to give the title compound as a colorless oil (0.58 g, 97%).

Step 10: (S)-1-(3,4-difluoro-2-methylphenyl)-3-(1-methyl-1H-indazol-6-yl)cyclopent-2-enecarboxylic Acid Following Method C (ii) using (S)-methyl 1-(3,4-difluoro-2-methylphenyl)-3-(1-methyl-1H-indazol-6-yl)cyclopent-2-enecarboxylate (0.57 g, 1.55 mmol). The crude reaction material was azeotroped with CHCl$_3$ to give the title compound as a colorless foam (0.55 g, 95%).

Step 11: (S)-1-(3,4-difluoro-2-methylphenyl)-N-hydroxy-3-(1-methyl-1H-indazol-6-yl)cyclopent-2-enecarboxamide Following Method D using (S)-1-(3,4-difluoro-2-methylphenyl)-3-(1-methyl-1H-indazol-6-yl)cyclopent-2-enecarboxylic acid (0.10 g, 0.27 mmol). The crude residue was purified by preparative HPLC to give the title compound as a colorless solid (65 mg, 64%). LCMS (ES+) 384 (M+H)+, RT 3.73 min (Analytical method 1); $^1$H NMR δ (ppm) (DMSO-d$_6$): 10.13 (1H, s), 8.74 (1H, s), 8.00 (1H, d, J=0.9 Hz), 7.72 (1H, d, J=8.47 Hz), 7.68 (1H, s), 7.43 (1H, dd, J=8.5, 1.4 Hz), 7.20-7.10 (2H, m), 6.54 (1H, s), 4.05 (3H, s), 3.28-3.21 (1H, m), 3.02-2.91 (1H, m), 2.84-2.75 (1H, m), 2.17 (3H, d, J=2.7 Hz), 1.89-1.81 (1H, m).

Example 43: 4-(5-fluoropyridin-3-yl)-N-hydroxy-1,2,3,6-tetrahydro-[1,1'-biphenyl]-1-carboxamide

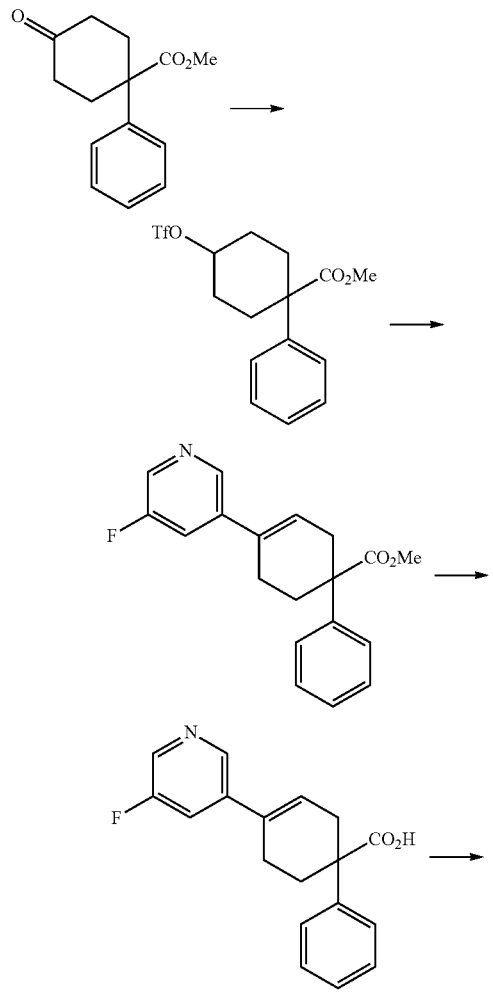

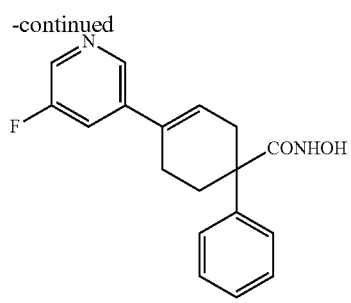

Step 1: methyl 4-(((trifluoromethyl)sulfonyl)oxy)-1,2,3,6-tetrahydro-[1,1'-biphenyl]-1-carboxylate Methyl 4-oxo-1-phenylcyclohexanecarboxylate (993 mg, 4.28 mmol), and THF (30 mL) were combined under nitrogen at room temperature. Reaction mixture was cooled with an ice bath and NaHMDS (1 M in THF, 5.64 mL, 5.64 mmol) was added dropwise. After 30 mins N-(5-chloro-2-pyridyl)bis(trifluoromethanesulfonimide) (1.68 g, 4.28 mmol) was added and the reaction mixture allowed to warm to room temperature with stirring over 4 h. Reaction mixture was diluted with CH$_2$Cl$_2$, washed with water and the organics evaporated to dryness onto silica and purified by flash chromatography to give the title compound as a clear oil (445 mg, 29%).

Step 2: methyl 4-(5-fluoropyridin-3-yl)-1,2,3,6-tetrahydro-[1,1'-biphenyl]-1-carboxylate Methyl 4-(((trifluoromethyl)sulfonyl)oxy)-1,2,3,6-tetrahydro-[1,1'-biphenyl]-1-carboxylate (445 mg, 1.22 mmol), 3-fluoropyridine-5-boronic acid (171 mg, 1.22 mmol), CsF (200 mg), DME (12 mL), MeOH (3 mL) and palladium tetrakis(triphenylphosphine) (20 mg) were combined in a sealed tube and microwave heated to 120° C. for 4 h. Reaction mixture was allowed to cool to room temperature, evaporated to dryness onto silica and purified by flash chromatography to give the title compound as a white solid (216 mg, 57%). MS (ES+) consistent with target (M+H)+.

Step 3: 4-(5-fluoropyridin-3-yl)-1,2,3,6-tetrahydro-[1,1'-biphenyl]-1-carboxylic Acid Methyl 4-(5-fluoropyridin-3-yl)-1,2,3,6-tetrahydro-[1,1'-biphenyl]-1-carboxylate (215 mg, 0.69 mmol), MeOH (20 mL), 15% aq. NaOH soln. (2 mL) were combined in a sealed tube and heated to 65° C. for 24 hours. Reaction mixture was evaporated to dryness then partitioned between EtOAc and H$_2$O/AcOH. Organic layer was dried (MgSO$_4$) and evaporated to dryness to give the title compound as a white solid (176 mg, 86%). MS (ES+) consistent with target (M+H)+.

Step 4: 4-(5-fluoropyridin-3-yl)-N-hydroxy-1,2,3,6-tetrahydro-[1,1'-biphenyl]-1-carboxamide 4-(5-Fluoropyridin-3-yl)-1,2,3,6-tetrahydro-[1,1'-biphenyl]-1-carboxylic acid (176 mg, 0.57 mmol), DMF (3 mL), Et$_3$N (0.24 mL, 1.7 mmol) and TFFH (225 mg, 0.855 mmol) were combined and stirred at room temperature under a nitrogen atmosphere. After 30 min H$_2$NOTHP (94 mg, 0.8 mmol) was added and the reaction stirred for 18 h. MeOH (3 mL) and 2 N HCl in diethyl ether (2 mL) were then added and reaction stirred for 2 h. Volatile solvents were removed in vacuo and the residue purified by preparative HPLC to give the title compound as a white solid (136 mg, 76%). LCMS (ES+) 313 (M+H)+, RT 3.20 min (Analytical method 1); $^1$H NMR δ (ppm) (DMSO-$d_6$): 10.49 (1H, s), 8.73 (1H, s), 8.56 (1H, t, J=2.0 Hz), 8.46 (1H, d, J=2.6 Hz), 7.79-7.74 (1H, m), 7.43 (2H, d, J=7.4 Hz), 7.37 (2H, t, J=7.7 Hz), 7.27 (1H, t, J=7.2 Hz), 6.56 (1H, t, J=4.0 Hz), 3.06-2.97 (1H, m), 2.70-2.62 (1H, m), 2.52-2.46 (2H, m), 2.31-2.22 (2H, m).

Example 44: 3'-fluoro-4-(5-fluoropyridin-3-yl)-N-hydroxy-2'-methyl-1,2,3,6-tetrahydro-[1,1'-biphenyl]-1-carboxamide

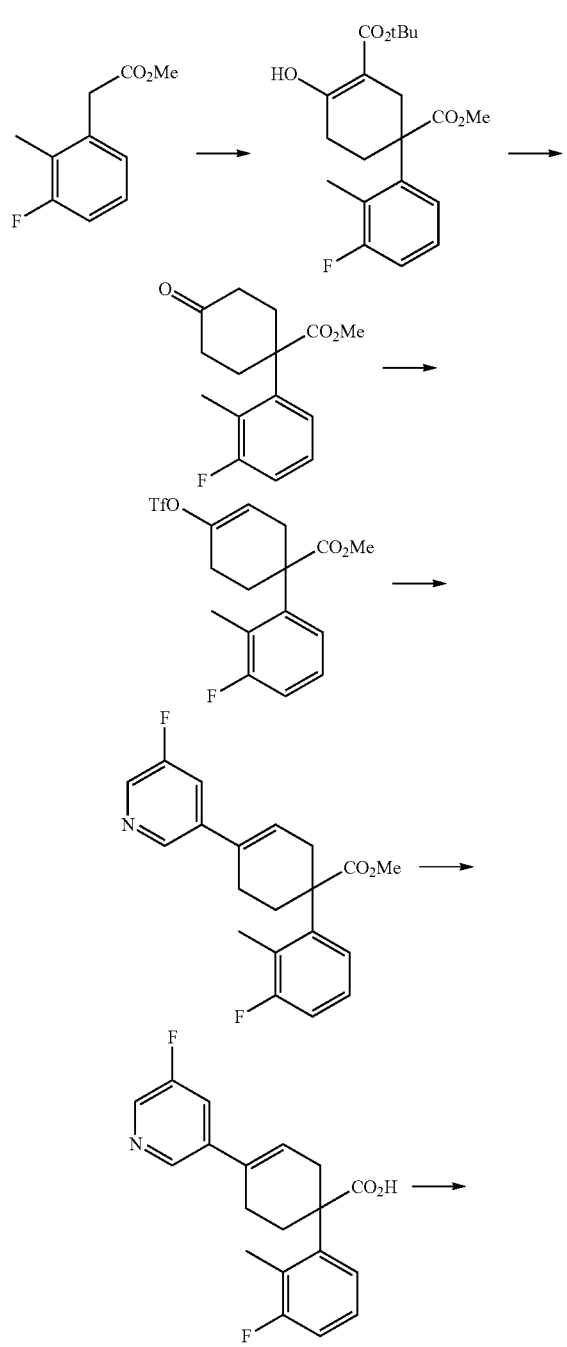

Step 1: 3-tert-butyl 1-methyl 3'-fluoro-4-hydroxy-2'-methyl-1,2,5,6-tetrahydro-[1,1'-biphenyl]-1,3-dicarboxylate Methyl 2-(3-fluoro-2-methylphenyl)acetate (3.13 g, 17.2 mmol), DMF (30 mL) and tert-butyl acrylate (5.22 mL, 36.12 mmol) were combined at room temperature under a nitrogen atmosphere. Reaction mixture was cooled with an ice bath and NaH (60% in oil) (3.44 g, 86 mmol) was added portionwise. Reaction mixture was stirred at room temperature for 20 h and then carefully quenched with sat. aq. NH$_4$Cl solution with ice bath cooling. The reaction mixture was extracted with EtOAc, then washed with water and brine and evaporated to dryness onto silica before purification by flash chromatography. The title compound was obtained as a white solid (2.14 g, 34%).

Step 2: methyl 1-(3-fluoro-2-methylphenyl)-4-oxo-cyclohexanecarboxylate 3-tert-Butyl 1-methyl 3'-fluoro-4-hydroxy-2'-methyl-1,2,5,6-tetrahydro-[1,1'-biphenyl]-1,3-dicarboxylate (2.14 g, 5.88 mmol) and TFA (10 mL) were combined and stirred at room temperature for 20 h. The TFA was removed by evaporation in vacuo and the residue was azeotroped with toluene. Toluene (100 mL), MeOH (10 mL) and NaHCO$_3$ (200 mg) were added and the mixture was heated to 105° C. for 20 h. The reaction mixture was then evaporated to dryness onto silica and purified by flash chromatography to give the title compound as a white solid (799 mg, 52%). MS (ES+) consistent with target (M+H)+.

Step 3: methyl 3'-fluoro-2'-methyl-4-(((trifluoromethyl)sulfonyl)oxy)-1,2,3,6-tetrahydro-[1,1'-biphenyl]-1-carboxylate Methyl 1-(3-fluoro-2-methylphenyl)-4-oxocyclohexanecarboxylate (790 mg, 2.99 mmol) and THF (20 mL) were combined under a nitrogen atmosphere and cooled with an ice bath. NaHMDS (1 M in THF, 4.5 mL, 4.5 mmol) was added dropwise followed after 20 minutes by N-(5-chloropyridin-2-yl)-1,1,1-trifluoro-N-((trifluoromethyl)sulfonyl)methanesulfonamide (1.38 g, 3.5 mmol). Reaction mixture was allowed to warm to room temperature and stirred for 3 h. Reaction mixture was then diluted with CH$_2$Cl$_2$, washed with water, evaporated to dryness onto silica and purified by flash chromatography to give the title compound as a colorless oil (730 mg, 62%).

Step 4: methyl 3'-fluoro-4-(5-fluoropyridin-3-yl)-2'-methyl-1,2,3,6-tetrahydro-[1,1'-biphenyl]-1-carboxylate Methyl 3'-fluoro-2'-methyl-4-(((trifluoromethyl)sulfonyl)oxy)-1,2,3,6-tetrahydro-[1,1'-biphenyl]-1-carboxylate (326 mg, 0.82 mmol), 5-fluoropyridine-3-boronic acid (116 mg, 0.82 mmol), CsF (120 mg), DME (12 mL), MeOH (2 mL) and palladium tetrakis(triphenylphosphine) (10 mg) were combined in a sealed tube and heated by microwave to 120° C. for 2 h. The reaction mixture was then evaporated to dryness onto silica and purified by flash chromatography to give the title compound as a crystalline solid (234 mg, 83%). MS (ES+) consistent with target (M+H)+.

Step 5: 3'-fluoro-4-(5-fluoropyridin-3-yl)-2'-methyl-1,2,3,6-tetrahydro-[1,1'-biphenyl]-1-carboxylic Acid Methyl 3'-fluoro-4-(5-fluoropyridin-3-yl)-2'-methyl-1,2,3,6-tetrahydro-[1,1'-biphenyl]-1-carboxylate (230 mg, 0.67 mmol), MeOH (15 mL) and 15% aq. NaOH solution (2 mL) were combined in a sealed tube and heated to 65° C. for 13 days. The reaction mixture was then evaporated in vacuo then partitioned between EtOAc and H₂O/AcOH. Organic layer was dried (MgSO₄) and evaporated in vacuo to give the title compound as a cream solid (181 mg, 82%). MS (ES+) consistent with target (M+H)+.

Step 6: 3'-fluoro-4-(5-fluoropyridin-3-yl)-N-hydroxy-2'-methyl-1,2,3,6-tetrahydro-[1,1'-biphenyl]-1-carboxamide 3'-Fluoro-4-(5-fluoropyridin-3-yl)-2'-methyl-1,2,3,6-tetrahydro-[1,1'-biphenyl]-1-carboxylic acid (180 mg, 0.547 mmol), TFFH (188 mg, 0.71 mmol), DMF (3 mL) and Et₃N (0.35 mL, 2.5 mmol) were combined and stirred at room temperature under a nitrogen atmosphere. After 1 h O-(tetrahydro-2H-pyran-2-yl)hydroxylamine (117 mg, 1 mmol) was added and the mixture stirred for 4 days. MeOH (2 mL) and 2 N HCl in diethyl ether (2 mL) were both added and the mixture stirred for 17 h. Volatile solvents were removed in vacuo and the crude material was purified by preparative HPLC to give the title compound as a white solid (92 mg, 49%). LCMS (ES+) 345 (M+H)+, RT 3.27 min (Analytical method 1); ¹H NMR δ (ppm) (DMSO-d₆): 10.15 (1H, s), 8.71 (1H, br s), 8.51 (1H, t, J=1.6 Hz), 8.42 (1H, d, J=2.8 Hz), 7.71 (1H, dt, J=10.8, 2.4 Hz), 7.20-7.00 (3H, m), 6.54 (1H, s), 2.80-2.20 (5H, m), 2.17 (3H, d, J=2.8 Hz), 1.88-1.75 (1H, m).

Example 45: 3'-fluoro-N-hydroxy-2'-methyl-4-(quinoxalin-6-yl)-1,2,3,6-tetrahydro-[1,1'-biphenyl]-1-carboxamide

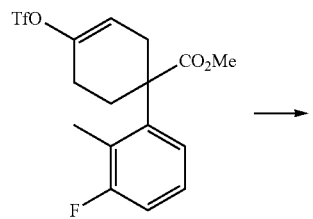

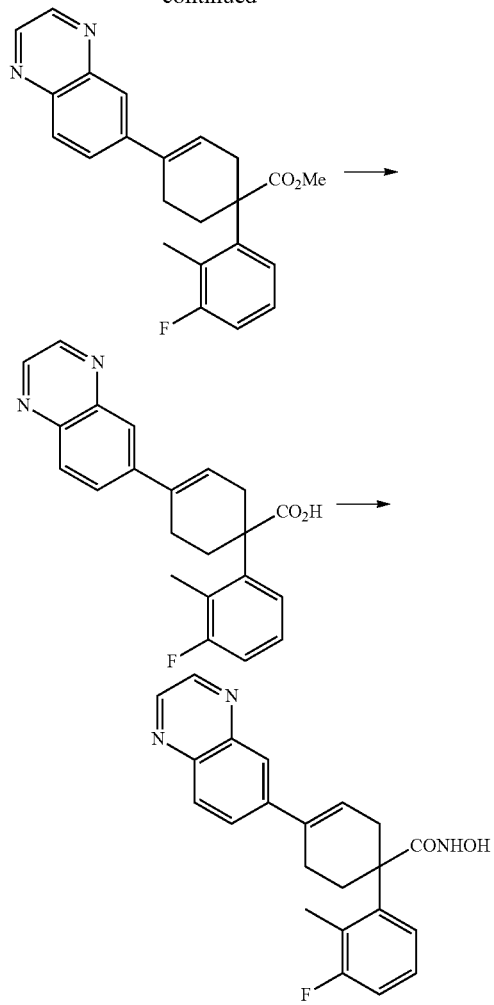

Step 1: methyl 3'-fluoro-2'-methyl-4-(quinoxalin-6-yl)-1,2,3,6-tetrahydro-[1,1'-biphenyl]-1-carboxylate Methyl 3'-fluoro-2'-methyl-4-(((trifluoromethyl)sulfonyl)oxy)-1,2,3,6-tetrahydro-[1,1'-biphenyl]-1-carboxylate (399 mg, 1 mmol), quinoxaline-6-boronic acid.HCl (211 mg, 1 mmol), CsF (200 mg), DME (15 ml), MeOH (2 ml) and palladium tetrakis triphenylphosphine (10 mg) were combined in a sealed tube and heated by microwave to 120° C. for 2 h. The reaction mixture was then evaporated to dryness onto silica and purified by flash chromatography to give the title compound as a tan gum (213 mg, 57%). LCMS (ES+) 377 (M+H)+.

Step 2: 3'-fluoro-2'-methyl-4-(quinoxalin-6-yl)-1,2,3,6-tetrahydro-[1,1'-biphenyl]-1-carboxylic Acid Methyl 3'-fluoro-2'-methyl-4-(quinoxalin-6-yl)-1,2,3,6-tetrahydro-[1,1'-biphenyl]-1-carboxylate (210 mg, 0.56 mmol), MeOH (15 ml) and 15% aq. NaOH solution (2 ml) were combined in a sealed tube and heated to 65° C. for 20 days. The reaction mixture was then evaporated in vacuo then partitioned between EtOAc and H₂O/AcOH. Organic layer was dried (MgSO₄) and evaporated in vacuo to give the title compound as a brown solid (140 mg, 69%). LCMS (ES+) 363 (M+H)+.

Step 3: 3'-fluoro-N-hydroxy-2'-methyl-4-(quinoxalin-6-yl)-1,2,3,6-tetrahydro-[1,1'-biphenyl]-1-carboxamide 3'-Fluoro-2'-methyl-4-(quinoxalin-6-yl)-1,2,3,6-tetrahydro-[1,1'-biphenyl]-1-carboxylic acid (140 mg, 0.39 mmol), TFFH (143 mg, 0.54 mmol), DMF (2 mL) and Et$_3$N (0.17 mL, 1.2 mmol) were combined and stirred at room temperature under a nitrogen atmosphere. After 40 minutes O-(tetrahydro-2H-pyran-2-yl)hydroxylamine (117 mg, 1 mmol) was added and the mixture stirred for 4 days. MeOH (2 mL) and 2 N HCl in diethyl ether (2 mL) were added and the mixture stirred for 4 h. Volatile solvents were removed in vacuo and the remaining material was purified by preparative HPLC to give the title compound as a pale yellow solid (64 mg, 44%). LCMS (ES+) 378 (M+H)$^+$; $^1$H NMR δ (ppm) (DMSO-d$_6$): 10.18 (1H, s), 8.91 (1H, d, J=1.6 Hz), 8.87 (1H, d, J=1.6 Hz), 8.72 (1H, s), 8.08-8.00 92H, m), 7.89 (1H, s), 7.20-7.00 (3H, m), 6.68 (1H, s), 2.85-2.25 (5H, m), 2.20 (3H, d, J=2.8 Hz), 2.05-1.90 (1H, m).

Example 46: Analysis of Inhibition of HDAC4 with Class IIa Histone Deacetylase (HDAC) Inhibitors The potency of Class IIa Histone Deacetylase (HDAC) inhibitors is quantified by measuring the Histone Deacetylase 4 (HDAC4) catalytic domain enzymatic activity using the fluorogenic substrate, Boc-Lys(Tfa)-AMC. The substrate is deacetylated to Boc-Lys-AMC by HDAC4. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% dimethyl sulfoxide (DMSO). Stocks of 60 μl aliquots of the 10 mM compound in DMSO are prepared and stored at −20° C. From one stock aliquot of each compound to be tested and the reference compound, a 16-point serial dilution is prepared according to Table 7 using a 125 μl 16-channel Matrix multi-channel pipette (Matrix Technologies Ltd).

TABLE 1

Serial Dilution of Compounds

| Diluted Solutions | Well | Concentration (μM) | Dilution ratio | Volumes |
|---|---|---|---|---|
| Concentration 1 | A | 10000 | — | 60 μl 10 mM Test compound/reference control |
| Concentration 2 | B | 5000 | 1:2 | 30 μl A + 30 μl DMSO |
| Concentration 3 | C | 2500 | 1:2 | 30 μl B + 30 μl DMSO |
| Concentration 4 | D | 1000 | 1:2.5 | 30 μl C + 45 μl DMSO |
| Concentration 5 | E | 500 | 1:2 | 30 μl D + 30 μl DMSO |
| Concentration 6 | F | 250 | 1:2 | 30 μl E + 30 μl DMSO |
| Concentration 7 | G | 125 | 1:2 | 30 μl F + 30 μl DMSO |
| Concentration 8 | H | 62.5 | 1:2 | 30 μl G + 30 μl DMSO |
| Concentration 9 | I | 31.25 | 1:2 | 30 μl H + 30 μl DMSO |
| Concentration 10 | J | 15.63 | 1:2 | 30 μl I + 30 μl DMSO |
| Concentration 11 | K | 7.81 | 1:2 | 30 μl J + 30 μl DMSO |
| Concentration 12 | L | 3.91 | 1:2 | 30 μl K + 30 μl DMSO |
| Concentration 13 | M | 1.95 | 1:2 | 30 μl L + 30 μl DMSO |
| Concentration 14 | N | 0.98 | 1:2 | 30 μl M + 30 μl DMSO |
| Concentration 15 | O | 0.49 | 1:2 | 30 μl N + 30 μl DMSO |
| Concentration 16 | P | 0.24 | 1:2 | 30 μl O + 30 μl DMSO |

2 μl (200×) of each diluted solution and each control (full activity: 100% DMSO alone or full inhibition 1 mM) is stamped into V-bottomed polypropylene 384-well compound plates using either the Bravo (384-well head from Agilent) or 12.5 μl 16-channel Matrix multi-channel pipette (Matrix Technologies Ltd). Each well with the 200× compound solution is diluted 1:20 by the addition of 38 μl assay buffer+DMSO (10.5% DMSO, 45 mM Tris-HCl, 123 mM NaCl, 2.4 mM KCl, and 0.9 mM MgCl$_2$ at pH 8.0 and equilibrated to room temperature).

Prepare HDAC4 Catalytic Domain Enzyme (0.2 μg/ml).

The HDAC4 catalytic domain enzyme is human catalytic domain HDAC4 protein (amino acids 648-1032) with a C-terminal 6× histidine tag, produced by BioFocus. A working solution of enzyme is prepared from a 500 μg/ml stock aliquot of HDAC4 catalytic domain (thawed on ice) diluted to 0.2 μg/ml with assay buffer (50 mM Tris-HCl, 137 mM NaCl, 2.7 mM KCl, and 1 mM MgCl$_2$ at pH 8 and equilibrated to room temperature) just prior to the addition of the enzyme to the assay.

Prepare 5× (50 μM) Boc-Lys(Tfa)-AMC Substrate.

5× (50 μM) substrate is prepared just prior to the addition to the assay. A 1 mM substrate stock is made by diluting a 100 mM Boc-Lys(Tfa)-AMC in DMSO solution 1:100 by adding it drop-wise to assay buffer (equilibrated to room temperature) while vortexing at slow speed to prevent precipitation. The 5× substrate is prepared by diluting the 1 mM substrate solution 1:20 by adding it drop-wise to assay buffer (equilibrated to room temperature) while vortexing at slow speed to prevent precipitation.

Prepare 3× (30 μM) Developer/Stop Solution.

3× (30 μM) Developer/Stop Solution is prepared just prior to addition to the plate by diluting a stock solution of 10 mM reference compound 1:333 in 25 mg/ml trypsin (PAA Laboratories Ltd.) equilibrated to room temperature.

Assay.

5 μl of each solution of 1:20 diluted compound from above is transferred to a clear bottomed, black, 384-well assay plate using the Bravo or the Janus (384-well MDT head from Perkin Elmer). Using a 16-channel Matrix multi-channel pipette, 35 μl of the working solution of HDAC4 catalytic domain enzyme (0.2 μg/ml in assay buffer) is transferred to the assay plate. The assay is then started by adding 10 μl of 5× (50 μM) substrate to the assay plates using either the Bravo, Janus or 16-channel Matrix multi-channel pipette. The assay plate is then shaken for two minutes on an orbital shaker at 900 rpm (rotations per minute). Next the plate is incubated for 15 minutes at 37° C. The reaction is stopped by adding 25 µl of 3× (30 µM) developer/stop solution to the assay plates using either the Bravo, Janus or a 16-channel Matrix multi-channel pipette. Assay plates are then shaken for 5 minutes on an orbital shaker at 1200 rpm. Next, the assay plates are incubated at 37° C. for 1 hour in a tissue culture incubator. Finally, the fluorescence is measured (Excitation: 355 nm, Emission: 460 nm) using PerkinElmer EnVision in top read mode.

Example 47: Analysis of Inhibition of HDAC5 with Class IIa Histone Deacetylase (HDAC) Inhibitors The potency of Class IIa Histone Deacetylase (HDAC) inhibitors is quantified by measuring the Histone Deacetylase 5 (HDAC5) enzymatic activity using the fluorogenic substrate, Boc-Lys(Tfa)-AMC. The substrate is deacetylated to Boc-Lys-AMC by HDAC5. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µl aliquots of the 10 mM compound in DMSO are prepared and stored at −20° C. From one stock aliquot of each compound to be tested and the reference compound, a 16-point serial dilution is prepared according to Table 7 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either Bravo, Janus, or a 12.5 µl 16-channel Matrix multi-channel pipette. Each well with the 2 µl of the 200× stamped compound solution is diluted 1:20 by the addition of 38 µl assay buffer+DMSO (10.5% DMSO, 45 mM Tris-HCl, 123 mM NaCl, 2.4 mM KCl, and 0.9 mM MgCl$_2$ at pH 8.0 and equilibrated to 37° C.).

Prepare HDAC5 Catalytic Domain Enzyme (0.57 µg/ml).

The HDAC5 catalytic domain enzyme is human HDAC5 catalytic domain (GenBank Accession No. NM_001015053), amino acids 657-1123 with a C-terminal His tag and can be obtained from BPS BioScience. The protein is 51 kDa and is expressed in a baculovirus expression system. A working solution of enzyme is prepared from a 1.65 mg/ml stock aliquot of HDAC5 catalytic domain (thawed on ice) diluted to 0.57 µg/ml with assay buffer (50 mM Tris-HCl, 137 mM NaCl, 2.7 mM KCl, and 1 mM MgCl$_2$ at pH 8 and equilibrated to 37° C.) just prior to the addition of the enzyme to the assay.

Prepare 5× (40 µM) Boc-Lys(Tfa)-AMC Substrate.

5× (40 µM) substrate is prepared just prior to the addition to the assay. The 5× substrate is prepared by diluting the 100 mM Boc-Lys(Tfa)-AMC in DMSO solution 1:2500 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/ml trypsin equilibrated to 37° C.

Assay.

5 µl of each solution of the 1:20 diluted inhibitor compounds and controls from above is transferred to a clear bottomed, black, 384-well assay plate using the Bravo or Janus. Using a 16-channel Matrix multi-channel pipette, 35 µl of the working solution of the HDAC5 catalytic domain enzyme (0.57 µg/ml in assay buffer) is transferred to the assay plate. The assay is then started by adding 10 µl of 5× (40 µM) substrate to the assay plates using either the Bravo, Janus or 16-channel Matrix multi-channel pipette. The assay plate is then shaken for one minute on an orbital shaker at 900 rpm. Next, the plates are incubated for 15 minutes at 37° C. The reaction is stopped by adding 25 µl of 3× (30 µM) developer/stop solution to the assay plates using either the Bravo, Janus or a 16-channel Matrix multi-channel pipette. Assay plates are then shaken for 2 minutes on an orbital shaker at 900 rpm. Next, the assay plates are incubated at 37° C. for 1 hour in a tissue culture incubator followed by shaking for 1 minute at the maximum rpm on an orbital shaker before reading on the EnVision. Finally, the fluorescence is measured (Excitation: 355 nm, Emission: 460 nm) using PerkinElmer EnVision in top read mode.

Example 48: Analysis of Inhibition of HDAC7 with Class IIa Histone Deacetylase (HDAC) Inhibitors The potency of Class IIa Histone Deacetylase (HDAC) inhibitors is quantified by measuring the Histone Deacetylase 7 (HDAC7) enzymatic activity using the fluorogenic substrate, Boc-Lys(Tfa)-AMC. The substrate is deacetylated to Boc-Lys-AMC by HDAC7. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µl aliquots of the 10 mM compound in DMSO are prepared and stored at −20° C. From one stock aliquot of each compound to be tested and the reference compound, a 16-point serial dilution is prepared according to Table 7 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either the Bravo, Janus, or a 12.5 µl 16-channel Matrix multi-channel pipette. Each well with the 200× compound solution is diluted 1:20 by the addition of 38 µl assay buffer+DMSO (10.5% DMSO, 45 mM Tris-HCl, 123 mM NaCl, 2.4 mM KCl, and 0.9 mM MgCl$_2$ at pH 8.0 and equilibrated to 37° C.).

Prepare HDAC7 Enzyme (71 ng/ml).

The HDAC7 enzyme is human HDAC7 (GenBank Accession No. AY302468) amino acids 518-end with a N-terminal Glutathione S-transferase (GST) tag and can be obtained from BPS BioScience. The protein is 78 kDa and is expressed in a baculovirus expression system. A working solution of enzyme is prepared from a 0.5 mg/ml stock aliquot of HDAC7 (thawed on ice) diluted to 71 ng/ml with assay buffer (50 mM Tris-HCl, 137 mM NaCl, 2.7 mM KCl, and 1 mM MgCl$_2$ at pH 8 and equilibrated to 37° C.) just prior to the addition of enzyme to the assay.

Prepare 5× (50 µM) Boc-Lys(Tfa)-AMC Substrate.

5× (50 µM) substrate is prepared just prior to the addition to the assay. The 5× substrate is prepared by diluting a 100 mM Boc-Lys(Tfa)-AMC in DMSO solution 1:2000 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/ml trypsin equilibrated to 37° C.

Assay.

5 µl of each solution of 1:20 diluted compound from above is transferred to a clear bottomed, black, 384-well assay plate using the Bravo or Janus. Using a 16-channel Matrix multi-channel pipette, 35 µl of the working solution of the HDAC7 enzyme (71 ng/ml in assay buffer) is transferred to the assay plate. The assay is then started by adding 10 µl of 5× (50 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is then stopped by adding 25 µl of 3× (30 µM) developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker. Finally, the fluorescence is measured (Excitation: 355 nm, Emission: 460 nm) using PerkinElmer EnVision in top read mode.

Example 49: Analysis of Inhibition of HDAC9 with Class IIa Histone Deacetylase (HDAC) Inhibitors The potency of Class IIa Histone Deacetylase (HDAC) inhibitors is quantified by measuring the Histone Deacetylase 9 (HDAC9) enzymatic activity using the fluorogenic substrate, Boc-Lys(Tfa)-AMC. The substrate is deacetylated to Boc-Lys-AMC by HDAC9. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µl aliquots of the 10 mM compound in DMSO are prepared and stored at −20° C. From one stock aliquot of each compound to be tested and the reference compound, a 16-point serial dilution is prepared according to Table 7 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either the Bravo, Janus, or 12.5 µl 16-channel Matrix multi-channel pipette. Each well with the stamped 200× compound solution is diluted 1:20 by the addition of 38 µl assay buffer+DMSO (10.5% DMSO, 45 mM Tris-HCl, 123 mM NaCl, 2.4 mM KCl, and 0.9 mM $MgCl_2$ at pH 8.0 and equilibrated to 37° C.).

Prepare HDAC9 Enzyme (0.57 µg/ml).

The HDAC9 enzyme is human HDAC9 (GenBank Accession No. NM_178423) amino acids 604-1066 with a C-terminal His tag and can be obtained from BPS BioScience. The protein is 50.7 kDa and is expressed in a baculovirus expression system. A working solution of enzyme is prepared from a 0.5 mg/ml stock aliquot of HDAC9 (thawed on ice) diluted to 0.57 µg/ml with assay buffer (50 mM Tris-HCl, 137 mM NaCl, 2.7 mM KCl, and 1 mM $MgCl_2$ at pH 8 and equilibrated to 37° C.) just prior to the addition of enzyme to the assay.

Prepare 5× (125 µM) Boc-Lys(Tfa)-AMC Substrate.

5× (125 µM) substrate is prepared just prior to the addition to the assay. The 5× substrate is prepared by diluting a 100 mM Boc-Lys(Tfa)-AMC in DMSO solution 1:800 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/ml trypsin equilibrated to 37° C.

Assay.

5 µl of each solution of 1:20 diluted compound from above is transferred to a clear bottomed, black, 384-well assay plate using the Bravo or Janus. Using a 16-channel Matrix multi-channel pipette, 35 µl of the working solution of the HDAC9 enzyme (0.57 µg/ml in assay buffer) is transferred to the assay plate. The assay is then started by adding 10 µl of 5× (125 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is stopped by adding 25 µl of 3× developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker before reading on the enVision. Finally, the fluorescence is measured (Excitation: 355 nm, Emission: 460 nm) using PerkinElmer EnVision in top read mode.

Example 50: Analysis of Inhibition of Cellular HDAC Activity with Class IIa Histone Deacetylase (HDAC) Inhibitors The potency of Class IIa Histone Deacetylase (HDAC) inhibitors is quantified by measuring the cellular histone deacetylase enzymatic activity using the fluorogenic substrate, Boc-Lys(Tfa)-AMC. After penetration in Jurkat E6-1 cells, the substrate is deacetylated to Boc-Lys-AMC. After cell lysis and cleavage by trypsin, the fluorophore AMC is released from the deacetylated substrate only. The fluorescence of the sample is directly related to the histone deacetylase activity in the sample.

Jurkat E6.1 Cell Culture and Plating.

Jurkat E6.1 cells are cultured according to standard cell culture protocols in Jurkat E6.1 Growth Media (RPMI without phenol red, 10% FBS, 10 mM HEPES, and 1 mM Sodium Pyruvate). Jurkat E6.1 cells are counted using a Coulter Counter and resuspended in Jurkat E6.1 growth media at a concentration of 75,000 cells/35 µl. 35 µl or 75,000 cells is seeded into Greiner microtitre assay plates. The plates are then incubated at 37° C. and 5% $CO_2$ while other assay components are being prepared.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 70 μl aliquots of the 10 mM compound in DMSO are prepared and stored at −20° C. From one stock aliquot of each compound to be tested and the reference compound, a 16-point serial dilution is prepared according to Table 1 using a 125 μl 16-channel Matrix multi-channel pipette.

2 μl (200×) of each diluted solution and each control (full activity: 100% DMSO alone or full inhibition 1 mM) is stamped into V-bottom polypropylene 384-well compound plates using either the Bravo, Janus, or 12.5 μl 16-channel Matrix multi-channel pipette. Each well with the 200× compound solution is diluted 1:20 by the addition of 38 μl Jurkat assay buffer+DMSO (9.5% DMSO, RPMI without phenol red, 0.09% FBS, 9 mM Hepes, and 0.9 mM Sodium Pyruvate equilibrated to room temperature)

Prepare 5× (500 μM) Boc-Lys(Tfa)-AMC Substrate.

5× (500 μM) substrate is prepared just prior to the addition to the assay. The 5× substrate is prepared by diluting a 100 mM Boc-Lys(Tfa)-AMC in DMSO solution 1:200 by adding it drop-wise to Jurkat assay medium (RPMI without phenol red, 0.1% FBS, 10 mM Hepes, and 1 mM Sodium Pyruvate equilibrated to 37° C.) while vortexing at slow speed to prevent precipitation.

Prepare 3× Lysis Buffer.

10 ml of 3× lysis buffer is prepared with 8.8 ml of 3× stock lysis buffer (50 mM Tris-HCl, pH 8.0, 137 mM NaCl, 2.7 mM KCl, 1 mM $MgCl_2$, 1% Nonidet P40 Substitute equilibrated to room temperature) and 1.2 ml of 3 mg/ml Trypsin equilibrated to room temperature.

Assay.

5 μl of each solution of 1:20 diluted compound from above is transferred to the Greiner microtitre assay plates with 75,000 cells/well using the Bravo. Cells are then incubated for 2 hours at 37° C. and 5% $CO_2$. The assay is then started by adding 10 μl of 5× (500 μM) substrate to the assay plate using either the Bravo or 16-channel Matrix multi-channel pipette. The cells are then incubated for 3 hours at 37° C. and 5% $CO_2$. Next, 25 μl of 3× lysis buffer is added to each well using either the 125 μl 16 channel pipette or the Bravo. The assay plate is then incubated overnight (15-16 hours) at 37° C. and 5% $CO_2$. The following day, the plates are shaken on an orbital shaker for 1 minute at 900 rpm. Finally the top read fluorescence (Excitation: 355 nm, Emission: 460 nm) is measured using PerkinElmer EnVision.

Example 51

Using the synthetic methods similar to those described above and the assay protocols described above, the following compounds were synthesized and tested.

| Example # | Chemical Name | Structure | Biochemical HDAC-4 $IC_{50}$ (μM) | Cell $IC_{50}$ (μM) |
|---|---|---|---|---|
| 1 | (R)-1-(3-Fluoro-2-methylphenyl)-N-hydroxy-3-phenylcyclopent-2-enecarboxamide | 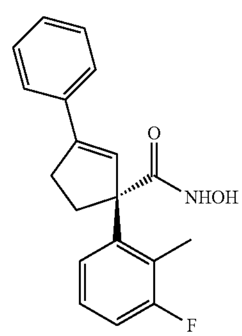 | 7.6 | >50 |
| 2 | (S)-1-(3-Fluoro-2-methylphenyl)-N-hydroxy-3-phenylcyclopent-2-enecarboxamide | 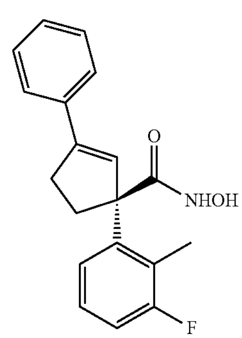 | 0.02 | 0.17 |

| Example # | Chemical Name | Structure | Biochemical HDAC-4 IC$_{50}$ (µM) | Cell IC$_{50}$ (µM) |
|---|---|---|---|---|
| 3 | (R)-1-(3-Fluoro-2-methylphenyl)-N-hydroxy-3-(o-tolyl)cyclopent-2-enecarboxamide | 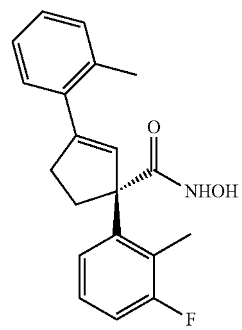 | 0.23 | 4.6 |
| 4 | (S)-1-(3-Fluoro-2-methylphenyl)-N-hydroxy-3-(o-tolyl)cyclopent-2-enecarboxamide | 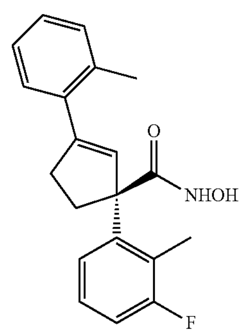 | 0.02 | 0.36 |
| 5 | (R)-1-(3-Fluoro-2-methylphenyl)-3-(5-fluoropyridin-3-yl)-N-hydroxycyclopent-2-enecarboxamide | 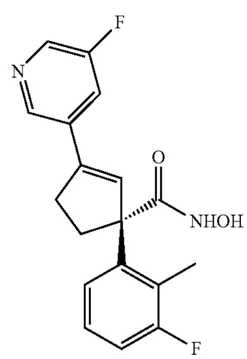 | 0.67 | 6.8 |
| 6 | (S)-1-(3-Fluoro-2-methylphenyl)-3-(5-fluoropyridin-3-yl)-N-hydroxycyclopent-2-enecarboxamide | 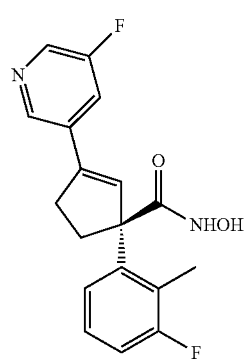 | 0.01 | 0.16 |

-continued

| Example # | Chemical Name | Structure | Biochemical HDAC-4 IC$_{50}$ (μM) | Cell IC$_{50}$ (μM) |
|---|---|---|---|---|
| 7 | (R)-1-(3-Fluoro-2-methylphenyl)-N-hydroxy-3-(pyrazin-2-yl)cyclopent-2-enecarboxamide | 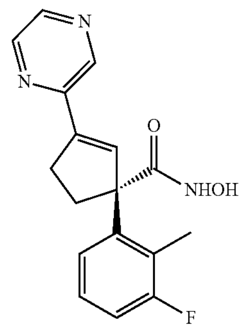 | >50 | >50 |
| 8 | (S)-1-(3-Fluoro-2-methylphenyl)-N-hydroxy-3-(pyrazin-2-yl)cyclopent-2-enecarboxamide | 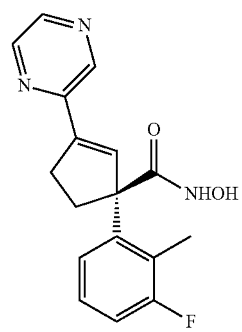 | 2.4 | 15.7 |
| 9 | (R)-1-(3-Fluoro-2-methylphenyl)-N-hydroxy-3-(2-methylpyrimidin-5-yl)cyclopent-2-enecarboxamide | 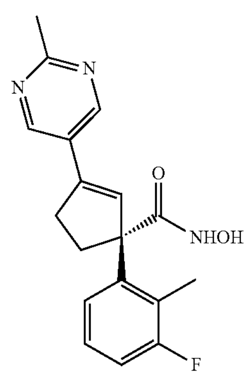 | 26.8 | >50 |
| 10 | (S)-1-(3-Fluoro-2-methylphenyl)-N-hydroxy-3-(2-methylpyrimidin-5-yl)cyclopent-2-enecarboxamide | 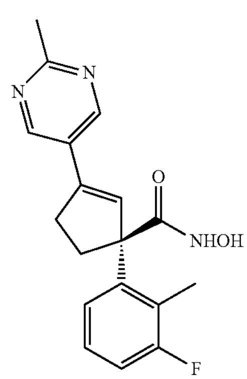 | 0.04 | 0.38 |

-continued

| Example # | Chemical Name | Structure | Biochemical HDAC-4 IC$_{50}$ (μM) | Cell IC$_{50}$ (μM) |
|---|---|---|---|---|
| 11 | (S)-3-(5-Chloropyridin-3-yl)-1-(3-fluoro-2-methylphenyl)-N-hydroxycyclopent-2-enecarboxamide | 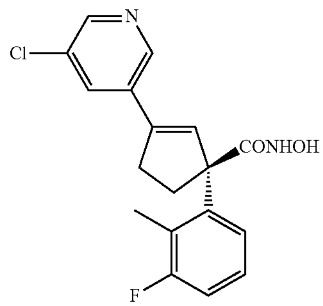 | 0.02 | 0.12 |
| 12 | (S)-1-(3-Fluoro-2-methylphenyl)-N-hydroxy-3-(quinoxalin-6-yl)cyclopent-2-enecarboxamide | 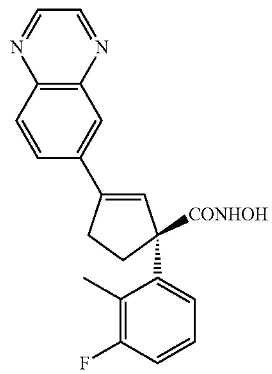 | 0.01 | 0.02 |
| 13 | (S)-1-(3-Fluoro-2-methylphenyl)-N-hydroxy-3-(2-(trifluoromethyl)pyridin-4-yl)cyclopent-2-enecarboxamide | 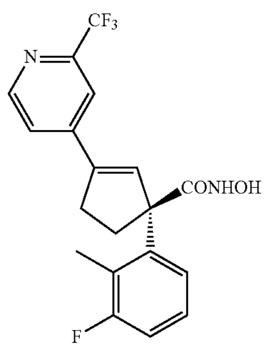 | 0.04 | 0.27 |
| 14 | (S)-1-(3-Fluoro-2-methylphenyl)-N-hydroxy-3-(pyrimidin-5-yl)cyclopent-2-enecarboxamide | 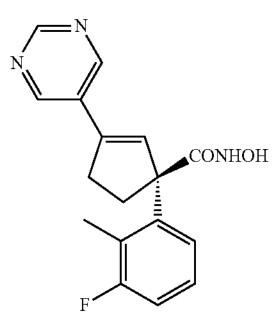 | 0.03 | 0.36 |

-continued

| Example # | Chemical Name | Structure | Biochemical HDAC-4 IC$_{50}$ (µM) | Cell IC$_{50}$ (µM) |
|---|---|---|---|---|
| 15 | (S)-1-(3-Fluoro-2-methylphenyl)-3-(5-fluoropyridin-2-yl)-N-hydroxycyclopent-2-enecarboxamide | 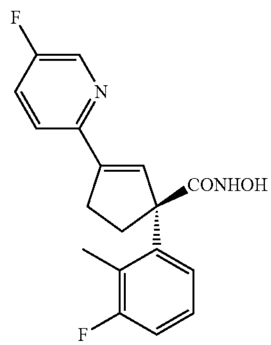 | 0.04 | 0.31 |
| 16 | (S)-1-(3-Fluoro-2-methylphenyl)-N-hydroxy-3-(6-(trifluoromethyl)pyridin-3-yl)cyclopent-2-enecarboxamide | 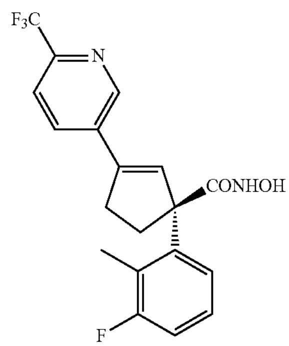 | 0.02 | 0.10 |
| 17 | (S)-1-(3-Fluoro-2-methylphenyl)-N-hydroxy-3-(5-(trifluoromethyl)pyridin-3-yl)cyclopent-2-enecarboxamide | 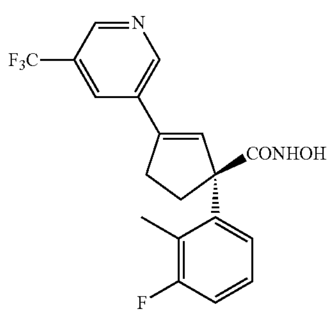 | 0.03 | 0.20 |
| 18 | (S)-3-(1-(Difluoromethyl)-1H-pyrazol-4-yl)-1-(3-fluoro-2-methylphenyl)-N-hydroxycyclopent-2-enecarboxamide | 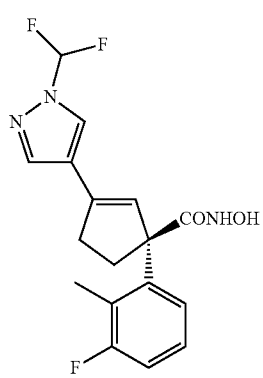 | 0.02 | 0.16 |

-continued

| Example # | Chemical Name | Structure | Biochemical HDAC-4 IC$_{50}$ (μM) | Cell IC$_{50}$ (μM) |
|---|---|---|---|---|
| 19 | (S)-3-(2-Cyclopropyl-5-fluoropyridin-3-yl)-1-(3-fluoro-2-methylphenyl)-N-hydroxycyclopent-2-enecarboxamide | 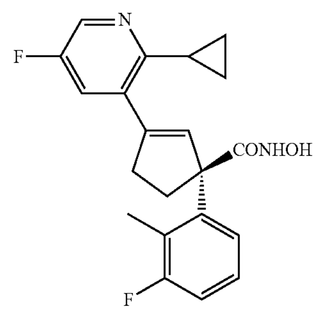 | 0.04 | 0.50 |
| 20 | (S)-1-(3-Fluoro-2-methylphenyl)-N-hydroxy-3-(2-(trifluoromethyl)quinoxalin-6-yl)cyclopent-2-enecarboxamide | 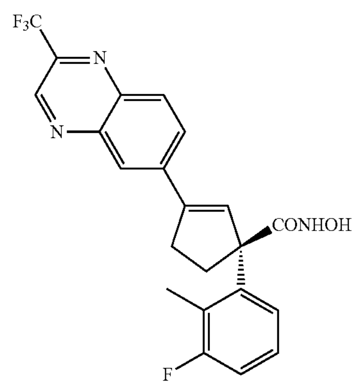 | 0.07 | 0.14 |
| 21 | (S)-1-(3-Fluoro-2-methylphenyl)-N-hydroxy-3-(imidazo[1,2-a]pyridin-7-yl)cyclopent-2-enecarboxamide | 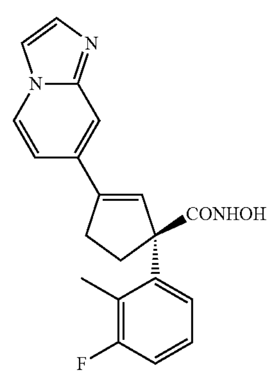 | 0.01 | 0.06 |
| 22 | (S)-1-(3-Fluoro-2-methylphenyl)-N-hydroxy-3-(3-methylbenzo[d]isoxazol-5-yl)cyclopent-2-enecarboxamide | 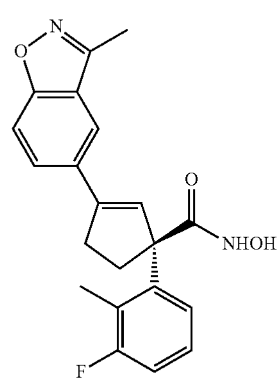 | 0.03 | 0.06 |

-continued

| Example # | Chemical Name | Structure | Biochemical HDAC-4 IC$_{50}$ (μM) | Cell IC$_{50}$ (μM) |
|---|---|---|---|---|
| 23 | (S)-1-(3-Fluoro-2-methylphenyl)-3-(5-fluoro-6-methoxypyridin-3-yl)-N-hydroxycyclopent-2-enecarboxamide | 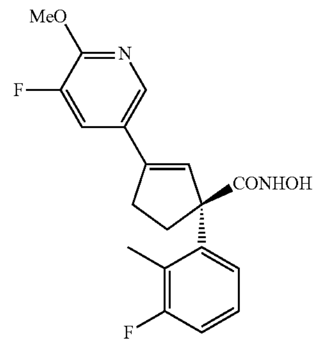 | 0.04 | 0.22 |
| 24 | (S)-3-(2-Cyclopropylpyrimidin-5-yl)-1-(3-fluoro-2-methylphenyl)-N-hydroxycyclopent-2-enecarboxamide | 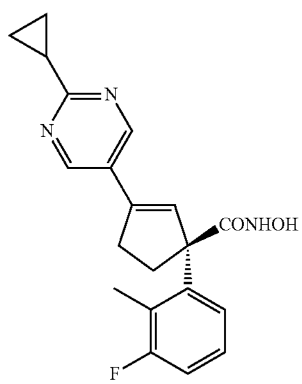 | 0.02 | 0.08 |
| 25 | (S)-1-(3-Fluoro-2-methylphenyl)-N-hydroxy-3-(6-methylpyridin-3-yl)cyclopent-2-enecarboxamide | 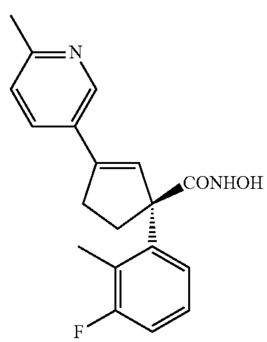 | 0.01 | 0.12 |
| 26 | (S)-3-(5-Chloro-6-methylpyridin-3-yl)-1-(3-fluoro-2-methylphenyl)-N-hydroxycyclopent-2-enecarboxamide | 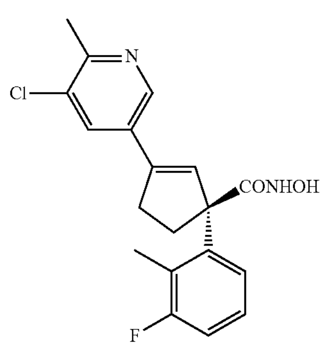 | 0.01 | 0.08 |

-continued

| Example # | Chemical Name | Structure | Biochemical HDAC-4 IC$_{50}$ (µM) | Cell IC$_{50}$ (µM) |
|---|---|---|---|---|
| 27 | (S)-1-(3-Fluoro-2-methylphenyl)-N-hydroxy-3-(1-methyl-1H-pyrazol-5-yl)cyclopent-2-enecarboxamide | 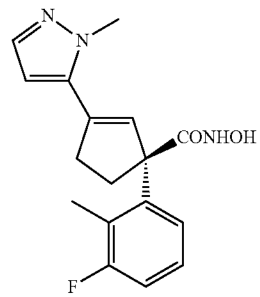 | 0.02 | 0.33 |
| 28 | (S)-1-(3-Fluoro-2-methylphenyl)-N-hydroxy-3-(1-(2,2,2-trifluoroethyl)-1H-pyrazol-4-yl)cyclopent-2-enecarboxamide | 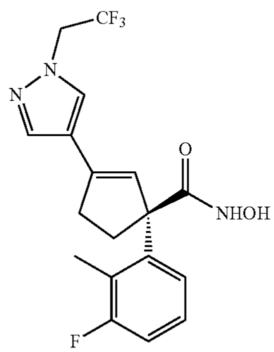 | 0.02 | 0.16 |
| 29 | (S)-3-(Benzo[d]isothiazol-7-yl)-1-(3-fluoro-2-methylphenyl)-N-hydroxycyclopent-2-enecarboxamide | 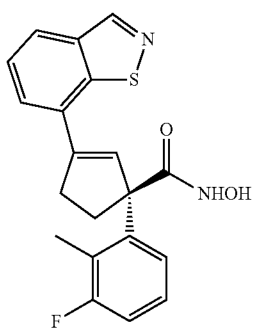 | 0.03 | 0.20 |
| 30 | N-Hydroxy-1-phenylcyclopent-3-enecarboxamide | 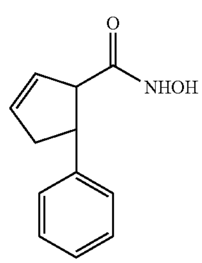 | 12.3 | >50 |
| 31 | 1-(2-Fluorophenyl)-N-hydroxycyclopent-3-enecarboxamide | 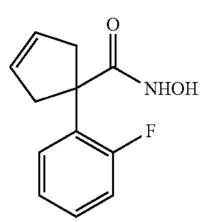 | 8.3 | 44.5 |

-continued

| Example # | Chemical Name | Structure | Biochemical HDAC-4 IC$_{50}$ (μM) | Cell IC$_{50}$ (μM) |
|---|---|---|---|---|
| 32 | (S)-3-Cyclopropyl-1-(3-fluoro-2-methylphenyl)-N-hydroxycyclopent-2-enecarboxamide | 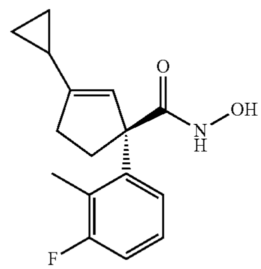 [SMILES: Cc1c(F)cccc1[C@@]1(C(=O)NO)C=C(C2CC2)CC1] | 0.04 | 0.73 |
| 33 | (S)-N-Hydroxy-1,3-diphenylcyclopent-2-enecarboxamide | 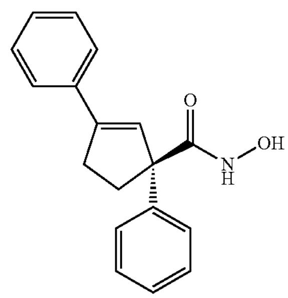 [SMILES: O=C(NO)[C@]1(c2ccccc2)C=C(c2ccccc2)CC1] | 0.19 | 2.5 |
| 34 | (R)-N-Hydroxy-1,3-diphenylcyclopent-2-enecarboxamide | 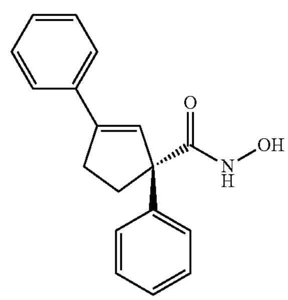 [SMILES: O=C(NO)[C@@]1(c2ccccc2)C=C(c2ccccc2)CC1] | 31 | >50 |
| 35 | (S)-3-(5-Fluoropyridin-3-yl)-N-hydroxy-1-phenylcyclopent-2-enecarboxamide | 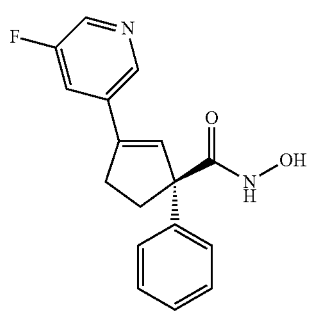 [SMILES: O=C(NO)[C@]1(c2ccccc2)C=C(c2cncc(F)c2)CC1] | 0.34 | 3.1 |
| 36 | (S)-3-(5-Chloro-2-methylpyridin-3-yl)-1-(3-fluoro-2-methylphenyl)-N-hydroxycyclopent-2-enecarboxamide | 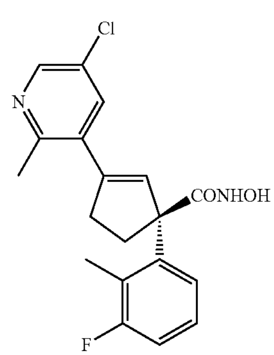 | 0.02 | 0.12 |

-continued

| Example # | Chemical Name | Structure | Biochemical HDAC-4 IC$_{50}$ (μM) | Cell IC$_{50}$ (μM) |
|---|---|---|---|---|
| 37 | (S)-1-(3-Fluoro-2-methylphenyl)-N-hydroxy-3-(2-methylpyridin-3-yl)cyclopent-2-enecarboxamide | 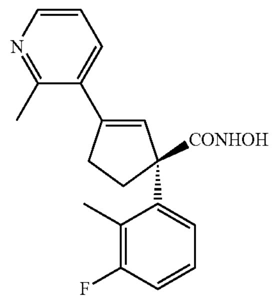 | 0.01 | 0.09 |
| 38 | (S)-1-(3-Fluoro-2-methylphenyl)-N-hydroxy-3-(1-methyl-1H-indazol-6-yl)cyclopent-2-enecarboxamide | 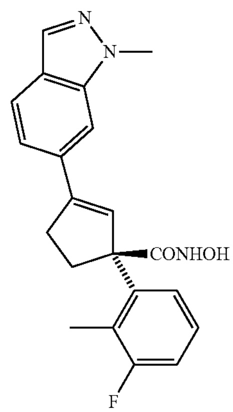 | 0.01 | 0.01 |
| 39 | (S)-3-(1-(Difluoromethyl)-1H-indazol-6-yl)-1-(3-fluoro-2-methylphenyl)-N-hydroxycyclopent-2-enecarboxamide | 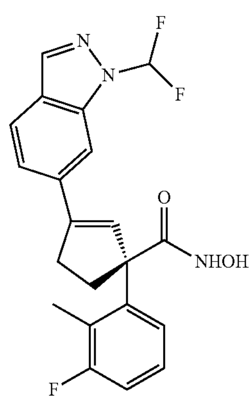 | 0.03 | 0.03 |
| 40 | (S)-3-(Benzo[d]thiazol-5-yl)-1-(3-fluoro-2-methylphenyl)-N-hydroxycyclopent-2-enecarboxamide | 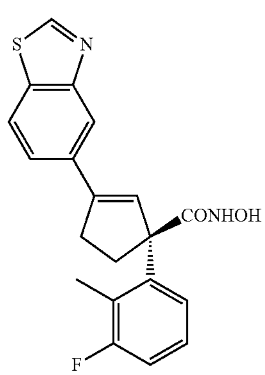 | 0.01 | 0.05 |

-continued

| Example # | Chemical Name | Structure | Biochemical HDAC-4 IC$_{50}$ (μM) | Cell IC$_{50}$ (μM) |
|---|---|---|---|---|
| 41 | (S)-3-(Benzo[b]thiophen-2-yl)-1-(3-fluoro-2-methylphenyl)-N-hydroxycyclopent-2-enecarboxamide | 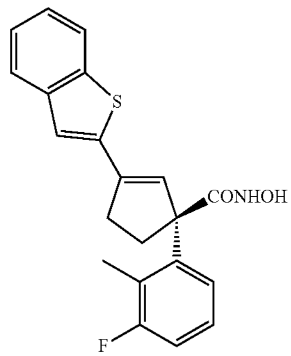 | 0.02 | 0.04 |
| 42 | (S)-1-(3,4-Difluoro-2-methylphenyl)-N-hydroxy-3-(1-methyl-1H-indazol-6-yl)cyclopent-2-enecarboxamide | 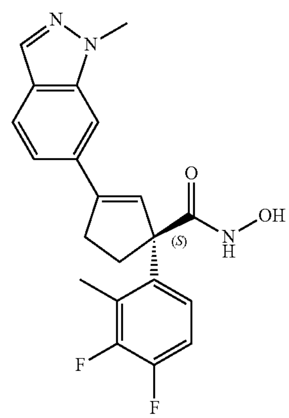 | 0.01 | 0.02 |
| 43 | 4-(5-Fluoropyridin-3-yl)-N-hydroxy-1,2,3,6-tetrahydro-[1,1'-biphenyl]-1-carboxamide | 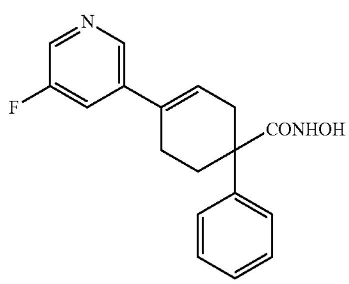 | 3.6 | 39 |
| 44 | 3'-Fluoro-4-(5-fluoropyridin-3-yl)-N-hydroxy-2'-methyl-1,2,3,6-tetrahydro-[1,1'-biphenyl]-1-carboxamide | 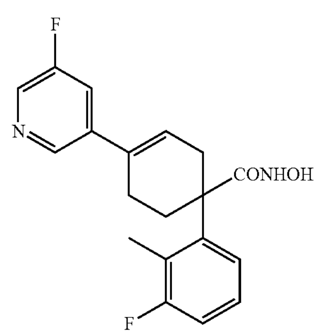 | 0.49 | 0.67 |

| Example # | Chemical Name | Structure | Biochemical HDAC-4 IC$_{50}$ (µM) | Cell IC$_{50}$ (µM) |
|---|---|---|---|---|
| 45 | (S)-1-(3-Fluoro-2-methylphenyl)-N-hydroxy-3-(quinoxalin-6-yl)cyclopent-2-enecarboxamide | 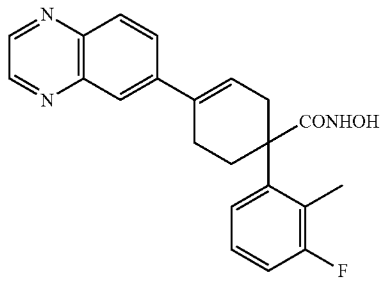 | 0.55 | 0.52 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. A method for treating a patient suffering from a condition or disorder mediated by at least one histone deacetylase, wherein the condition or disorder is cancer, amyotrophic lateral sclerosis (ALS), diabetes, a cardiovascular condition, epilepsy, depression, viral infection, or fungal infection, and wherein the method comprises administering to the patient a therapeutically effective amount of a compound of Formula I, or a pharmaceutically acceptable salt thereof,

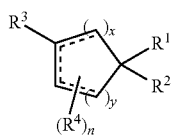

Formula I wherein:
each of the dashed lines indicate a single or double bond, provided that the ring contains one or two double bonds that are non-adjacent;
$R^1$ is —C(O)NH(OH) or —N(OH)C(O)$R^5$, wherein $R^5$ is hydrogen, lower alkyl or lower haloalkyl;
$R^2$ is aryl, heteroaryl, or heterocycloalkyl, each of which is optionally substituted with 1 to 3 substituents independently selected from halo, alkyl, cycloalkyl, haloalkyl, hydroxyl, alkoxy, and nitrile; and
$R^3$ is hydrogen, alkyl, cycloalkyl, heterocycloalkyl, aryl, heteroaryl, aralkyl, or heteroaralkyl, each of which is optionally substituted with 1 to 3 substituents independently selected from halo, CONR$_b$R$_c$, alkyl, alkyl substituted with —NR$_b$R$_c$, cycloalkyl, haloalkyl, hydroxyl, alkoxy, alkoxy substituted with —NR$_b$R$_c$, aryl, heteroaryl, and nitrile;

for each occurrence, $R^4$ is independently selected from halo, lower alkyl, lower haloalkyl, and hydroxyl;
x and y are independently selected from 1, 2, and 3, provided that the sum of x+y is ≤4,
n is 0, 1, 2 or 3;
$R_b$ is hydrogen, $C_1$-$C_6$ alkyl, aryl, or heteroaryl; and
$R_c$ is hydrogen or $C_1$-$C_4$ alkyl; or
$R_b$ and $R_c$, and the nitrogen to which they are attached, form a heterocycloalkyl group; and
where for $R_b$ and $R_c$, each $C_1$-$C_6$ alkyl, aryl, heterocycloalkyl, and heteroaryl is unsubstituted or substituted with one or more substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —OC$_1$-C$_4$ alkyl, —OC$_1$-C$_4$ alkylphenyl, —C$_1$-C$_4$ alkyl-OH, —C$_1$-C$_4$ alkyl-O—C$_1$-C$_4$ alkyl, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

2. The method of claim 1, wherein the compound of Formula I is a compound of Formula II, Formula III, or Formula IV:

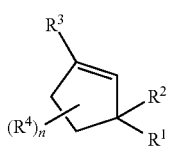

Formula II

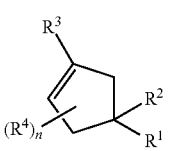

Formula III

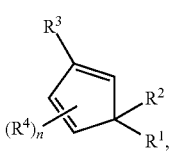

Formula IV or a pharmaceutically acceptable salt thereof.

3. The method of claim 1, wherein the compound of Formula I is a compound of Formula XI, Formula XII, or Formula XIII:

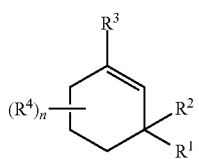

Formula XI

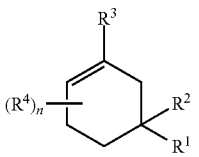

Formula XII

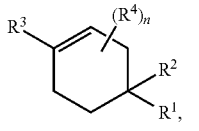

Formula XIII or a pharmaceutically acceptable salt thereof.

4. The method of claim 1, wherein $R^1$ is —C(O)NH(OH).

5. The method of claim 1, wherein $R^1$ is —N(OH)C(O)$R^5$.

6. The method of claim 1, wherein $R^2$ is phenyl optionally substituted with 1 to 3 substituents independently selected from halo, alkyl, cycloalkyl, haloalkyl, hydroxyl, alkoxy, and nitrile.

7. The method of claim 1, wherein $R^2$ is heteroaryl optionally substituted with 1 to 3 substituents independently selected from halo, alkyl, and haloalkyl.

8. The method of claim 1, wherein $R^3$ is hydrogen, alkyl, cycloalkyl, heterocycloalkyl, aryl, heteroaryl, aralkyl, or heteroaralkyl, each of which is optionally substituted with 1 to 3 substituents independently selected from halo, alkyl, cycloalkyl, haloalkyl, hydroxyl, alkoxy, and nitrile.

9. A method for treating a patient suffering from a condition or disorder mediated by at least one histone deacetylase, wherein the condition or disorder is cancer, amyotrophic lateral sclerosis (ALS), diabetes, a cardiovascular condition, epilepsy, depression, viral infection, or fungal infection, wherein the method comprises administering to the patient a therapeutically effective amount of a compound, or a pharmaceutically acceptable salt thereof, selected from:

(R)-1-(3-fluoro-2-methylphenyl)-N-hydroxy-3-phenylcyclopent-2-enecarboxamide;
(S)-1-(3-fluoro-2-methylphenyl)-N-hydroxy-3-phenylcyclopent-2-enecarboxamide;
(R)-1-(3-fluoro-2-methylphenyl)-N-hydroxy-3-(o-tolyl)cyclopent-2-enecarboxamide;
(S)-1-(3-fluoro-2-methylphenyl)-N-hydroxy-3-(o-tolyl)cyclopent-2-enecarboxamide;
(R)-1-(3-fluoro-2-methylphenyl)-3-(5-fluoropyridin-3-yl)-N-hydroxycyclopent-2-enecarboxamide;
(S)-1-(3-fluoro-2-methylphenyl)-3-(5-fluoropyridin-3-yl)-N-hydroxycyclopent-2-enecarboxamide;
(R)-1-(3-fluoro-2-methylphenyl)-N-hydroxy-3-(pyrazin-2-yl)cyclopent-2-enecarboxamide;
(S)-1-(3-fluoro-2-methylphenyl)-N-hydroxy-3-(pyrazin-2-yl)cyclopent-2-enecarboxamide;
(R)-1-(3-fluoro-2-methylphenyl)-N-hydroxy-3-(2-methylpyrimidin-5-yl)cyclopent-2-enecarboxamide;
(S)-1-(3-fluoro-2-methylphenyl)-N-hydroxy-3-(2-methylpyrimidin-5-yl)cyclopent-2-enecarboxamide;
(S)-3-(5-chloropyridin-3-yl)-1-(3-fluoro-2-methylphenyl)-N-hydroxycyclopent-2-enecarboxamide;
(S)-1-(3-fluoro-2-methylphenyl)-N-hydroxy-3-(quinoxalin-6-yl)cyclopent-2-enecarboxamide;
(S)-1-(3-fluoro-2-methylphenyl)-N-hydroxy-3-(2-(trifluoromethyl)pyridin-4-yl)cyclopent-2-enecarboxamide;
(S)-1-(3-fluoro-2-methylphenyl)-N-hydroxy-3-(pyrimidin-5-yl)cyclopent-2-enecarboxamide;
(S)-1-(3-fluoro-2-methylphenyl)-3-(5-fluoropyridin-2-yl)-N-hydroxycyclopent-2-enecarboxamide;
(S)-1-(3-fluoro-2-methylphenyl)-N-hydroxy-3-(6-(trifluoromethyl)pyridin-3-yl)cyclopent-2-enecarboxamide;
(S)-1-(3-fluoro-2-methylphenyl)-N-hydroxy-3-(5-(trifluoromethyl)pyridin-3-yl)cyclopent-2-enecarboxamide;
(S)-3-(1-(difluoromethyl)-1H-pyrazol-4-yl)-1-(3-fluoro-2-methylphenyl)-N-hydroxycyclopent-2-enecarboxamide;
(S)-3-(2-cyclopropyl-5-fluoropyridin-3-yl)-1-(3-fluoro-2-methylphenyl)-N-hydroxycyclopent-2-enecarboxamide;
(S)-1-(3-fluoro-2-methylphenyl)-N-hydroxy-3-(2-(trifluoromethyl)quinoxalin-6-yl)cyclopent-2-enecarboxamide;
(S)-1-(3-fluoro-2-methylphenyl)-N-hydroxy-3-(imidazo[1,2-a]pyridin-7-yl)cyclopent-2-enecarboxamide;
(S)-1-(3-fluoro-2-methylphenyl)-N-hydroxy-3-(3-methylbenzo[d]isoxazol-5-yl)cyclopent-2-enecarboxamide;
(S)-1-(3-fluoro-2-methylphenyl)-3-(5-fluoro-6-methoxypyridin-3-yl)-N-hydroxycyclopent-2-enecarboxamide;
(S)-3-(2-cyclopropylpyrimidin-5-yl)-1-(3-fluoro-2-methylphenyl)-N-hydroxycyclopent-2-enecarboxamide;
(S)-1-(3-fluoro-2-methylphenyl)-N-hydroxy-3-(6-methylpyridin-3-yl)cyclopent-2-enecarboxamide;
(S)-3-(5-chloro-6-methylpyridin-3-yl)-1-(3-fluoro-2-methylphenyl)-N-hydroxycyclopent-2-enecarboxamide;
(S)-1-(3-fluoro-2-methylphenyl)-N-hydroxy-3-(1-methyl-1H-pyrazol-5-yl)cyclopent-2-enecarboxamide;
(S)-1-(3-fluoro-2-methylphenyl)-N-hydroxy-3-(1-(2,2,2-trifluoroethyl)-1H-pyrazol-4-yl)cyclopent-2-enecarboxamide;
(S)-3-(benzo[d]isothiazol-7-yl)-1-(3-fluoro-2-methylphenyl)-N-hydroxycyclopent-2-enecarboxamide;
N-hydroxy-1-phenylcyclopent-3-enecarboxamide;
1-(2-fluorophenyl)-N-hydroxycyclopent-3-enecarboxamide;
(S)-3-cyclopropyl-1-(3-fluoro-2-methylphenyl)-N-hydroxycyclopent-2-enecarboxamide;
(S)-N-hydroxy-1,3-diphenylcyclopent-2-enecarboxamide;
(R)-N-hydroxy-1,3-diphenylcyclopent-2-enecarboxamide;

(S)-3-(5-fluoropyridin-3-yl)-N-hydroxy-1-phenylcyclopent-2-enecarboxamide;
(S)-3-(5-chloro-2-methylpyridin-3-yl)-1-(3-fluoro-2-methylphenyl)-N-hydroxycyclopent-2-enecarboxamide;
(S)-1-(3-fluoro-2-methylphenyl)-N-hydroxy-3-(2-methylpyridin-3-yl)cyclopent-2-enecarboxamide;
(S)-1-(3-fluoro-2-methylphenyl)-N-hydroxy-3-(1-methyl-1H-indazol-6-yl)cyclopent-2-enecarboxamide;
(S)-3-(1-(difluoromethyl)-1H-indazol-6-yl)-1-(3-fluoro-2-methylphenyl)-N-hydroxycyclopent-2-enecarboxamide;
(S)-3-(benzo[d]thiazol-5-yl)-1-(3-fluoro-2-methylphenyl)-N-hydroxycyclopent-2-enecarboxamide;
(S)-3-(benzo[b]thiophen-2-yl)-1-(3-fluoro-2-methylphenyl)-N-hydroxycyclopent-2-enecarboxamide;
(S)-1-(3,4-difluoro-2-methylphenyl)-N-hydroxy-3-(1-methyl-1H-indazol-6-yl)cyclopent-2-enecarboxamide;
4-(5-fluoropyridin-3-yl)-N-hydroxy-1,2,3,6-tetrahydro-[1,1'-biphenyl]-1-carboxamide;
3'-fluoro-4-(5-fluoropyridin-3-yl)-N-hydroxy-2'-methyl-1,2,3,6-tetrahydro-[1,1'-biphenyl]-1-carboxamide; and
3'-fluoro-N-hydroxy-2'-methyl-4-(quinoxalin-6-yl)-1,2,3,6-tetrahydro-[1,1'-biphenyl]-1-carboxamide.

10. A method for treating a patient suffering from a neurodegenerative condition, wherein the method comprises administering to the patient a therapeutically effective amount of a compound of Formula I, or a pharmaceutically acceptable salt thereof,

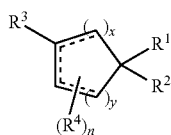

Formula I wherein:
each of the dashed lines indicate a single or double bond, provided that the ring contains one or two double bonds that are non-adjacent;
$R^1$ is —C(O)NH(OH) or —N(OH)C(O)$R^5$, wherein $R^5$ is hydrogen, lower alkyl or lower haloalkyl;
$R^2$ is aryl, heteroaryl, or heterocycloalkyl, each of which is optionally substituted with 1 to 3 substituents independently selected from halo, alkyl, cycloalkyl, haloalkyl, hydroxyl, alkoxy, and nitrile; and
$R^3$ is hydrogen, alkyl, cycloalkyl, heterocycloalkyl, aryl, heteroaryl, aralkyl, or heteroaralkyl, each of which is optionally substituted with 1 to 3 substituents independently selected from halo, CONR$_b$R$_c$, alkyl, alkyl substituted with —NR$_b$R$_c$, cycloalkyl, haloalkyl, hydroxyl, alkoxy, alkoxy substituted with —NR$_b$R$_c$, aryl, heteroaryl, and nitrile;
for each occurrence, $R^4$ is independently selected from halo, lower alkyl, lower haloalkyl, and hydroxyl;
x and y are independently selected from 1, 2, and 3, provided that the sum of x+y is ≤4,
n is 0, 1, 2 or 3;
$R_b$ is hydrogen, $C_1$-$C_6$ alkyl, aryl, or heteroaryl; and
$R_c$ is hydrogen or $C_1$-$C_4$ alkyl; or
$R_b$ and $R_c$, and the nitrogen to which they are attached, form a heterocycloalkyl group; and
where for $R_b$ and $R_c$, each $C_1$-$C_6$ alkyl, aryl, heterocycloalkyl, and heteroaryl is unsubstituted or substituted with one or more substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —$C_1$-$C_4$ alkyl-O—$C_1$-$C_4$ alkyl, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl), and the neurodegenerative condition is Alzheimer's disease, Parkinson's disease, neuronal intranuclear inclusion disease (NIID), Dentatorubral pallidolusyian atrophy (DRPLA), Friedreich's ataxia, Rubenstein-Taubi Syndrome, a polyglutamine disease; spinocerebellar ataxia 1 (SCA 1), spinocerebellar ataxia 7 (SCA 7), seizures, striatonigral degeneration, progressive supranuclear palsy, torsion dystonia, spasmodic torticollis, dyskinesis, familial tremor, Gilles de la Tourette syndrome, diffuse Lewy body disease, progressive supranuclear palsy, Pick's disease, primary lateral sclerosis, progressive neural muscular atrophy, spinal muscular atrophy, hypertrophic interstitial polyneuropathy, retinitis pigmentosa, hereditary optic atrophy, hereditary spastic paraplegia, Shy-Drager syndrome, Kennedy's disease, protein-aggregation-related neurodegeneration, Machado-Joseph's disease, spongiform encephalopathy, prion-related disease, multiple sclerosis (MS), progressive supranuclear palsy (Steel-Richardson-Olszewski disease), Hallervorden-Spatz disease, progressive familial myoclonic epilepsy, cerebellar degeneration, motor neuron disease, Werdnig-Hoffman disease, Wohlfart-Kugelberg-Welander disease, Charcot-Marie-Tooth disease, Dejerine-Sottas disease, retinitis pigmentosa, Leber's disease, progressive systemic sclerosis, dermatomyositis, or mixed connective tissue disease.

11. The method of claim 10, wherein the compound of Formula I is a compound of Formula II, Formula III, or Formula IV:

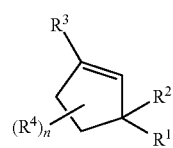

Formula II

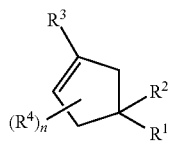

Formula III

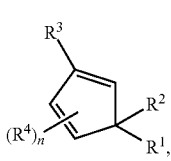

Formula IV or a pharmaceutically acceptable salt thereof.

12. The method of claim 10, wherein the compound of Formula I is a compound of Formula XI, Formula XII, or Formula XIII:

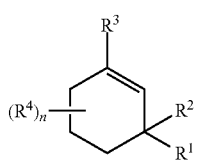

Formula XI

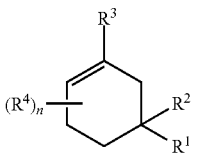

Formula XII

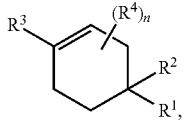

Formula XIII or a pharmaceutically acceptable salt thereof.

13. The method of claim 10, wherein $R^1$ is —C(O)NH(OH).

14. The method of claim 10, wherein $R^1$ is —N(OH)C(O)$R^5$.

15. The method of claim 10, wherein $R^2$ is phenyl optionally substituted with 1 to 3 substituents independently selected from halo, alkyl, cycloalkyl, haloalkyl, hydroxyl, alkoxy, and nitrile.

16. The method of claim 10, wherein $R^2$ is heteroaryl optionally substituted with 1 to 3 substituents independently selected from halo, alkyl, and haloalkyl.

17. The method of claim 10, wherein $R^3$ is hydrogen, alkyl, cycloalkyl, heterocycloalkyl, aryl, heteroaryl, aralkyl, or heteroaralkyl, each of which is optionally substituted with 1 to 3 substituents independently selected from halo, alkyl, cycloalkyl, haloalkyl, hydroxyl, alkoxy, and nitrile.

18. A method for treating a patient suffering from a neurodegenerative condition selected from Alzheimer's disease, Parkinson's disease, neuronal intranuclear inclusion disease (NIID), Dentatorubral pallidolusyian atrophy (DRPLA), Friedreich's ataxia, Rubenstein-Taubi Syndrome, a polyglutamine disease; spinocerebellar ataxia 1 (SCA 1), spinocerebellar ataxia 7 (SCA 7), seizures, striatonigral degeneration, progressive supranuclear palsy, torsion dystonia, spasmodic torticollis, dyskinesis, familial tremor, Gilles de la Tourette syndrome, diffuse Lewy body disease, progressive supranuclear palsy, Pick's disease, primary lateral sclerosis, progressive neural muscular atrophy, spinal muscular atrophy, hypertrophic interstitial polyneuropathy, retinitis pigmentosa, hereditary optic atrophy, hereditary spastic paraplegia, Shy-Drager syndrome, Kennedy's disease, protein-aggregation-related neurodegeneration, Machado-Joseph's disease, spongiform encephalopathy, prion-related disease, multiple sclerosis (MS), progressive supranuclear palsy (Steel-Richardson-Olszewski disease), Hallervorden-Spatz disease, progressive familial myoclonic epilepsy, cerebellar degeneration, motor neuron disease, Werdnig-Hoffman disease, Wohlfart-Kugelberg-Welander disease, Charcot-Marie-Tooth disease, Dejerine-Sottas disease, retinitis pigmentosa, Leber's disease, progressive systemic sclerosis, dermatomyositis, and mixed connective tissue disease;
  wherein the method comprises administering to the patient a therapeutically effective amount of a compound, or a pharmaceutically acceptable salt thereof, selected from:
  (R)-1-(3-fluoro-2-methylphenyl)-N-hydroxy-3-phenylcyclopent-2-enecarboxamide;
  (S)-1-(3-fluoro-2-methylphenyl)-N-hydroxy-3-phenylcyclopent-2-enecarboxamide;
  (R)-1-(3-fluoro-2-methylphenyl)-N-hydroxy-3-(o-tolyl)cyclopent-2-enecarboxamide;
  (S)-1-(3-fluoro-2-methylphenyl)-N-hydroxy-3-(o-tolyl)cyclopent-2-enecarboxamide;
  (R)-1-(3-fluoro-2-methylphenyl)-3-(5-fluoropyridin-3-yl)-N-hydroxycyclopent-2-enecarboxamide;
  (S)-1-(3-fluoro-2-methylphenyl)-3-(5-fluoropyridin-3-yl)-N-hydroxycyclopent-2-enecarboxamide;
  (R)-1-(3-fluoro-2-methylphenyl)-N-hydroxy-3-(pyrazin-2-yl)cyclopent-2-enecarboxamide;
  (S)-1-(3-fluoro-2-methylphenyl)-N-hydroxy-3-(pyrazin-2-yl)cyclopent-2-enecarboxamide;
  (R)-1-(3-fluoro-2-methylphenyl)-N-hydroxy-3-(2-methylpyrimidin-5-yl)cyclopent-2-enecarboxamide;
  (S)-1-(3-fluoro-2-methylphenyl)-N-hydroxy-3-(2-methylpyrimidin-5-yl)cyclopent-2-enecarboxamide;
  (S)-3-(5-chloropyridin-3-yl)-1-(3-fluoro-2-methylphenyl)-N-hydroxycyclopent-2-enecarboxamide;
  (S)-1-(3-fluoro-2-methylphenyl)-N-hydroxy-3-(quinoxalin-6-yl)cyclopent-2-enecarboxamide;
  (S)-1-(3-fluoro-2-methylphenyl)-N-hydroxy-3-(2-(trifluoromethyl)pyridin-4-yl)cyclopent-2-enecarboxamide;
  (S)-1-(3-fluoro-2-methylphenyl)-N-hydroxy-3-(pyrimidin-5-yl)cyclopent-2-enecarboxamide;
  (S)-1-(3-fluoro-2-methylphenyl)-3-(5-fluoropyridin-2-yl)-N-hydroxycyclopent-2-enecarboxamide;
  (S)-1-(3-fluoro-2-methylphenyl)-N-hydroxy-3-(6-(trifluoromethyl)pyridin-3-yl)cyclopent-2-enecarboxamide;
  (S)-1-(3-fluoro-2-methylphenyl)-N-hydroxy-3-(5-(trifluoromethyl)pyridin-3-yl)cyclopent-2-enecarboxamide;
  (S)-3-(1-(difluoromethyl)-1H-pyrazol-4-yl)-1-(3-fluoro-2-methylphenyl)-N-hydroxycyclopent-2-enecarboxamide;
  (S)-3-(2-cyclopropyl-5-fluoropyridin-3-yl)-1-(3-fluoro-2-methylphenyl)-N-hydroxycyclopent-2-enecarboxamide;
  (S)-1-(3-fluoro-2-methylphenyl)-N-hydroxy-3-(2-(trifluoromethyl)quinoxalin-6-yl)cyclopent-2-enecarboxamide;
  (S)-1-(3-fluoro-2-methylphenyl)-N-hydroxy-3-(imidazo[1,2-a]pyridin-7-yl)cyclopent-2-enecarboxamide;
  (S)-1-(3-fluoro-2-methylphenyl)-N-hydroxy-3-(3-methylbenzo[d]isoxazol-5-yl)cyclopent-2-enecarboxamide;
  (S)-1-(3-fluoro-2-methylphenyl)-3-(5-fluoro-6-methoxypyridin-3-yl)-N-hydroxycyclopent-2-enecarboxamide;

(S)-3-(2-cyclopropylpyrimidin-5-yl)-1-(3-fluoro-2-methylphenyl)-N-hydroxycyclopent-2-enecarboxamide;
(S)-1-(3-fluoro-2-methylphenyl)-N-hydroxy-3-(6-methylpyridin-3-yl)cyclopent-2-enecarboxamide;
(S)-3-(5-chloro-6-methylpyridin-3-yl)-1-(3-fluoro-2-methylphenyl)-N-hydroxycyclopent-2-enecarboxamide;
(S)-1-(3-fluoro-2-methylphenyl)-N-hydroxy-3-(1-methyl-1H-pyrazol-5-yl)cyclopent-2-enecarboxamide;
(S)-1-(3-fluoro-2-methylphenyl)-N-hydroxy-3-(1-(2,2,2-trifluoroethyl)-1H-pyrazol-4-yl)cyclopent-2-enecarboxamide;
(S)-3-(benzo[d]isothiazol-7-yl)-1-(3-fluoro-2-methylphenyl)-N-hydroxycyclopent-2-enecarboxamide;
N-hydroxy-1-phenylcyclopent-3-enecarboxamide;
1-(2-fluorophenyl)-N-hydroxycyclopent-3-enecarboxamide;
(S)-3-cyclopropyl-1-(3-fluoro-2-methylphenyl)-N-hydroxycyclopent-2-enecarboxamide;
(S)-N-hydroxy-1,3-diphenylcyclopent-2-enecarboxamide;
(R)-N-hydroxy-1,3-diphenylcyclopent-2-enecarboxamide;
(S)-3-(5-fluoropyridin-3-yl)-N-hydroxy-1-phenylcyclopent-2-enecarboxamide;
(S)-3-(5-chloro-2-methylpyridin-3-yl)-1-(3-fluoro-2-methylphenyl)-N-hydroxycyclopent-2-enecarboxamide;
(S)-1-(3-fluoro-2-methylphenyl)-N-hydroxy-3-(2-methylpyridin-3-yl)cyclopent-2-enecarboxamide;
(S)-1-(3-fluoro-2-methylphenyl)-N-hydroxy-3-(1-methyl-1H-indazol-6-yl)cyclopent-2-enecarboxamide;
(S)-3-(1-(difluoromethyl)-1H-indazol-6-yl)-1-(3-fluoro-2-methylphenyl)-N-hydroxycyclopent-2-enecarboxamide;
(S)-3-(benzo[d]thiazol-5-yl)-1-(3-fluoro-2-methylphenyl)-N-hydroxycyclopent-2-enecarboxamide;
(S)-3-(benzo[b]thiophen-2-yl)-1-(3-fluoro-2-methylphenyl)-N-hydroxycyclopent-2-enecarboxamide;
(S)-1-(3,4-difluoro-2-methylphenyl)-N-hydroxy-3-(1-methyl-1H-indazol-6-yl)cyclopent-2-enecarboxamide;
4-(5-fluoropyridin-3-yl)-N-hydroxy-1,2,3,6-tetrahydro-[1,1'-biphenyl]-1-carboxamide;
3'-fluoro-4-(5-fluoropyridin-3-yl)-N-hydroxy-2'-methyl-1,2,3,6-tetrahydro-[1,1'-biphenyl]-1-carboxamide; and
3'-fluoro-N-hydroxy-2'-methyl-4-(quinoxalin-6-yl)-1,2,3,6-tetrahydro-[1,1'-biphenyl]-1-carboxamide.

\* \* \* \* \*